(12) United States Patent
Xu

(10) Patent No.: US 9,944,989 B2
(45) Date of Patent: Apr. 17, 2018

(54) MICRORNAS AS NEW THERAPEUTIC TARGETS FOR THE PREVENTION AND/OR TREATMENT OF RETINOPATHY

(71) Applicant: RUSH UNIVERSITY MEDICAL CENTER, Chicago, IL (US)

(72) Inventor: Shunbin Xu, Oak Park, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 15/335,271

(22) Filed: Oct. 26, 2016

(65) Prior Publication Data
US 2017/0159123 A1 Jun. 8, 2017

Related U.S. Application Data

(60) Division of application No. 13/907,399, filed on May 31, 2013, now abandoned, which is a continuation-in-part of application No. PCT/US2011/063400, filed on Dec. 6, 2011.

(60) Provisional application No. 61/420,201, filed on Dec. 6, 2010.

(51) Int. Cl.
*C12N 15/11* (2006.01)
*C12Q 1/68* (2018.01)
*C12N 15/113* (2010.01)

(52) U.S. Cl.
CPC .......... *C12Q 1/6883* (2013.01); *C12N 15/113* (2013.01); *C12N 2310/141* (2013.01); *C12N 2320/32* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2007/0161004 A1 | 7/2007 | Brown et al. |
| 2007/0232553 A1 | 10/2007 | Baltimore |
| 2008/0280811 A1 | 11/2008 | Feener et al. |
| 2009/0281167 A1 | 11/2009 | Shen et al. |
| 2010/0173288 A1 | 7/2010 | Zhang et al. |

OTHER PUBLICATIONS

Huang et al., "A Novel Lysophospholipid- and pH-Sensitive Receptor,GPR4, in Brain Endothelial Cells Regulates Monocyte Transmigration," *Endothelium*, 14:25-34 (2007).
Kovacs et al., "microRNAs in Early Diabetic Retinopathy in Streptozotocin-Induced Diabetic Rats," *IOVS*, 52(7): 4402-4409 (2011).
Lum et al., "Inflammatory stress increases receptor for lysophosphatidylcholine in human microvascular endothelial cells," *Am. J. Physiol. Heart Circ. Physiol.*, 285: H1786-H1789 (2003).
Lum et al., "Protein phosphatase 2B inhibitor potentiates endothelial PKC activity and barrier dysfunction," *Am. J. Physiol. Lung. Cell. Mol. Physiol.*, 281: L546-L555 (2001).
Mendell, "miRiad Roles for the miR-17-92 Cluster in Development and Disease," *Cell*, 133:217-222 (2008).
O'Donnell et al., "Loss of p120 catenin upregulates transcription of proinflammatory adhesion molecules in human endothelial cells," *Microvasc. Res.*, 82(2): 105-112 (2011).
Qiao et al., "Lysophosphatidylcholine impairs endothelial barrier function through the G protein-coupled receptor GPR4," *Am. J. Physiol. Lung Cell. Mol. Physiol.*, 291: L91-L101 (2006).
Qiao et al., "PKA inhibits RhoA activation: a protection mechanism against endothelial barrier dysfunction," *Am. J. Physiol. Lung. Cell Mol. Physiol.*, 284: L972-L980 (2003).
Vandesompele et al., "Accurate normalization of real-time quantitative RT-PCR data by geometric averaging of multiple internal control genes," *Genome Biology*, 3(7):1-12 (2002).
Xu et al., "MicroRNA (miRNA) Tanscriptome of Mouse Retina and Identification of a Sensory Organ-specific miRNA Cluster," *J. Biol. Chem*, 282(34): 25053-25066 (Aug. 2007).
Search Report and Written Opinion issued in Int'l App. No. PCT/US2011/063400 (2012).
U.S. Appl. No. 13/907,399, filed May 31, 2013.

*Primary Examiner* — Ekaterina Poliakova-Georgantas
(74) *Attorney, Agent, or Firm* — Barnes & Thornburg LLP; Alice O. Martin

(57) ABSTRACT

Methods and compositions are disclosed to identify plasma and vitreous microRNA (miRNA) signatures of diabetic retinopathy (DR), and then as diagnostic biomarkers for the onset and progression of DR.

4 Claims, 31 Drawing Sheets

| miRNAs | Normal | STZ |
|---|---|---|
| rno-let-7b | 5.7 | 8.0 |
| rno-let-7c | 5.3 | 6.0 |
| rno-let-7d | 7.4 | 7.8 |
| rno-let-7e | 5.7 | 6.5 |
| mmu-let-7g | 7.9 | 8.9 |
| rno-let-7i | 6.6 | 6.6 |

| miRNAs | Fold of change (DR/ctr) | p |
|---|---|---|
| rno-let-7b | -4.9 | 5.8E-07 |
| rno-let-7c | -1.6 | 2.3E-04 |
| rno-let-7e | -1.7 | 1.6E-03 |
| mmu-let-7g | -2.0 | 5.0E-05 |

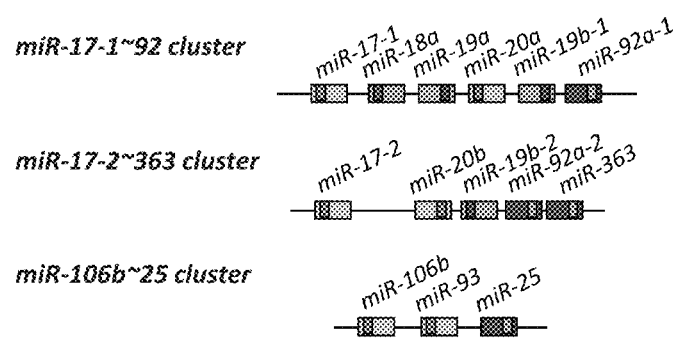
FIG. 13A
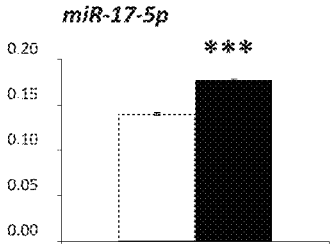
FIG. 13B
FIG. 13C
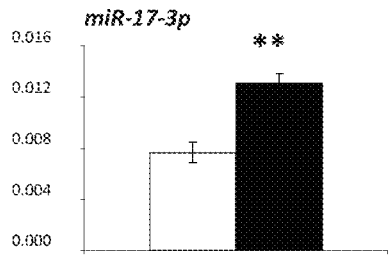
FIG. 13D
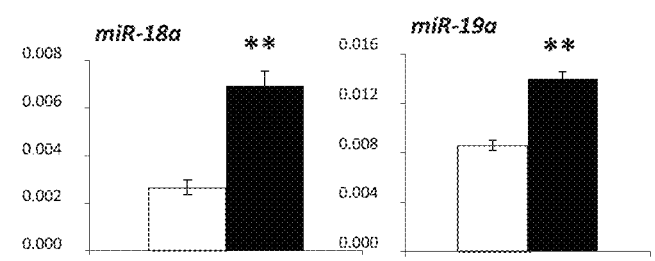
FIG. 13E
FIG. 13F

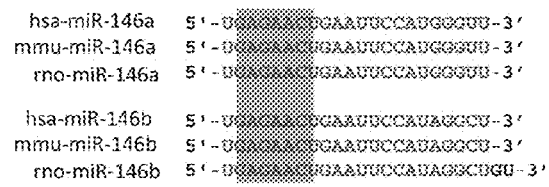
FIG. 15A
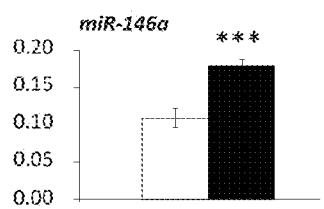
FIG. 15B
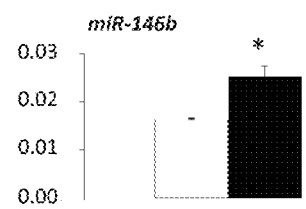
FIG. 15C
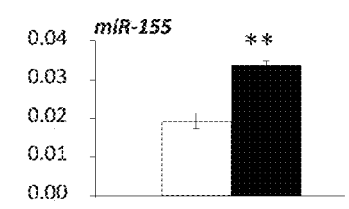
FIG. 15D
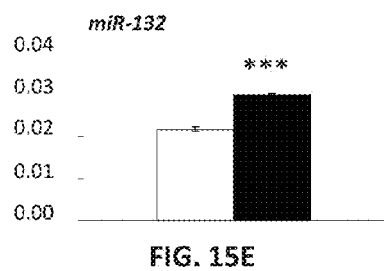
FIG. 15E
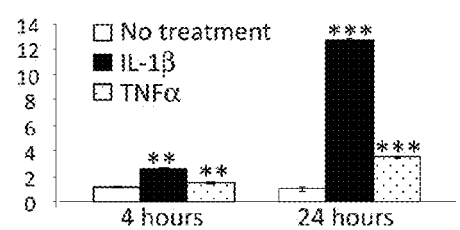
FIG. 15F
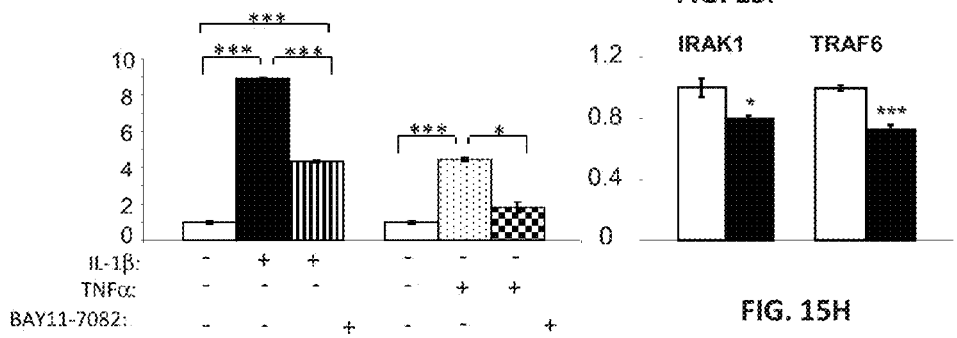
FIG. 15G
FIG. 15H

```
Nt291-314 of human CARD10 3'UTR 5'...CUCGCCCUGGAGUCU-GUUCUCAC... 3'
Nt265-287 of mouse CARD10 3'UTR 5'...CACACCCUGGAAUAGAGUUCUCA... 3'
Nt315-337 of rat CARD10 3'UTR   5'...CUCACCCUGGAAUAGAGUUCUCA... 3'
                                       || |||||| |||||||
                    hsa-miR-146a 3'...UUGGGUACCUUAAGUCAAGAGU... 5'
                    hsa-miR-146b 3'...UCGGAUACCUUAAGUCAAGAGU... 5'
```
FIG. 20A
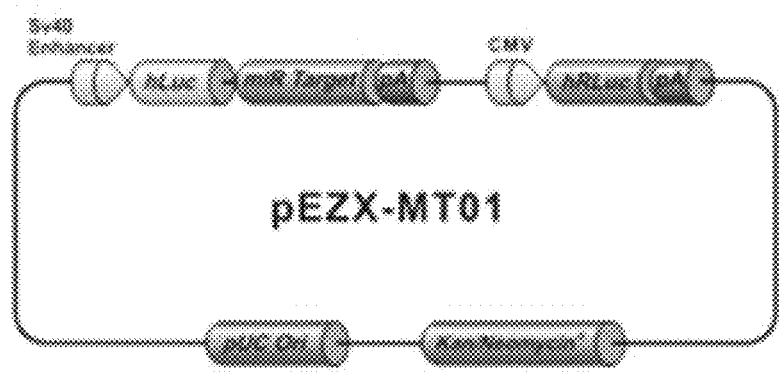
FIG. 20B
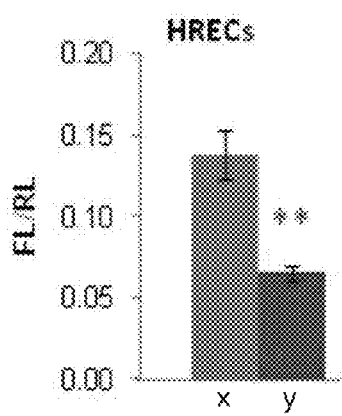
FIG. 20C
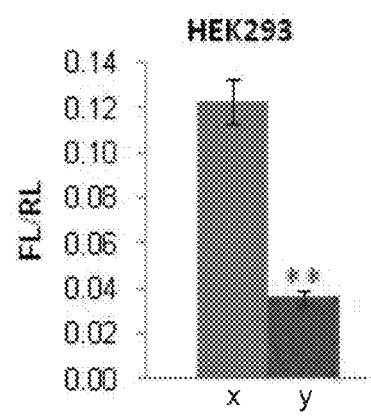
FIG. 20D

*: p<0.05; : p<0.01; *: p<0.001; ****: p<0.0001 x : no treatment;  y: IL-1β+scrambled oligos in B, or Bay11-7082 + IL-1β in C;
z : IL-1β+miR-146a mimics in B, or IL-1β alone.

MICRORNAS AS NEW THERAPEUTIC TARGETS FOR THE PREVENTION AND/OR TREATMENT OF RETINOPATHY

CROSS REFERENCE TO RELATED APPLICATIONS

This application is a Divisional of copending U.S. patent application Ser. No. 13/907,399 filed May 31, 2013, which is a Continuation-in-Part of International Application No. PCT/US2011/063400, filed Dec. 6, 2011, which claims the benefit of priority to U.S. Provisional Application No. 61/420,201, filed Dec. 6, 2010. The referenced applications are herein incorporated by reference in their entireties.

SEQUENCE LISTING

The instant application contains a Sequence Listing which has been submitted in ASCII format via EFS-Web and is hereby incorporated by reference in its entirety. Said ASCII copy, created on Apr. 26, 2017, is named 259224_Rplcmt_SEQ_ST25.txt and is 18,274 bytes in size.

BACKGROUND

MicroRNA (miRNA) expression profiling in the retina, retinal endothelial cells (RECs) and vitreous humor of streptozotocin (STZ)-induced diabetic rats are described herein for the first time and compared to profiling in non-diabetic rats. A number of miRNAs that are involved in multiple pathological pathways of diabetic retinopathy (DR) were identified in the retina and REC for use as therapeutic targets for the treatment of diabetic retinopathy (DR), and in the vitreous humor for use as biomarkers for diagnosis of DR and personalized medicine.

DR is the leading cause of blindness in the industrialized world in people between the ages of 25 and 74. Nearly all individuals who have had type I diabetes for more than 15 years develop DR. Approximately 50-80% of type II diabetic patients also develop retinopathy after 20 years of diabetes. DR is a result of interplays of multiple pathogenetic processes caused by hyperglycemia and abnormalities of insulin signaling pathways, including retinal microvascular dysfunction, abnormal inflammatory responses, and neuroretinal dysfunction and degeneration. In diabetic patients, hyperglycemia induces increased production of reactive oxygen species (ROS), formation of advanced glycation end-product (AGE), flux through polyol and hexamine pathways and activation of protein kinase C, and results in early reduction of retinal blood flow, leukostasis, vaso-occlusion, proinflammatory responses, endothelial-cell (EC) death, pericyte and vascular smooth muscle drop-out and microaneurysms, leading to a breakdown of the blood-retina barrier (BRB) and increased permeability. Early damage to retinal microvasculature plays pivotal roles in the development of DR. Leakage of fluid into the central retina results in diabetic macular edema and ischemic hypoxia, which promotes neovascularization in the attempt to restore blood flow. The newly-formed vessels may destroy normal retinal architecture and cause bleeding in the eyes and, ultimately, impair vision. Laser coagulation treatment is still the mainstay in management of DR, however, it may break down the BRB and worsen macular edema. Although significant progress has been made involving blocking the activity of vascular endothelial growth factor (VEGF) and pancreatic islet transplantation, the long-term effects of these treatments need to be evaluated, and other approaches to the treatment still are to be explored.

Although originally identified as a regulator of κB light chain expression in mature B and plasma cells, NF-κB has been shown to be expressed in almost all cell types, mediating responses to a remarkably diverse external and internal stimuli. NF-κB is a pivotal element of wide-range basic cellular functions, including proliferation, differentiation, survival and migration; and physiological and pathological processes, including inflammation, immunity, angiogenesis, stress response, neurogenesis, neural plasticity, learning and memory. Dysregulation of NF-κB pathways plays important roles in inflammatory and immune defects and related diseases, including autoimmunity, diabetes and its microvascular complications, atherosclerosis, as well as neurodegenerative diseases, and cancer development.

Numerous pathways lead to the activation of NF-κB, including G-protein couple receptor (GPCR)-mediated NF-κB activation. GPCRs have a characteristic seven-transmembrane-domain structure, and constitute one of the largest families of cell surface receptor proteins. GPCRs are expressed in all organ systems throughout the body, and transduce diverse extracellular signals, including hormones, neurotransmitters, light, odorants, tastants, chemokines and calcium, playing pivotal roles in wide-range biological functions. Many GPCR ligands, including thrombin, lyso-phosphatidic acid (LPA), angiotensin II, endothelin-1 (ET-1), platelet activating factor (PAF), IL-8 (CXCL-8) and stromal cell-derived factor (SDF; or CXCL12), etc, induces NF-κB activation, promoting inflammatory reactions and other cellular functions in many cell types and organ systems. GPCR engagement with ligands initiates intracellular recruitment of heterotrimeric guanine nucleotide-binding proteins (G-proteins) to the receptors. G proteins consist of three subunits, the Gα subunits, which responsible for GTP/GDP binding and GTP hydrolysis, and β and γ subunits (Gβ/γ). Activated G proteins induce PKC-involved signal transduction pathways, which converge to IKK and NF-κB activation. Caspase-recruitment domain (CARD)-containing scaffold/adaptor proteins, Caspase Recruitment Domain family member 10 (CARD10) and B-cell lymphoma 10 (Bcl10), and caspase-like protein mucosa-associated lymphoid tissue lymphoma translocation protein 1 (MALT1) have been shown to form CARD10-Bcl10-MALT complex and mediate GPCR-induced NF-κB activation between PKC and IKK and NF-κB activation.

microRNAs (miRNAs) are small, non-coding, regulatory RNAs, and represent a newly-recognized level of gene-expression regulation. It is estimated that there are more than 800-1000 miRNAs in the human genome and that more than one-third of the protein-coding genes in the human genome are subjected to miRNA regulation. Defects in miRNA biogenesis and mutations in miRNAs and the target sites of their downstream target mRNAs may cause diseases in animals and humans. miRNAs have been shown to be involved in many aspects of NF-κB activation pathways. miR-146 is shown to be induced by a variety of microbial components and proinflammatory cytokines in NF-κB-dependent manner, and in turn, miR-146 inhibits interleukin 1 receptor (IL-1R)/Toll-like receptor (TLR)-mediated NF-κB activation pathway by targeting two key adaptor molecules of this pathway, IL-1 receptor-associated kinase 1 (IRAK1) and TNF receptor-associated factor 6 (TRAF6), in monocytes, suggesting a novel mechanism of negative feedback regulation on IL-1R/TLR-mediated NF-κB activation. The roles of miRNAs in DR, DR patients and diabetic animal models are not established.

In spite of these reports, roles of miRNAs in GPCR-mediated NF-κB activation are still unknown.

SUMMARY

Micro RNAs are described herein as diagnostic biomarkers for diabetic retinopathy, and indicators of individualized therapy for diabetic retinopathy. Suitable microRNAs for use as biomarkers include those listed in Table 8. The differentially expressed miRNAs in the vitreous humor are miRNA signatures and diagnostic biomarkers for the prediction and diagnosis of diabetic retinopathy. Diagnostic biomarkers are useful in personalized medicine and are a top priority of diabetic research.

The differentially expressed miRNAs in the retina and RECs are new therapeutic targets for the treatment of DR.

Methods and compositions are disclosed herein to identify vitreous microRNA (miRNA) signatures of diabetic retinopathy (DR), for use as diagnostic biomarkers for the onset and progression of DR. miRNAs serve as molecular diagnostic biomarkers to evaluate real-time pathological changes in the eyes of diabetic retinopathy patients, to guide individualized treatment, and monitor the effects of drug treatment.

Vitreous transcript transcriptomes of miRNA are useful as diagnostic markers for diabetic retinopathy. The first miRNA transcriptomes of the retinas and RECs of STZ-induced diabetic rats and normal controls were found three months after the onset of diabetes. miRNAs were identified whose expression levels changed significantly in the retinas and RECs of diabetic rats compared to normal controls. Many of the miRNAs found have known functions in cell proliferation, apoptosis, angiogenesis, leukostasis, and NF-κB-mediated inflammatory processes, providing the first direct evidence that miRNAs is involved in the pathogenesis of DR through modulating multiple pathogenetic pathways. For example, the negative feedback loop of NF-κB and miR-146a may function in RECs, and miR-146 is a therapeutic target for the treatment of DR through its inhibition on NF-κB activation in RECs. The various miRNAs obtained from various biological tissues are candidates for diagnosis, treatment plans and treatment.

NF-κB is a pivotal element of a wide range of basic cellular functions, e.g. proliferation and survival. Dysregulation of NF-κB activity causes and/or contributes to inflammatory and immune defects and related diseases, including oncogenesis. microRNAs are shown to modulate NF-κB pathway at different levels. miR-146 is recognized as a negative feedback regulator of the IL-1R/TLR-mediated NF-κB activation pathway. miR-146 is disclosed herein to also have a negative feedback regulation on G-protein-couple receptor (GPCR)-mediated NF-κB activation through targeting key adaptor molecules of the pathway, CARD10, an important component of the CARD10-Bcl10-MALT1 signalosome, and TRAF6. Because CARD10-Bcl10-MALT1 signalosome is also employed by receptor tyrosine kinase (RTK)-mediated NF-κB activation, results described underscore a central, negative feedback regulatory role of miR-146 in multiple NF-κB activation pathways to maintain the homeostasis of endogenous NF-κB activity. The negative feedback regulatory loop between IL-1R/TLR-mediated NF-κB activation and miR-146 is active in endothelial cells (RCEs) and likely involved in the pathogenesis of DR.

CARD10, a key adaptor protein of GPCR-induced NF-κB activation pathway, is a target of miR-146. In human retinal endothelial cells (HRECs), thrombin induces the expression of miR-146a/b in a NF-κB-dependent manner; in turn, miR-146 inhibits thrombin-induced NF-κB activation and increases leukocyte adhesion to endothelial cells. In addition to modulating IL-1R/TLR-mediated NF-κB activation, miR-146 also has a negative feedback regulation on GPCR-mediated NF-κB activation through targeting CRAD10 in HRECs, expanding the roles of miR-146 in modulating NF-κB activation and related physiological functions, as well as disease processes.

Aspects of the present disclosure include the following methods and compositions:

Transcriptomes of microRNA are disclosed in the retina, retinal endothelial cells, and vitreous humor of mammalian eyes. Differently expressed MicroRNA transcriptomes in STZ-induced diabetic rats versus normal controls in the retina appear in Tables 4 and 5 as set forth in SEQ ID NOS: 1-19 and 20-36 respectively.

MicroRNA transcriptosomes in the vitreous humor of mammalian eyes, may be selected from Table 6 for normal eyes and Table 7 for diabetic eyes. MicroRNAs are useful as diagnostic biomarkers. For example, for diabetic retinopathy, e.g., for the prediction of individualized therapy for diabetic retinopathy.

MicroRNAs are obtained from the retina and from retinal endothelial cells and show differential expression as set forth in Tables 4 and 5 (SEQ ID NOS: 1-19 and 20-36, respectively); differentially expressed MicroRNAs from vitreous humor of STZ-induced diabetic rats versus normal control appear in Table 8 (SEQ ID NOS: 37-65, or their homologues).

A pharmaceutical composition including at least part of the transcriptomes of microRNA as shown in any of Tables 4, 5 or 8 (SEQ ID NOS: 1-19, 20-36, 37-65 respectively) is disclosed.

Transcriptomes of microRNA for example those selected from Tables 4 or 5 are useful in the treatment of diabetes-induced retinal vascular damage, diabetic retinopathy, or a combination thereof.

microRNAs selected for inhibition or treatment of diabetic retinoapathy include miR-34a/b/c selected to inhibit retinal neuronal and endothelial cell death, miR-146 a/b to inhibit NF-κB activation and inflammation, miR-31 to inhibit leukostatis and inflammation, miR-21 to help endothelial cell survival, let-7 to inhibit NF-κB activation, miR-17-3-p to inhibit leukostatis and miR-92 to block angiogenesis.

MicroRNAs may be obtained from blood, retina, retinal epithelial cells and vitreous humor of a mammal, wherein "determined" includes laboratory testing for microRNAs or obtaining the results of laboratory testing.

A method to inhibit diabetes-induced retinal vascular damage and diabetic retinopathy in a diabetic mammal including a human, the method including:
  a) selecting microRNAs that show differential expression between diabetic and normal mammals; and
  b) administering the selected microRNAs to the retina and retinal vasculature of the mammal.

The microRNAs inhibit NF-κB activation.

Suitable microRNAs are selected from the group consisting of miR-34a/b/c, miR-146, miR-155 (SEQ ID NO: 70), miR-31 (SEQ ID NO: 93), miR-21 (SEQ ID NO: 92), let-7 (SEQ ID NOS: 71-78), miR-17-3r and miR-92.

let-7 (SEQ ID NOS: 71-78) is suitable for administration to a retina and retinal vasculature of a diabetic mammal.

A method to provide individualized treatment of diabetic retinopathy in a mammal, including humans, includes:

a) determining the microRNA profile of the mammal; and
b) treating the mammal according to miRNA profile of the mammal; wherein the "determining" is in the vitreous humor of the mammal, and wherein "determined" includes laboratory testing for microRNAs or obtaining the results of laboratory testing.

BRIEF DESCRIPTION OF THE DRAWINGS

FIGS. 13A-J show expressions of members of the miR-17-1~92a and miR-17-2~92a clusters are significantly changed in retinal endothelial cells during the development of DR. (13A) Diagram of rat miR-17-1~92, miR-17-2~363 and miR-106b~25 clusters; the differentially shaded rectangular boxes represent the pre-miRNAs, in which the smaller boxes represent mature miRNAs (modified from Mendell JT, 2008). (13B) Sequence alignment of mature miRNA sequences (SEQ ID NOS 79-89, respectively, in order of appearance) groups members of these miRNA clusters into four groups, which were differentially shaded in (13A). The shaded rectangular box marks seed sequences of the miRNAs. (13C-J): Relative expression level of miR-17-5p (13C), miR-17-3p (13D), miR-18a (13E), miR-19a (13F), miR-19b (13G), miR-20a (13H), miR-20b (13I) and miR-92a (13J) by qRT-PCR (normalized to snRNA U6) of normal control (open bars. n=3) and STZ-induced diabetic rats (closed bars. n=3). Error bars represented as standard error of mean (sem). : $p<0.01$; *: $p<0.001$.

FIGS. 15A-K (15A) is a sequence alignment of human, mouse and rat miR-146a and miR-146b (SEQ ID NOS 96-101, respectively, in order of appearance); the sequences in the shaded box are seed sequences; (15B-E) Relative expression levels of miR-146a, (15B) miR-146b (15C), miR-155 (15D) and miR-132 (15E) in RECs of normal control (n=3) (open bars) and diabetic rats (n=3) (filled bars). (15E) Relative expression levels of miR-146a in rat TR-iBRB2 REC cells 4 and 24 hours after treatment with IL-1β (10 ng/ml) or TNFα (10 ng/ml) normalized to the ones in RECs without treatment. n=3, except that, for the no-treatment control condition, n=5. (15G) Relative expression levels of miR-146a in rat RECs treated with IL-1β and TNFα alone, or simultaneously treated with NF-κb inhibitor, Bay11-7082 (3 ng/ml). (15H-I): qRT-PCR analysis (15H) and Western blot analysis (15I) on relative expression levels of IRAK1 (15H and I) and TRAF6 (15H) in rat RECs transfected with miR-146a mimics (filled bars), or negative control mimics (open bars), 48 hours after transfection. n=3. qRT-PCR analysis on relative expression levels of ICAM-1 (15J) and MCP-1 (15K) in rat RECs transfected with miR-146a mimics or negative control mimics, followed by 24-hour treatment with IL-1β and TNFα. scr: negative control miRNA mimics with scrambled sequences. *: p<0.05; : p<0.01; *: p<0.001.

FIGS. 20A-D miR-146 targets CARD10 through a conserved target site in the 3'UTR of the CARD10 gene. (20A) Sequence alignment of conserved predicted target sites in 3'UTR of human, mouse, and rat CARD10 genes (SEQ ID NOS 106-108, respectively), with human mature rsa-miR-146a/b (SEQ ID NOS 109-110, respectively); the shaded sequences are the seed sequences of miR-146a/b. The highlighted nucleotides are conserved residues among human, mouse and rat, the ones in bold are same between mouse and rat. The nucleotides of miR-146 complementary to its target sequences are marked by vertical bars. *: residues mutated to AAA in the mutant form of the luciferase reporter construct; (20B) Luciferase target reporter vector, pEZX-MT01 (Genecoepoeia); in this construct, the miRNA target sequence is subcloned 3' of a firefly luciferase cassette (hLuc). A Renila luciferase cassette (hRLuc) driven by CMV promoter is used as normalization control. The entire 3'UTR sequence of the human wild type CARD10 gene (810 nt. NM_014550.3), was subcloned including the target site for miR-146 (20A) into the pEZX-MT01 as a wild type luciferase reporter construct; to test the specificity of this target site, 3 nucleotides were mutated, which are complementary to the first three nucleotides of the seed sequences of has-miR-146, from CUC to AAA [* in (20A)], and subcloned into the pEZX-MT-01 as a mutant construct; Luciferase reporter assays in human retinal endothelial cells (HRECs) (20C) and HEK293 cells (ATCC) (20D); Luciferase reporter constructs were co-transfected with miR-146a mimics using RNAiMax lipofectamine transfection agents (Invitrogen); 48 hours after transfection, cells are harvested for dual luciferase assays (Genecopoeia); Firefly luciferase activity (FL) is normalized by the Renila luciferase activity (RL). **: p<0.01. n=3. x: mutant. y: wild type.

(22A) two predicted target sites for miR-146; (FIG. 22A discloses SEQ ID NOS 111-126, respectively, in order of appearance)

(22B) reduced FL activity.

(22C) and (22D) miR-146a inhibits endogenous CARD10 in HRECs at both mRNA (22C) and protein levels (22D) by qRT-PCR (22C) and Western blot analyses (23D). n=3.***: p<0.001.

FIGS. 23A-F show that thrombin induces miR-146 expression through NF-κB activation in HRECs. (23A-E) Thrombin induced expression of miR-146a (23A) and miR-146b (23B) and NF-κB downstream genes (CAM1, MCP1 and VCAM1) (23C-E) in HRECs. (23F) NF-κB specific inhibitor, Bay11-7082 blocked thrombin induced upregulation of miR-146a/b.: no treatment control; thrombin.5 IU/ml; Bay11-7082 (3 mM)+thrombin (5 IU/ml). *: p<0.05, *: p<0.001; **: p<0.001. n=3.

FIGS. 24A-D show the results of overpression of CARD10. Overexpression of miR-146a inhibited thrombin-induced upregulation of NF-κB downstream genes and leukocyte adhesion to HRECs in vitro. (24A, B) qRT-PCR analysis of NF-κB downstream genes VCAM-1 (24A) and ICAM-1 (24B) on HRECs transfected with miR-146a mimics or negative control oligos with scrambled sequences for 24 hour followed by thrombin treatment (5 IU/ml) for 4 hours. n=3. (24C, D) leukocyte adhesion analysis; (24C) intensity of fluorescence intensity from Calcein-labeled adherent leukocytes; (24D) Numbers of Calcein-labeled leukocytes adherent on HREC monolayer after stringent washing. *p<0.05; **: p<0.01.

Figure 25:
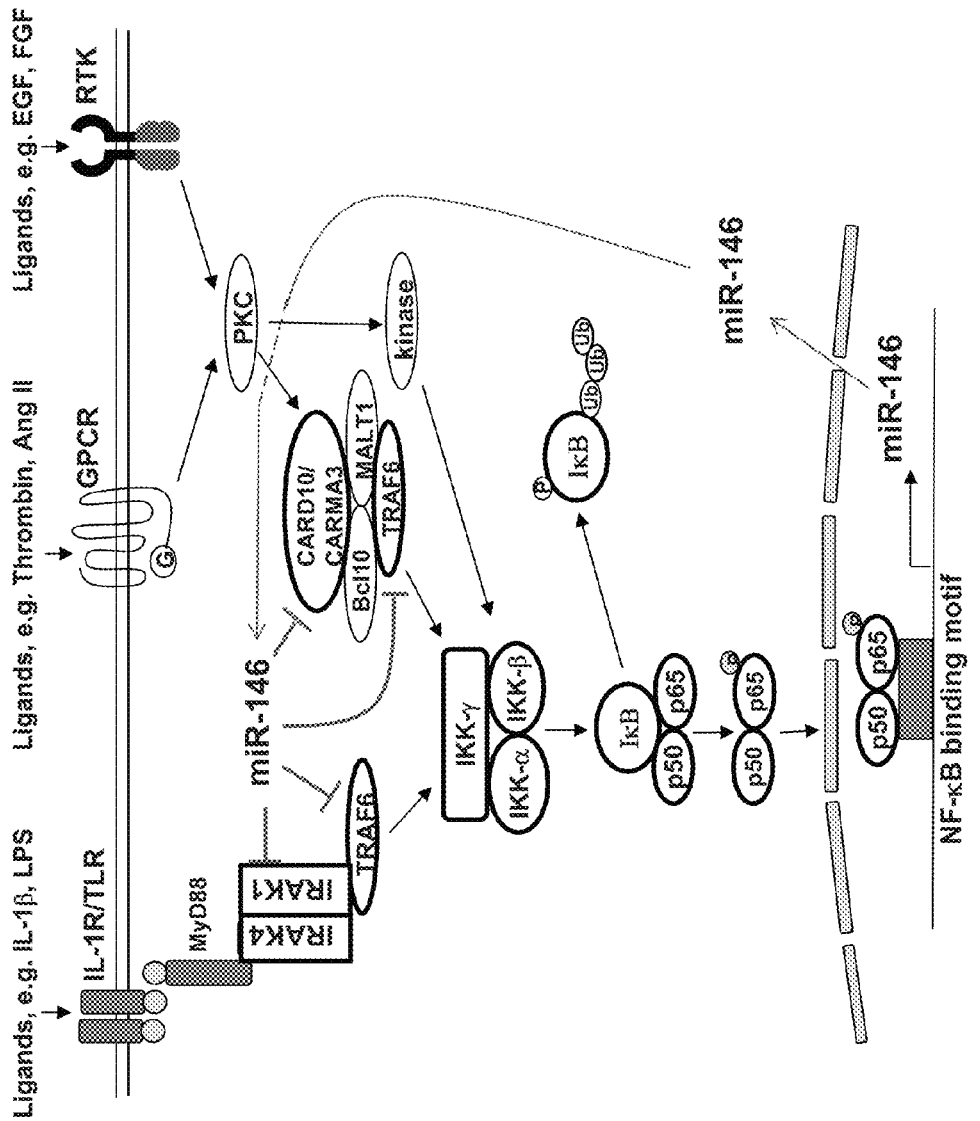

FIG. 25 illustrates negative feedback regulation on a IL-1R/TLR-, G-protein coupled receptor (GPCR)-, and Receptor Tyrosine Kinase (RTK)-mediated NF-κB activation by miR-146.

Figure 26A:
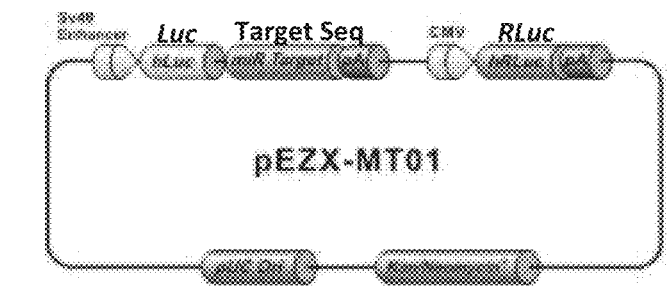
Figure 26B:
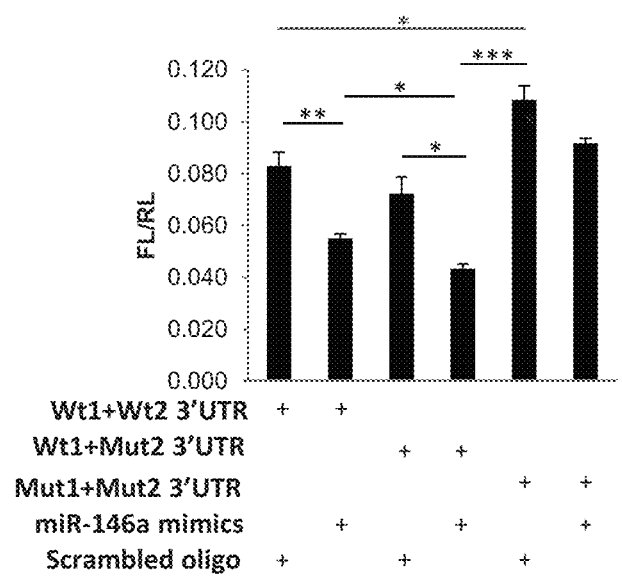

FIGS. 26A-B presents a target luciferase assay; (26A) targeting luciferase reporter construct in pEZX-MT01 vector (Genecopoeia); (26B) Luciferase reporter assays in HEK293 cells. *: p<0.05; : p<0.01; *p<0.001.

Figure 27A:
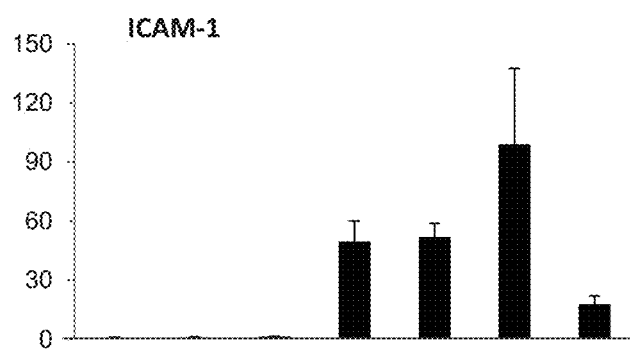
Figure 27B:
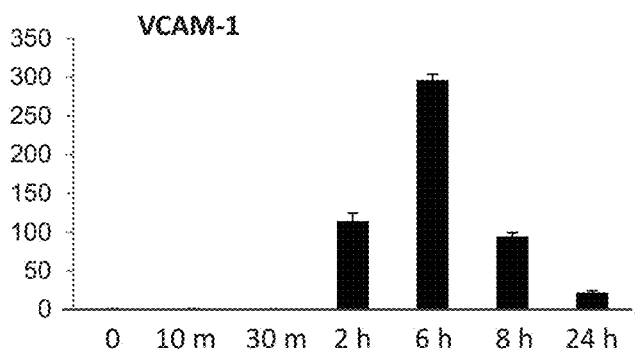
Figures 28A, 28B:
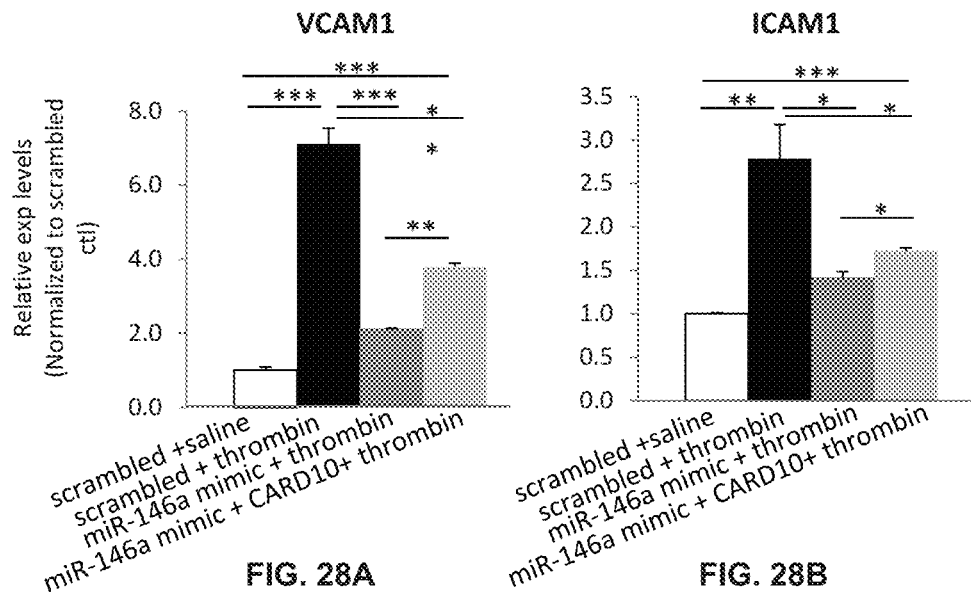
Figures 28C, 28D:
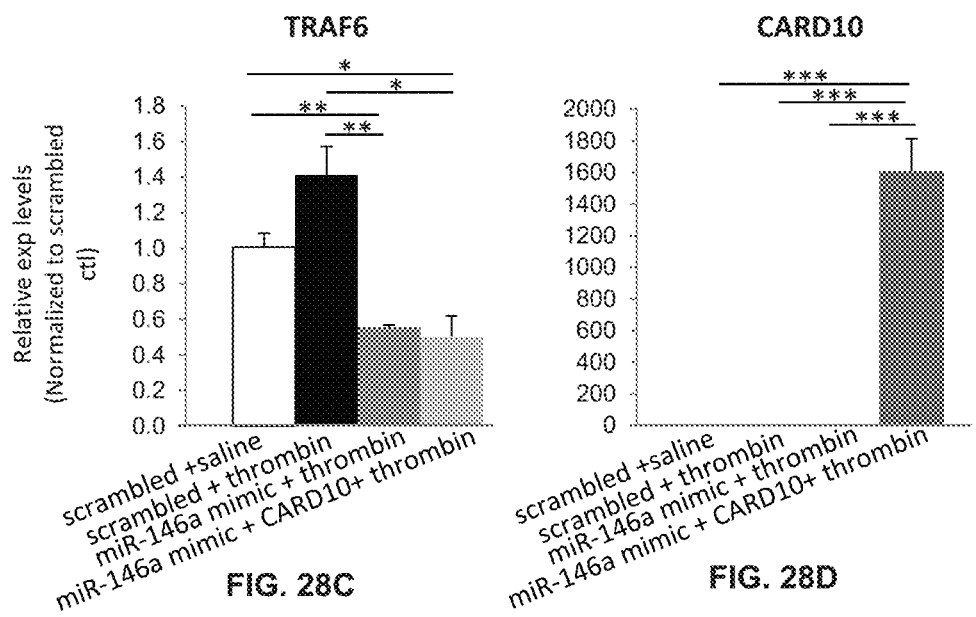

FIGS. 27A-B show time course the expression levels of NF-κB downstream genes, ICAM1 (27A) and VCAM1 (27B) after thrombin treatment (5 IU/ml) compared to time 0. m: minutes; h: hours. : p<0.01; *: p<0.001; **: p<0.0001; ***: p<0.00001.

FIGS. 28A-D illustrates hat miR-146 inhibits thrombin-induced NF-κB activation through targeting CARD10; qRT-PCR analysis on NF-κB downstream genes, VCAM1 (28A) and ICAM1 (28B) as well as adaptor proteins of the GPCR-mediated NF-κB activation pathway, TRAF6 (28C) and CARD10 (28D).

Figure 29:
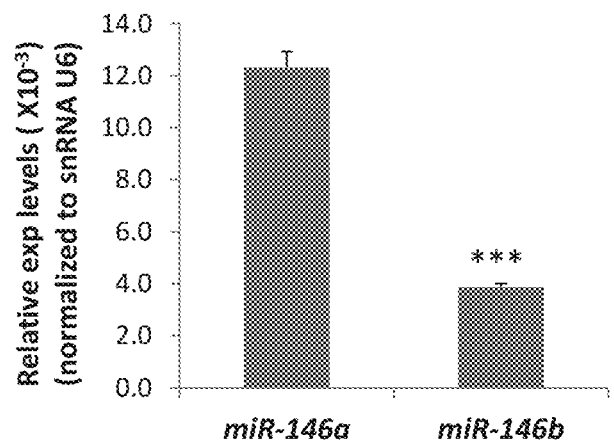
Figure 30A:
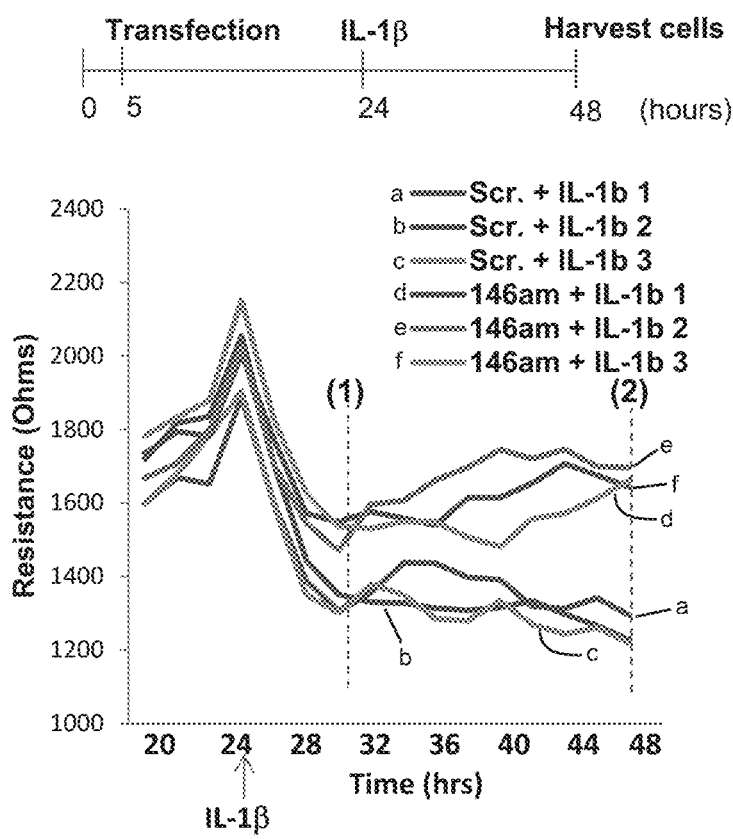
Figure 30B:
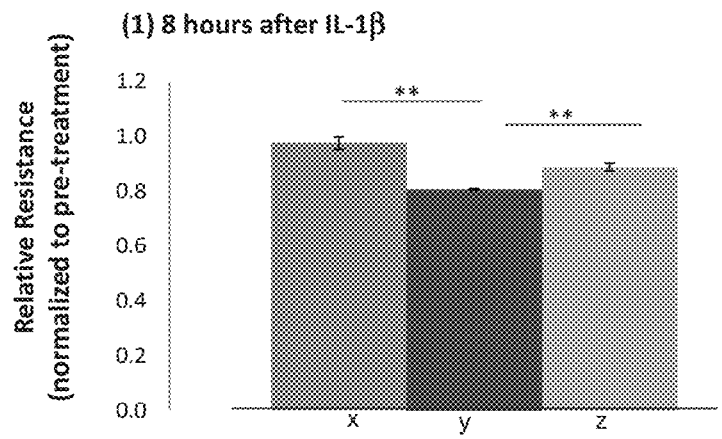
Figure 30C:
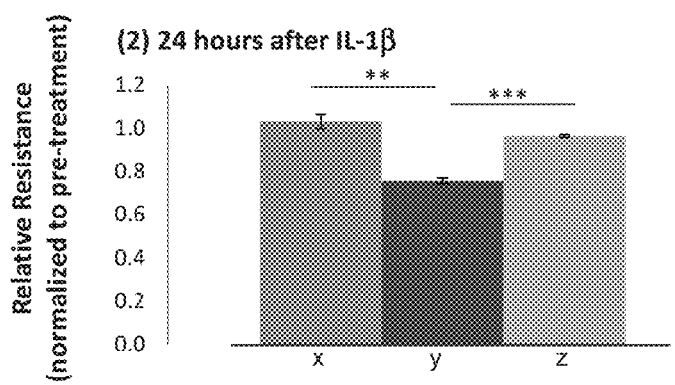
Figure 30D:
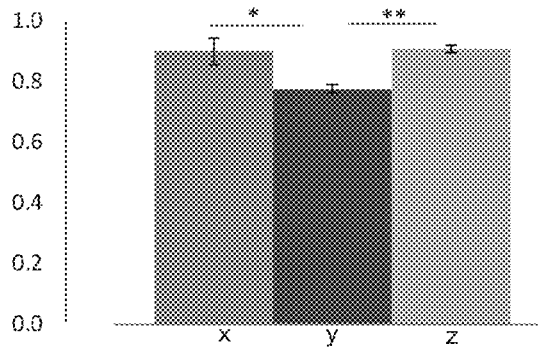

FIG. 29 presents endogenous expression levels of miR-146a and miR-146b in HRECs (normalized to snRNA U6). ***p<0.001.

FIGS. 30A-D show overexpression of miR-146a inhibits IL-1β-induced decrease of trans-endothelial electric resistance (TEER): (28A) experimental timeline and TEER curves; HRECs are transfected with miR-146a mimics (d, e, f) or scrambled oligonucleotides (a, b, c) (10 nM) as negative control; TEER was recorded from 20 hours after the start of the experiment; at 24 hours, the cells were treated with IL-1b (10 ng/ml); normalized TEERs show that overexpression of miR-146a prevented IL-1b induced decrease of TEER; normalized TEER 8 hours (1) (30B) and 24 hours (2) (30C) after the addition of IL-1b;] (30D) the effect of IL-1β on TEER is a result of NF-κB activation; the cells were treated with NF-κB inhibitor, Bay11-7082, 1 hour prior to IL-1b treatment. Bay11-7082 treatment prevented IL-1b induced decrease of TEER. : p<0.01; *: p<0.001.

DETAILED DESCRIPTION

Micro RNA (miRNA)-expression profiling was performed in the retina, retinal endothelial cells (RECs), and vitreous humor of streptozotocin-induced diabetic and normal control rats. 354 and 355 miRNAs in the retina, 221 and 216 miRNAs in RECs, and 236 and 279 in the vitreous humor were detected in control and diabetic rats, respectively. Furthermore, at least 86, 120 and 69 miRNAs were identified that are differentially-expressed (p<0.01) in the retina, RECs and vitreous humor of the diabetic rats compared to normal controls, respectively. Functional annotation analysis indicated that the differentially expressed miRNAs may be involved in multiple pathogenetic pathways of diabetic retinopathy (DR), including leukostasis and inflammation, endothelial integrity and angiogenesis, and cellular proliferation and apoptosis. In addition, negative feedback regulation of miR-146 on NF-κB activation may function in RECs. Micro RNAs such as miR-146 are alternative therapeutic targets for the treatment of DR through inhibition on NF-κB activation in RECs.

I. miRNAs in the Vitreous are New Diagnostic Biomarkers of DR.

Isolation of vitreous RNA from STZ-induced diabetic and normal control rats: 2 weeks after STZ-induced diabetes, 3 diabetic and 3 normal control rats were sacrificed and their eyeballs harvested. In cold PBS, the eyeballs were dissected to collect the vitreous bodies, the retinas and the lens, total RNA was prepared using the mirVana miRNA isolation kit (Ambion). The yield of total RNA from vitreous body was ~764 ng and 1125 ng total RNA/vitreous of control and diabetic rats, respectively.

miRNA expression profiling: The TaqMan rodent miRNA microarray_v2.0 (Applied Biosystems), which provides full coverage of all known mouse and rat miRNAs according to miRBase v10 (www.mirbase.org) on two microarray cards (A and B cards), was used for miRNA-expression profiling on vitreous RNA samples, according to manufacturer's manual.

miRNA transcriptomes of the vitreous body of normal control rats, were composed from 236 miRNAs. (Table 6) The miRNA-expression profiles of the vitreous body are different from that found in other tissues, suggesting the vitreous body has its own unique miRNA expression pattern. Vitreous miRNA transcriptomes have not previously been described. These vitreous miRNAs may play important roles in normal function of the vitreous, and may be involved in the pathogenesis of various retinal and eye diseases. Many of them are candidates for diagnostic biomarkers for various retinal and eye diseases.

A miRNA transcriptome of the vitreous body of streptozotocin (STZ)-induced diabetic rats was identified two weeks after the onset of diabetes, and includes 279 miRNAs (Table 7).

Figure 17A:
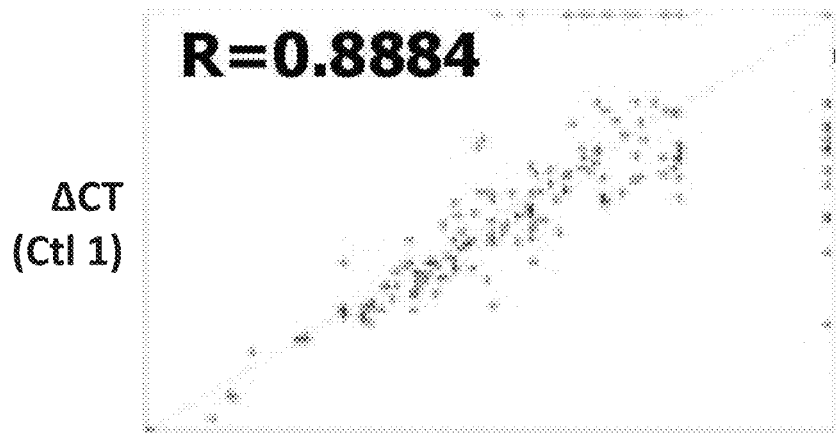
FIGS. 17A-C is an example of a scatter plot of vitreous miRNA profiles of two control rats (ctl); (17B) is a signal correlation plot; (17C) a heat map and Pearson's correlation plot of vitreous miRNA profiles of control and diabetic rats (STZ).
Figure 17B:
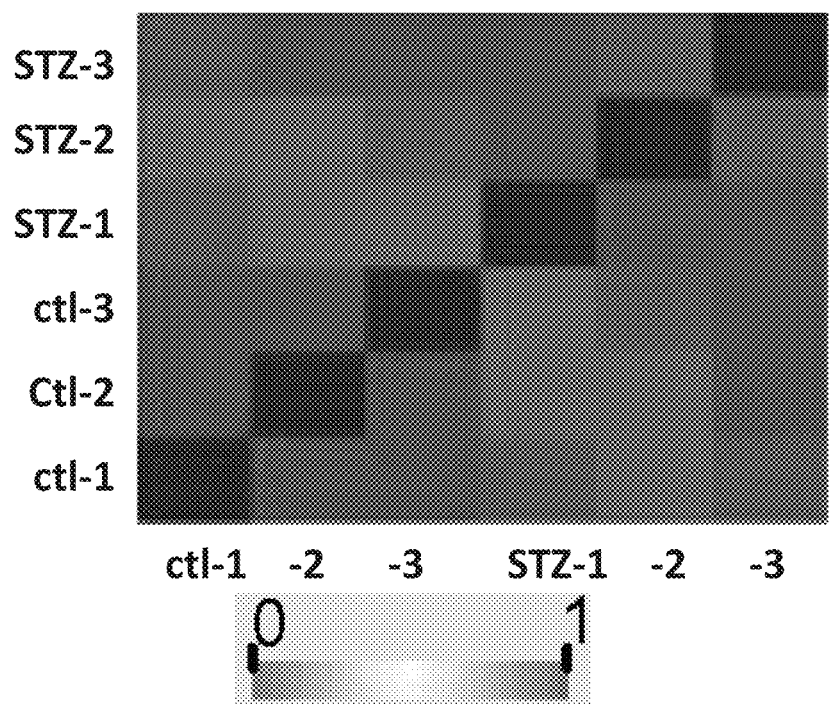
Figure 17C:
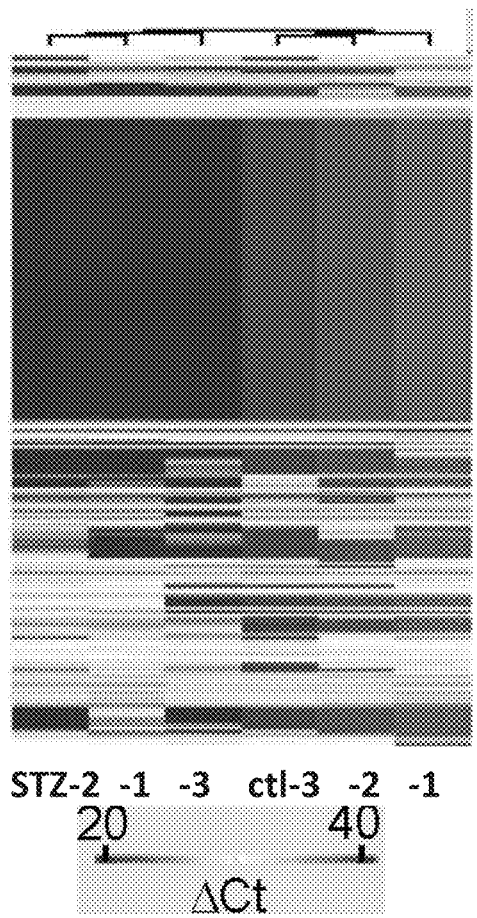
Figure 18A:
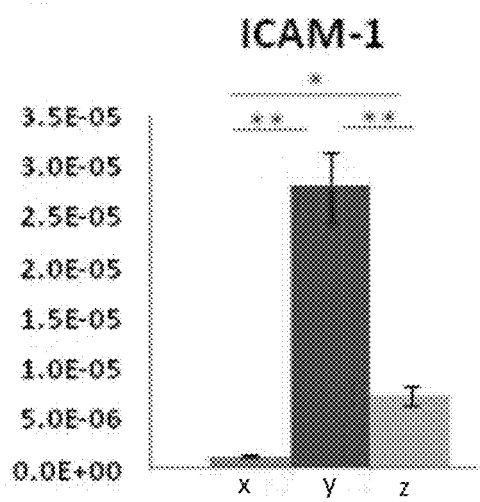
FIGS. 18A-D show quantitative RT-PCR analysis on the ICAM-1 (18A), MCP-1A (18B), IRAK1 (18C) and TRAF6 (18D) in retinal endothelial cells (HRECs); (18A-B) HRECs were transfected overnight with miR-146a mimics or scrambled oligonucleotides (10 nM), followed by 24-hour IL-1β (10 ng/ml); treatment in HRECs inhibited IL-1β-induced NF-κB downstream genes, ICAM-1 and MCP-1, (18C-D) Transfection of miR-146a mimics in HRECs down-regulated miR-146 target genes, TRAK1 and TRAFG. *: p<0.05; : p<0.01; *: p<0.001; ****: p<0.001. x: no treatment; y: IL-1b+scrambled oligos; z: IL-1B+miR-146a mimics.
Figure 18B:
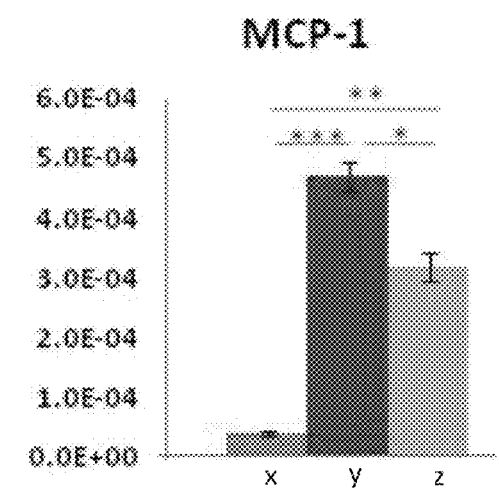
Figure 18C:
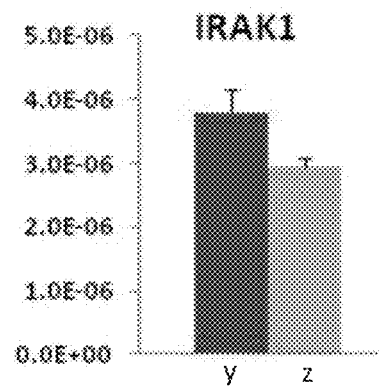
Figure 18D:
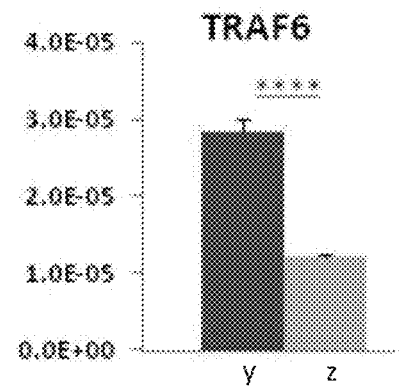

Scatter plots and signal correlation plots (FIGS. 17A and B) revealed that relative expression levels of individual miRNAs are consistent among different samples. Comparison to miRNA expression profiles of mouse retina and brain, and rat retina and RECs, revealed that, although having some similarities, the miRNA-expression profiles of the vitreous are different from other tissues, suggesting the vitreous has its unique miRNA expression pattern; 3) Correlation studies (FIGS. 17, B and C) showed that miRNA-expression profiles were consistently clustered by control or diabetic groups, suggesting that STZ-induced diabetes resulted in consistent changes of miRNA expression. This is a novel vitreous miRNA transcriptome.

By comparison to the miRNA transcriptome of normal control rats, At least 21 miRNAs are significantly upregulated and 8 miRNAs significantly downregulated (p<0.05) in the vitreous of STZ-induced diabetic rats compared to normal control (Table 8). Further analysis on the novel differentially expressed miRNAs revealed interesting features:

(a) Co-expressed miRNAs tend to change their levels of expression simultaneously, supporting that the variations observed are specific changes of miRNA expression during the development of DR: miR-96 and miR-182 are two members of the polycistronic, sensory-organ specific miR-183/96/182 cluster. miR-126-3p and miR-126-5p are derived from the same stem loop, so as miR-129-5p and miR-129-3p. These co-expressed miRNAs are increased in the vitreous of STZ-induced diabetic compared to normal control rats (Table 8);

(b) Endothelial specific miRNAs are increased, which may reflect early damage to RECs during the development of DR: In STZ-induced diabetic rats, retinal vascular permeability was shown to be significantly increased as early as 8 days after the onset of diabetes. miR-126-3p, an endothelial-cell-specific miRNA, which regulates VEGF signaling pathway, leukostasis, vascular integrity and angiogenesis' increased by ~3.7 folds in the vitreous of diabetic animals (Table 8). This significant increase may be a result of increased REC damage in early DR. (c) Neuroretina-specific miRNAs are increased, which may reflect early pathological damage to retinal neurons in early DR: members of the miR-183 cluster are among the highest expressed miRNAs in retinal neurons. Significant increase of miR-96 and miR-182 in the vitreous may be a result of increased damage and apoptosis of retinal neurons, since neuroretinal dysfunction is one of the earliest signs of DR, and neurodegeneration of the retina is a critical component of DR.

In summary, miRNA signatures of the vitreous of STZ-induced diabetic rats two weeks after diabetic onset may represent early pathological changes in both retinal microvasculature and retinal neurons, strongly supporting that miRNA signature in the vitreous are biomarkers for the diagnosis of DR.

II. miRNAs in the Retina and RECs are New Therapeutic Targets for Treatment of DR.

miRNA-expression profiling was done and miRNA transcriptomes were established of the retina of streptozotocin (STZ)-induced diabetic and normal control rats three months after the onset of diabetes. Retinal microvascular changes play pivotal roles in pathogenesis of DR. Retinal endothelial cells (RECs) were isolated from diabetic and normal control rats and miRNA profiling was done. By comparing these miRNA-expression profiles, a series of miRNAs were identified that were differentially expressed in the retina and RECs of diabetic rats compared to the ones of normal controls. Functional annotation studies revealed that these differentially-expressed miRNAs are involved in various functional pathways that are intimately related to pathogenesis of DR, e.g. leukostasis, inflammation, including NF-κB activation pathways, endothelial function, angiogenesis, apoptosis and cell-cycle regulation. Therefore miRNAs may contribute to the pathogenesis of DR at different levels. In vitro functional studies showed that various proinflammatory cytokines, including interleukin 1β (IL-1β) and tumor necrosis factor-α (TNFα), which are known to be increased in diabetic eyes, induced the expression of miR-146a in an NF-κB-dependent manner in RECs. Overexpression of miR-146a in RECs inhibited IL-1β-induced NF-κB activation through targeting key adaptor molecules, IRAK1 and TRAF6. Negative feedback regulation of miR-146 on NF-κB activation may function in RECs and miR-146 may potentially be used as a therapeutic target for the treatment of DR by inhibiting NF-κB activation in RECs. This is the first direct and in-depth investigation on miRNAs in DR in diabetic animal models, providing the first insights into the roles of miRNAs in the pathogenesis of DR.

miRNA-expression profiling in the retina and RECs of STZ-induced diabetic and normal control rats. Three months after the onset of STZ-induced diabetes, retinas of diabetic and normal control rats were harvested and miRNA-expression profiling was performed using TaqMan miRNA microarrays, which cover all rodent miRNAs (557 unique miRNAs) according to miRBase v10 (http://www.mirbase.org/). At least 354 miRNAs (63.6% of total unique rodent miRNAs) in the retinas of normal control rats and 355 miRNAs (63.7%) in the retinas of diabetic rats were found. (Tables 1 and 2). All of the miRNAs expressed in mouse retinas, except miR-219, were expressed in rat retinas with similar expression patterns, suggesting conservation of miRNA expression between mouse and rat. For example, all members of the sensory organ-specific miR-183/96/182 cluster and pan-neuronal specific miR-124 are highly expressed in both mouse and rat retinas. miRNAs previously reported to be expressed in rat retinas, including miRs-7,-23a, -29, -107, -135a, -135b, -143, -200b, -206, and let-7d, were all included in rat retinal miRNA transcriptomes.

miRNA-expression profiling in retinal endothelial cells of STZ-induced diabetic rats and normal controls. To uncover any involvement of miRNAs in diabetes-induced retinal microvascular changes, RECs were isolated from rat retinas using antibodies against platelet-endothelial cell adhesion molecule-1 (PECAM-1), an EC-specific surface antigen by a magnetic activated cell sorting system (MACS. Miltenyi Biotec) (FIG. 2), three months after the onset of STZ-induced diabetes, and miRNA expression profiling was performed on RECs using TaqMan miRNA microarrays. 221 and 216 miRNAs (~40% of all rodent miRNAs) are expressed in RECs of normal control and diabetic rats, respectively (Tables 1 and 3). Many known endothelial-specific or enriched miRNAs are significantly enriched in the miRNA transcriptomes of RECs. For example, endothelial specific miR-126-3p appeared to be the third and second highest expressed miRNA in the miRNA transcriptomes of RECs of both normal control and diabetic rats. Compared to its expression levels in the total retina, miR-126-3p showed at least 33-fold enrichment in RECs in normal control rats. Other miRNAs known to be highly expressed in human umbilical vein endothelial cells (HUVECs), e.g. miRs-15b, -16, -20, -21, -24, -29a, -31, -99a, -100, -103, -106, -125, -130a, -181a, -191, -222, -204, -320, and let-7b, also are highly expressed in rat RECs. Comparison to the miRNA-expression profiles of the total retina revealed that 52 (~24%) miRNAs in RECs showed significant, at least 2-fold enrichment in RECs, especially the ones that are highly expressed in RECs, suggesting their potential unique roles in RECs and retinal vascular functions.

miRNAs differentially expressed in the retinas and RECs of normal control and STZ-induced diabetic rats. miRNAs whose expression levels changed significantly during the development of DR may include those involved in the pathogenesis of the disease. To identify miRNAs differentially expressed in the retina and RECs of diabetic rats compared to normal controls, two pair-wise comparisons were made: 1) retinal miRNA transcriptomes of diabetic rats vs. normal controls; 2) REC miRNA transcriptomes of diabetic rats vs. normal control rats. The results revealed that expression levels of at least 80 miRNAs are significantly increased ($p<0.01$), while six miRNAs are significantly decreased ($p<0.01$) in the retinas of STZ-induced diabetic rats, compared to normal control rats (Tables 1 and 4). Among these, at least 19 miRNAs showed at least a two-fold increase in the retinas of diabetic rats, compared to normal controls; however, none of the downregulated miRNAs showed more than a two-fold difference. In RECs, at least 16 miRNAs are significantly upregulated, while 104 miRNAs showed significantly decreased expression in STZ-induced diabetic rats compared to normal controls ($p<0.01$) (Tables 1 and 5). Among these, nine and 79 miRNAs showed at least a two-fold change in STZ-induced diabetic rats compared to normal controls.

Verification of differentially-expressed miRNAs. To verify the findings in microarray analysis, qRT-PCR was performed on the top 14 most upregulated and all six downregulated miRNAs in the retinas of diabetic and normal control rats. The result showed that all of the top 14 most upregulated miRNAs in diabetic rats (miR-31, miR- 31*, miR-34b-3p, miR-34c, miR-184, miR-199a, miR-200a, miR-200b, miR-205, miR-223, miR-335-3p, miR-378*, miR-488 and miR-574-3p) are confirmed to be increased by qRT-PCR assays (Table 4). miR-335-5p and miR-378 are derived from the same stem loops as miR-335-3p and miR-378*, respectively, therefore miR-335-5p and miR-378 also may be upregulated. qRT-PCR assays were performed and confirmed this expectation (Table 4). Among the six down-regulated miRNAs in diabetic retinas in the microarray study, three of them, miR-20b, miR-499, and miR-690 are confirmed to be significantly decreased in the retinas of diabetic rats by qRT-PCR (Table 4), while miR-375 and miR-872 did not show significant difference, and miR-431 showed an increase in diabetic retinas compared to normal controls, a trend opposite to the one detected by microarray analysis.

In RECs, the top 15 most upregulated or downregulated miRNAs were selected for qRT-PCR confirmation. Eleven of the top 15 most upregulated miRNAs, including miR-15b, miR-19b, miR-21, miR-31, miR-132, miR-142-3p, miR-146a, miR-155, miR-339-5p, miR-342-3p, and miR-450a, were verified to be significantly increased in RECs of STZ-induced diabetic rats compared to normal controls (Table 5). Among these, miR-31 is significantly increased in both RECs and retinas of STZ-induced diabetic rats, compared to normal controls, suggesting potential important roles of this miRNA in the development of DR.

Figures 13G, 13H, 13I:
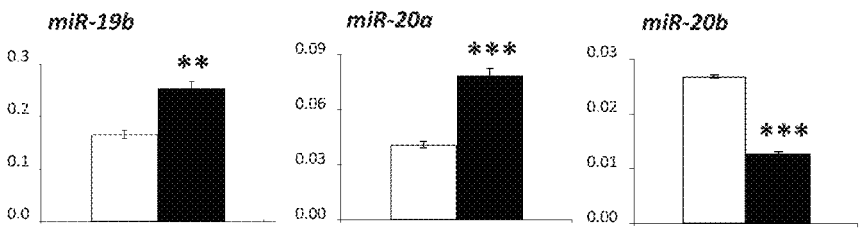
Figure 13J:
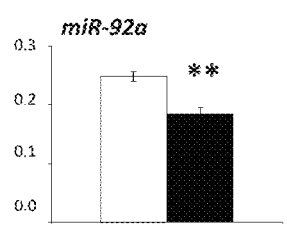
Figures 14A, 14B, 14C:
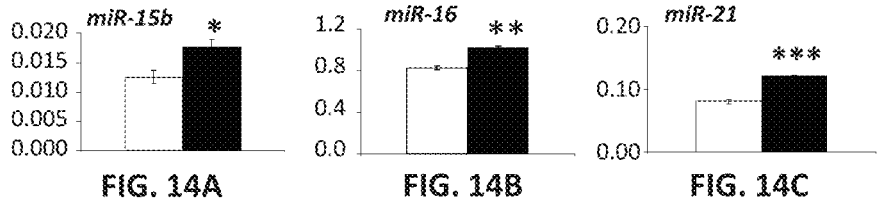
FIGS. 14A-H show expression of VEGF-responsive miRNAs and other miRNAs implicated to regulate angiogenesis. (14A-D): expression of miR-15b (SEQ ID NO: 90) (14A), miR-16 (SEQ ID NO: 91) (14B), miR-21 (SEQ ID NO: 92) (14C), and miR-31 (SEQ ID NO: 93) (14D) are significantly changed in RECs of diabetic rats, compared to normal controls; (14E-H): miR-31 (SEQ ID NO: 93) (14E), miR-184 (SEQ ID NO: 94) (14F), miR-378 (SEQ ID NO: 95) and miR-378* (SEQ ID NO: 95) (14 G and H) are significantly upregulated in the retina of diabetic rats, compared to the normal controls. *: p<0.05; : p<0.01; *: p<0.001.
Figures 14D, 14E, 14F:
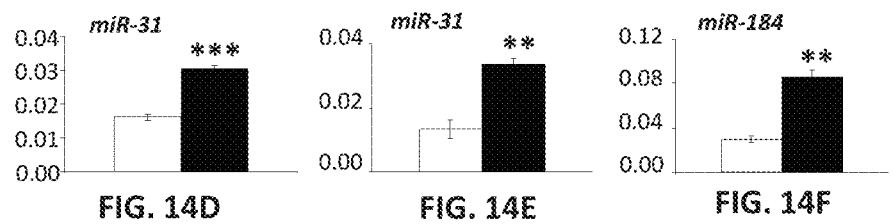
Figures 14G, 14H:
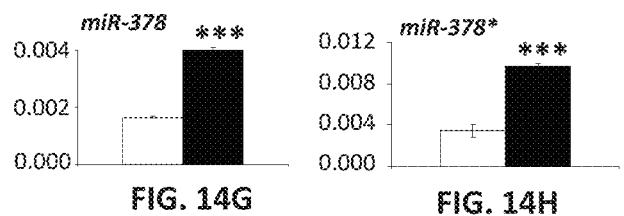
Figure 15I:
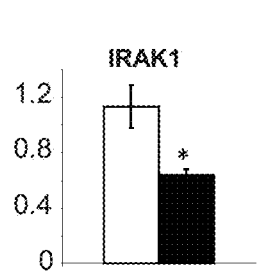
Figure 15J:
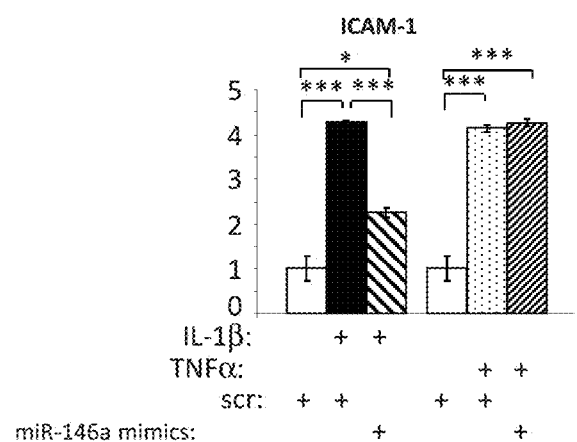
Figure 15K:
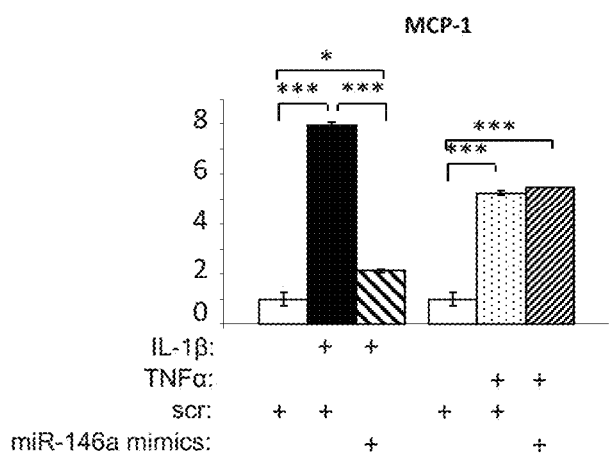
Figure 16A:
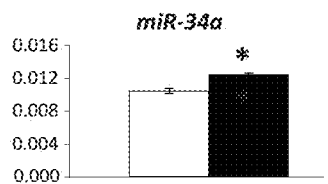
FIGS. 16A-H relate qRT-PCR analysis of relative expression levels of p53 (16E) and its downstream genes, p21 (16F) and members of the miR-34 family in the retina ("miR-34a," "miR-34b," "miR-34c," and "miR-34b-3p" disclosed as SEQ ID NOS 102-105, respectively) (16A-D) and RECs of normal control (open bars. n=3) and STZ-induced diabetic rats (closed bars. n=3). Error bars represented as standard error of mean (sem). *: p<0.05; : p<0.01; *: p<0.001. Expression levels of p53 and p21 were normalized to 18s rRNA, while the ones of miRNAs were normalized to snRNA U6.
Figure 16B:
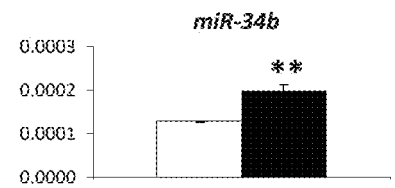
Figure 16C:
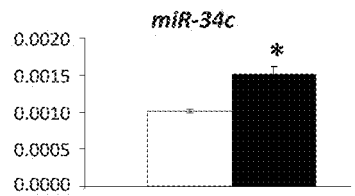
Figure 16D:
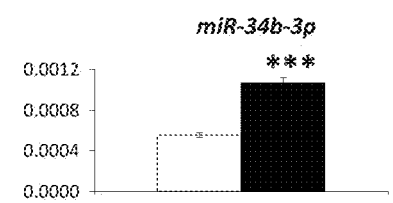
Figure 16E:
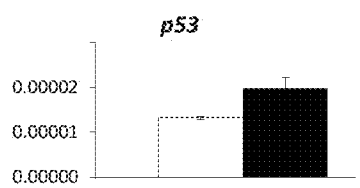
Figure 16F:
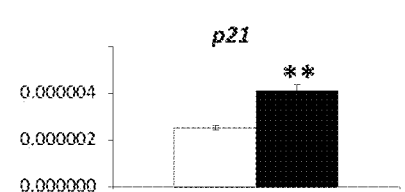
Figure 16G:
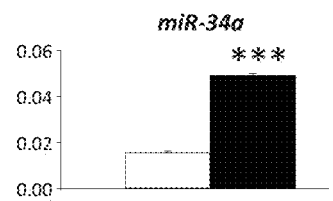
Figure 16H:
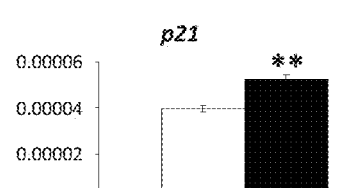

Five of the top 15 most downregulated miRNAs, including miR-20b-5p, miR-29c, miR-181c, miR-136*, and miR-376c, were confirmed to be significantly decreased in RECs of STZ-induced diabetic rats compared to normal controls (Table 5). miR-92a, which showed downregulation by 1.7-fold in RECs of diabetic rats by microarray study, has been reported to be highly expressed in human ECs and regulate angiogenesis (62). qRT-PCR analysis confirmed that miR-92a is significantly ($p=0.008$) decreased in RECs of diabetic rats compared to normal controls (Table 5 and FIG. 13).

Signatures of multiple pathogenic pathways: Although it is intriguing that most of the differentially-expressed miRNAs in total retina are upregulated in diabetic rats, while most of the differentially-expressed miRNAs in RECs are downregulated in diabetic rats, functional annotation analysis on the differentially-expressed miRNAs revealed that these miRNAs signify multiple pathogenetic pathways, which are known to play important roles in the development of DR, including leukostasis and inflammation, angiogenesis and microvascular functions, and cellular proliferation and apoptosis.

Figure 1A:
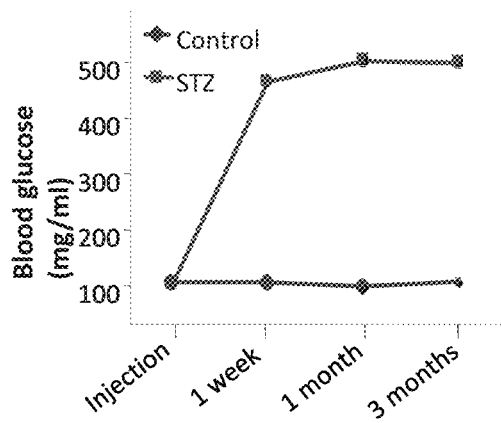
FIGS. 1A-B show blood glucose levels (1A) and body weight (1B) of Sprague-Dawley rats injected with STZ (n=23) and vehicle (n=27). The error bars are standard errors of the mean (s.e.m.)

1. Significant changes in miRNAs known to regulate cell-cycle progression, angiogenesis, and cell survival represent one of the most prominent miRNA signatures in RECs of STZ-induced diabetic rats.

a. Expressions of members of miR-17~92 and miR-106a~363 clusters are significantly changed in RECs during the development of Dr, suggesting their potential roles in the pathogenesis of DR. miR-17-1~92, miR-17-2~363, and miR-106b~25 clusters are conserved, paralogous miRNA clusters (FIG. 1A). Members of these paralogous clusters have been shown to function as oncogenes, modulating cell-cycle progression, apoptosis and angiogenesis in tumorigenesis as well as the normal development of various tissues. Among the confirmed differentially-expressed miRNAs in RECs (Table 5), miR-19b is a member of both the miR-17-1~92 and miR-17-2~363 clusters. However, miR-92a, another member of these two clusters, and miR-20b, a member of the miR-17-2~363 cluster, were both significantly downregulated (FIG. 1 and Table 3). qRT-PCR was performed on other members of these miRNA clusters. Similar to miR-19b, all members of the miR-17-1~92a cluster, except miR-92a, were significantly upregulated in RECs of STZ-induced diabetic rats compared to normal controls (FIG. 1C-J), supporting that the expression of the miR-17-1~92a cluster may be upregulated, while the miR-17-2~363 cluster may be downregulated in RECs of STZ-induced diabetic rats compared to normal controls. miR-17 and miR-92a can be derived from either the miR-17-1~92a cluster (17-1 and miR-92a-1) or the miR-17-2~363 cluster (miR-17-2 and miR-92a-2).

miR-93, a member of the miR-106b~25 cluster, was detected as increased in RECs of STZ-induced diabetic rats by microarray analysis; however, this change failed to be confirmed by qRT-PCR assays. Additionally, the other two members of this cluster, miR-106b and miR-25, did not show significant change in microarray analysis. These results suggest that expression of the miR-106b~25 cluster did not change significantly in RECs during the development of early DR.

In HUVECs, miR-17-5p, miR-18a and miR-20a are reported to be induced by VEGF, while miR-17-5p and miR-17-3p were shown to be induced by TNFα. Since both VEGF and TNFα are upregulated in diabetic retinas and play important roles in the pathogenesis of DR, upregulation of the miR-17-1~92a cluster in RECs of diabetic rats could be a result of increased expression of VEGF and TNFα in the retina. miR-18a and miR-19b are shown to promote angiogenesis, in part by targeting angiogenic inhibitors, thrombospondin (TSP-1) (73), and connective tissue growth factor (CTGF). miR-92a is reported to block angiogenesis by targeting mRNAs corresponding to several pro-angiogenic genes, including integrin subunit α5 (ITGA5), which plays important roles in vascular development, endothelial-cell migration, and angiogenesis. In addition, recently miR-17-3p was shown to inhibit neutrophil adhesion to ECs in vitro through targeting intercellular adhesion molecule (ICAM)-1 (69), which plays important roles in leukostasis, one of the earliest changes during the development of DR. Therefore, members of the miR-17-1~92a and miR-17-2~363 clusters may be involved in the pathogenesis of DR through its modulation on leukostasis and angiogenesis. Upregulation of miR-18a and miR-19b, and downregulation of miR-92a in RECs of diabetic rats (FIG. 1) may promote angiogenesis and represent a response of RECs to increased cell death of REC in early DR. Increased expression of miR-17-3p in RECs of diabetic rats may represent the attempt of RECs to decrease their cell-surface molecules to alleviate increased leukostasis in early DR.

b. The mir-15b~16 cluster is upregulated in RECs of diabetic rats. miR-15 and miR-16 are considered as tumor-suppressor genes, as they negatively regulate cell-cycle progression through targeting multiple genes promoting cell-cycle progression and/or induce apoptosis by targeting cell-survival genes. miR-15b and miR-16 also are shown to potentially target VEGF and regulate isoform-specific expression of VEGF and angiogenesis. miR-16 is shown to destabilize the transcript of coclooxygenase-2 (Cox-2) in monocytes, which catalyzes the conversion of arachidonic acid to potent inflammatory prostaglandins and, therefore, may contribute to suppression of inflammatory responses. Microarray profiling data described herein showed that miR-15b was increased by about 4 fold ($p<0.001$), while miR-16 was decreased by about 2.5 fold ($p<0.001$) in RECs of diabetic rats compared to normal controls. The opposite direction of changes of the expression of miR-15b and miR-16 appeared to be contradictory, as they are co-transcribed as a bicistronic miRNA cluster on rat chr2q31 (www.mirbase.org). To verify the findings from microarray profiling, qRT-PCR analysis was performed and showed that both miR-15b and miR-16 are moderately but significantly increased in diabetic RECs compared to normal controls (Table 5 and FIG. 2), which may have important implications in DR as they may modulate angiogenesis through regulating the expression of VEGF and inflammatory processes through regulating the expression of Cox-2, as well as proliferation and survival of RECs.

c. miR-21 is significantly upregulated in RECs of diabetic rats. miR-21 is often considered an oncomiR, as it is upregulated in many types of cancers and targets multiple tumor-suppressor genes to inhibit apoptosis, promote cell survival, proliferation, and invasiveness in cancers. However, in different cellular contexts, miR-21 can have different functions and negatively regulate cell-cycle progression through targeting cell division cycle 25a (Cdc25a). Both microarray (Table 5) and qRT-PCR data (FIG. 2C) showed that miR-21 is significantly increased in RECs of diabetic rats compared to normal controls, suggesting that miR-21 may respond to diabetic signals differently and play different roles in the pathogenesis of diabetic complications in different tissues. Furthermore, miR-21 is shown to be upregulated by both VEGF and NF-κB, a master regulator of many proinflammatory factors. Therefore, the upregulation of miR-21 in RECs of STZ-induced diabetic rats could be a result of NF-κB activation in RECs and/or increased expression of VEGF in diabetic rats and that miR-21 may be involved in multiple aspects of the pathogenetic pathways in DR.

d. Members of the Let-7 family are downregulated in RECs of diabetic rats compared to normal controls. In the rat genome, at least seven let-7 homologs, rno-let-7a/b/c/d/e/f/i, are encoded by at least seven genes according to miRBase v14 (www.mirbase.org) (FIGS. 3A-D). All members of the let-7 family have the same seed sequence, and therefore share similar downstream target genes. Microarray profiling data described herein showed that multiple members of the let-7 family, including rno-let-7b, c, d, e, and i, are expressed in RECs. Although let-7g is yet to be included in rat miRNA registry, microarray analysis detected significant expression of mmu-let-7g in rat retina and RECs, suggesting that the let-7g gene also may be active in the rat genome and highly expressed in the retina and RECs. Comparison of expression profiles of RECs of diabetic rats with normal controls revealed that expression levels of multiple members of the let-7 family were significantly decreased in RECs of diabetic rats by 1.6-4.9 fold, including let-7b, c, e, and g (FIG. 4), suggesting that the let-7 family may be involved in the pathogenesis of early DR. Let-7, one of the founding members of miRNAs, controls the timing of cell-cycle exit and terminal differentiation in *C. elegans*. In humans, let-7 is identified as a tumor suppressor by targeting RAS and many genes involved in cell-cycle regulation. However, in HUVECs, let-7f was reported to promote angiogenic sprouting in vitro by targeting TSP-1. If let-7 has a function similar to the one it has in HUVECs, downregulation of members of the let-7 family in RECs of diabetic rats may potentially upregulate TSP-1 and impose a negative impact on angiogenesis, contributing to the pathogenesis of early DR.

Figure 1B:
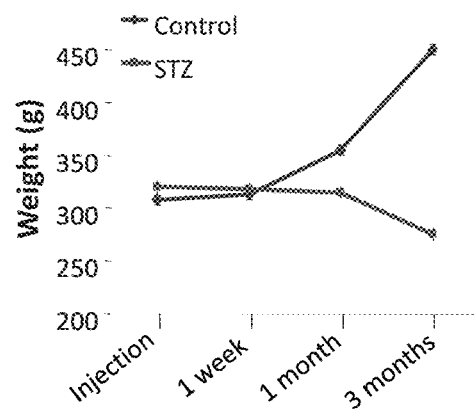
Figure 2A:
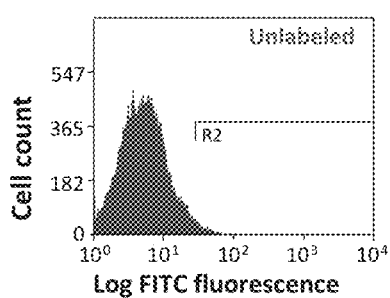
FIGS. 2A-H show isolation of retinal endothelial cells (RECs). Flow cytometry analysis showed endothelial enrichment after MACS sorting. (2A) Profile of unlabeled total retinal cells; (2B) Profile of unsorted FITC-PECAM-1-labeled cells from the retina. Approximately ~10% of the cells are FITC-PECAM-1 positive (R2); (2C) Profiles of cells sorted by MACS using PECAM-1 antibody, which showed significant enrichment of RECs to ~85% (R2). (2D-2G): Immunostaining of MACS sorted PECAM-1 positive cells which are further purified by FACS. Nearly 100% of the cells are positive for EC specific markers, von Willebrand factor (Millipore) (2D and 2E) and a rat endothelial surface marker (Abcam) (2F-2G). Nuclei of the cells are stained with Hoechst nuclear dye (2F). (2D) and (2F) are light microscopy images. (2H) Expression of PECAM-1 measured by qRT-PCR in sorted RECs (filled bar) vs. unsorted retinal cells (open bars) in control (A) and STZ-diabetic rats (B), suggesting enrichment of endothelial cells. PECAM-1 expression levels are normalized to 18S rRNA.
Figure 2B:
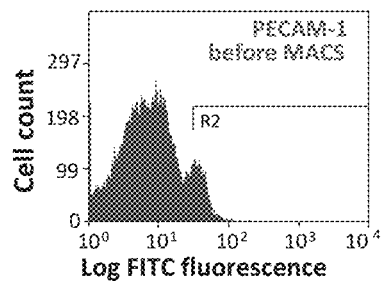
Figure 2C:
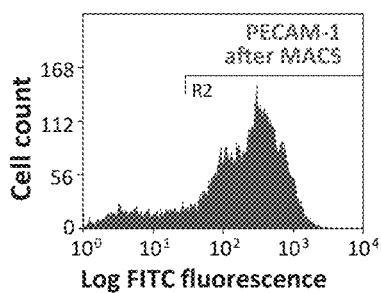
Figure 2D:
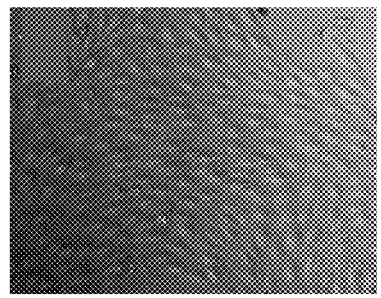
Figure 2E:
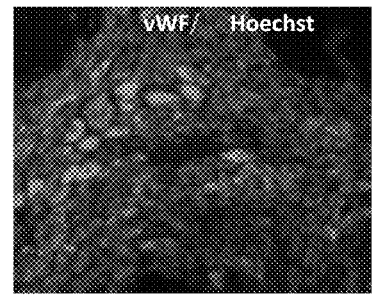
Figure 2F:
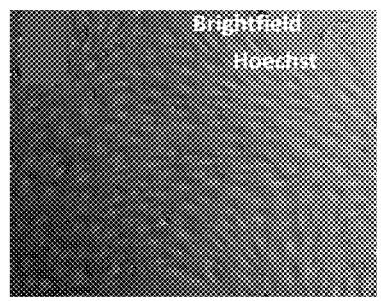
Figure 2G:
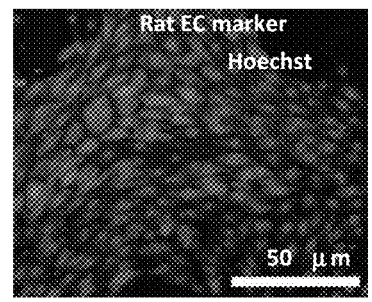
Figure 2H:
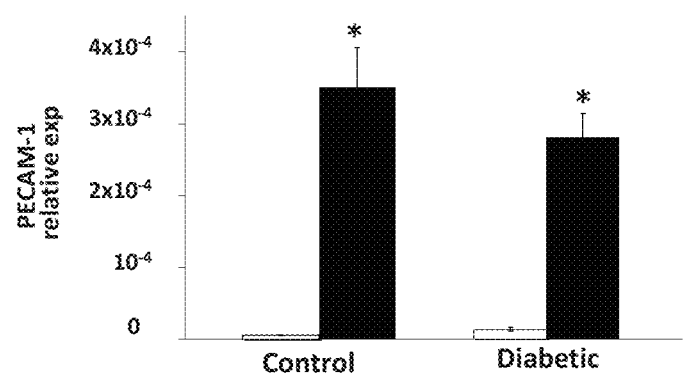

2. VEGF-responsive miRNAs and miRNAs potentially regulating VEGF and microvascular functions are significantly changed in RECs. VEGF is a potent mitogen promoting endothelial survival, proliferation, migration, angiogenesis and endothelial permeability, playing important roles in the development of DR. VEGF is shown to induce the expression of multiple miRNAs. In addition to members of the miR-17-1~92 cluster and miR-21, miR-31, miR-155 and miR-191 also are shown to be induced by VEGF in HUVECs. Interestingly, except miR-191, all VEGF-inducible miRNAs in HUVECs are confirmed to be increased in RECs of STZ-induced diabetic rats, including miR-17-5p, miR-18a, miR-20a, miR-21, miR-31, and miR-155 (FIGS. 1, 2 and 4). This miRNA "signature" may reflect the increased expression of VEGF in diabetic retinas and suggests that these miRNAs may be involved in the pathogenesis of DR through, in part, mediating functions of VEGF in RECs.

The 3'UTR of VEGF transcripts have target sites for approximately 100 different miRNAs. In vitro studies implicated that miR-20a, miR-20b, miR-15b, miR-16, miR-125a and miR-378 may target their binding sites in 3'UTR of VEGF transcript and regulate its expression. Among these, miR-20a, miR-15b and miR-16 are upregulated (FIGS. 1 and 2), while miR-20b and miR-125a are downregulated in RECs of diabetic rats compared to normal controls, suggesting potential regulatory roles of different miRNAs on VEGF expression in RECs. It appears that the miR-17-1~92 cluster may be induced by VEGF, and, in turn, members of the miR-17-1~92 cluster may target VEGF, suggesting a negative feedback regulation on expression and function of VEGF.

miR-31 is not only significantly upregulated in RECs, but also in the retinas of STZ-induced diabetic rats compared to normal controls (Tables 4 and 5 and FIG. 2). miR-31 is shown to suppress metastasis of breast cancer cells by targeting frizzled 3 (fzd3), integrin α5 (ITGA5), radixin (Rdx) and RhoA. Among these, ITGA5 also is critical for endothelial migration, angiogenesis and microvascular development, which has been shown to be regulated by miR-92a. Rdx is a member of the Ezrin, Radixin and Moesin (ERM) family, which functions as membrane-actin cytoskeleton linkers, regulating microvilli formation, cell adhesion, and mobility. ERM proteins interact with vascular cell adhesion molecule (VCAM)-1 and ICAM-1 to regulate microvascular permeability and leukocyte docking on ECs. In addition, miR-31 recently has been shown to target E-selectin in HUVECs, another cell-surface adhesion molecule that recruits leukocytes and mediates leukocyte rolling and trans-endothelial migration. Collectively, upregulation of miR-31 in RECs and retina of diabetic rats (FIG. 2) may have reflected the response of RECs and the retinas to diabetic signal in attempt to inhibit leukostasis, vascular permeability, and angiogenesis. miR-31 may potentially be used as a therapeutic target for prevention or treatment of early DR.

miR-31, with miR-150 and mir-184, was shown to be significantly decreased in retinas of mice with oxygen-induced ischemic retinopathy and laser photocoagulation-induced choroidal neovascularization. Both miR-31 and miR-184 are significantly increased in the retinas of STZ-induced diabetic rats (FIG. 2). This may be a result of different pathological and gene-expression contexts between oxygen-induced ischemic retinopathy or laser coagulation-induced choroidal neovascularization, in which proliferative neovascularization is the predominant pathology, and early DR, in which leukostasis, inflammatory response, EC-death, and increased vascular permeability are major defects in RECs and the retina.

3. NF-κB-responsive miRNAs are upregulated in RECs of diabetic rats, suggesting that miRNAs may be involved in the pathogenesis of DR through modulating the inflammatory response in RECs. miR-146a/b, miR-155, miR-132, and miR-21 were reported to be induced by multiple inflammatory factors. Interestingly, miR-146a, miR-155, miR-132, and miR-21 were all increased in RECs of STZ-induced diabetic rats compared to normal controls by microarray analysis, and further confirmed by qRT-PCR assays (Table 5 and FIGS. 2E and 4C-D), along with miR-146b, the paralogous miRNA to miR-146a (FIGS. 4A-D). miR-146a, miR-155, and miR-21 have been shown to be directly transactivated by NF-κB, a key regulator of inflammatory immune responses and microvascular functions. Activated NF-κB induces expression of a wide range of downstream target genes, including many proinflammatory mediators, contributes to diabetes-induced apoptosis of RECs and pericytes, and the pathogenesis of DR. NF-κB is known to be activated in the retina as early as two months after the onset of diabetes. Consistently, qRT-PCR analysis on retinal RNA of the STZ-induced diabetic and normal control rats described herein showed that NF-κB downstream target genes, ICAM-1 and monocyte chemoattractant protein (MCP)-1, were significantly upregulated in STZ-induced diabetic rats, suggesting NF-κB activation in diabetic retina. Therefore, upregulation of miR-146, miR-155 and miR-21 in RECs of diabetic rats may be a result of NF-κB activation in the retina, reflecting ongoing NF-κB activation and inflammatory responses in the retina and RECs of diabetic rats.

4. p53-responsive miRNAs are upregulated in both retinas and RECs of STZ-induced diabetic rats, indicating that p53-dependent apoptosis may be a common theme in early DR. The miR-34 family, including miR-34a/b/c, is a direct transcriptional target of p53, one of the major tumor-suppressor genes, and contributes to p53-mediated cell-cycle arrest, apoptosis and senescence by directly targeting genes regulating cell-cycle progression, cell survival, DNA repair, and angiogenesis. Increased expression of the miR-34 family may reflect upregulation of p53 activity. miRNA profiling results described herein showed that miR-34c, a member of the miR-34 family, and miR-34b-3p, the miRNA derived from the 3' end of the stem-loop of miR-34b, another member of the miR-34 family, are significantly upregulated in the retinas of diabetic rats compared to normal controls, suggesting that p53 is activated in the retina of diabetic rats. qRT-PCR assays were performed to test other members of the miR-34 family and showed that all members of the miR-34 family are significantly upregulated in the retinas of diabetic rats compared to normal controls, indicating that p53 is activated in diabetic retinas. qRT-PCR was also performed on p21, a known direct target of p53, and showed that p21 was significantly upregulated by approximately 62% in the diabetic retinas compared to normal controls, further supporting that p53 is activated in the retina of STZ-induced diabetic rats. p53 appears to be activated in diabetic retinas and upregulated the expression of the miR-34 family, which may mediate p53-mediated apoptosis and contribute to the neurodegeneration in diabetic retina.

Apoptotic-like REC cell death is among the earliest vascular histopathology of DR. qRT-PCR was performed and showed that expression of miR-34a was significantly increased in RECs of diabetic rats compared to normal controls. Consistently, p21 also was significantly increased by approximately 33% in RECs of diabetic rats, strongly supporting that p53 also is activated in RECs and may contribute to REC cell death and acellular capillaries during the development of early DR. Knockdown of the expression of miR-34 by anti-miRs has been shown to significantly block p53-induced apoptosis. Therefore, members of miR-34 family also are potential therapeutic targets to prevent or slow down the progression of DR by inhibiting miR-34-mediated apoptosis of RECs and neuroretinal cells.

miRNAs have diverse and versatile functions. One miRNA can target and regulate hundreds of downstream genes, while a mRNA can be targeted by multiple miRNAs, which may have synergistic or antagonistic regulatory effects. Functions of individual miRNAs in certain cell type or tissue may depend on the gene-expression context. As the gene-expression contexts changes, one miRNA may have different functions in different pathological pathways in different tissues or cell types at different stages of a disease. Interplays among miRNAs, their upstream regulators, and their downstream target genes may contribute to the overall gene expression changes in diabetic retinas and development of DR. Therefore, miRNA-expression patterns in the retina and RECs may change dynamically with the progression of the disease. miRNA-expression profiling in the retina and RECs at different stages of DR may further reveal miRNA signatures of the progression of the disease.

In addition to being recognized as a major level of gene expression regulation, unique miRNA expression profiles also have emerged as diagnostic biomarkers for various pathological conditions. miRNA-expression profiling data in the retinas and RECs of STZ-induced diabetic rats have revealed potential "signatures" of different pathological processes ongoing in the eyes of diabetic animals, e.g. NF-κB activation and related inflammatory process (with miR-146, miR-155, miR-132, and miR-21), apoptosis (with the miR-34 family), and angiogenesis (with the VEGF-responsive miRNAs including the miR-17-1~92a cluster).

Novel therapeutic targets for treatment of diabetic retinopathy:

1. miR-146 is used to inhibit NF-κB activitivation for the treatment of diabetic retinopathy. Inflammatory processes and microvascular damage have significant contribution to the development DR. NF-κB, a key regulator of inflammatory, immune responses and microvascular functions, plays important roles in the pathogenesis of DR. Increased expression level of many proinflammatory cytokines and haemodynamic factors, promoting NF κB activation, e.g. IL-1β, TNF, Angiotensin (Ang) II, endothelin-1 (ET-1), platelet-activating factor (PFA) and advanced glycation end-products (AGE) have been reported in the retina and/or vitreous fluid of patients with proliferative DR, and diabetic rats. NF-κB is activated in retina as early as two months after the onset of diabetes. Activated NF-κB induces expression of wide range of downstream target genes, including many proinflammatory mediators, and contributes to diabetes-induced apoptosis of the RECs and pericytes and the pathogenesis of DR.

The upregulation of miR-146 in the RECs in STZ induced diabetic rats may be a result of NF-κB activation; and that miR-146 may be involved in DR through its regulation on NF-κB activation and other target genes in RECs; and therefore, miR-146 is used as a novel therapeutic target for the treatment of DR by inhibiting NF-κB activation and therefore inflammatory processes in the retina.

Figure 4A:
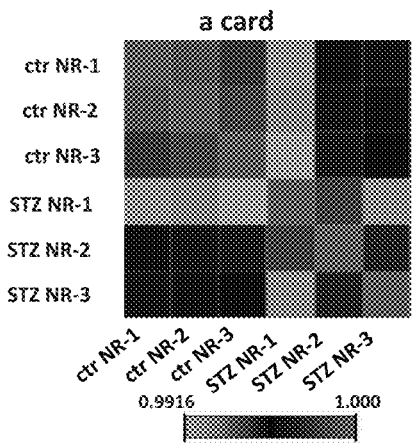
FIGS. 4A-D show correlation of three miRNA profiles of the neuroretina (NR) and STZ-induced diabetic and normal control rats. (A): correlation heatmap for an a-microarray (4A) and a b-microarray (4C) card; (B): hierarchical clustering for an a-microarray (4B) and a b-microarray (4D) card.
Figure 4B:
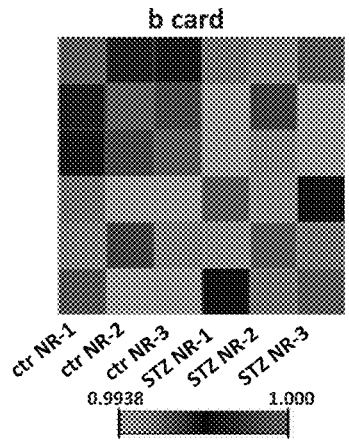
Figure 4C:
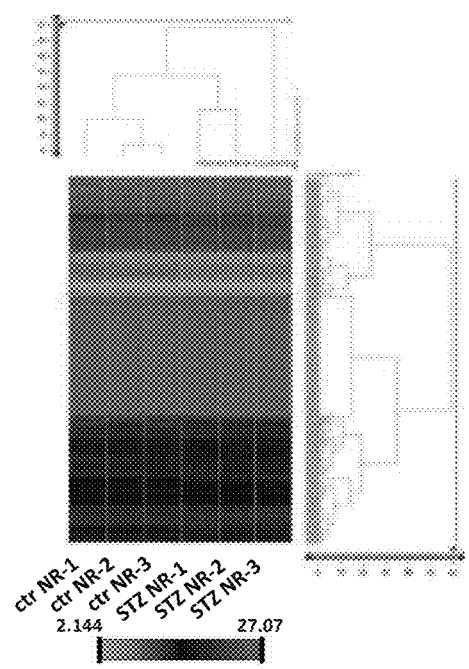
Figure 4D:
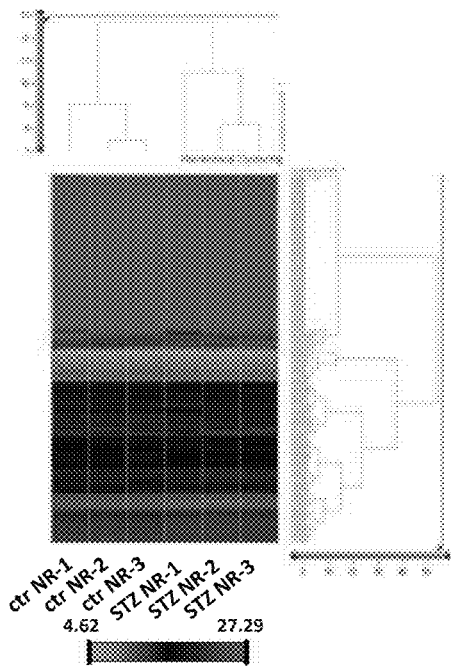
Figure 5:
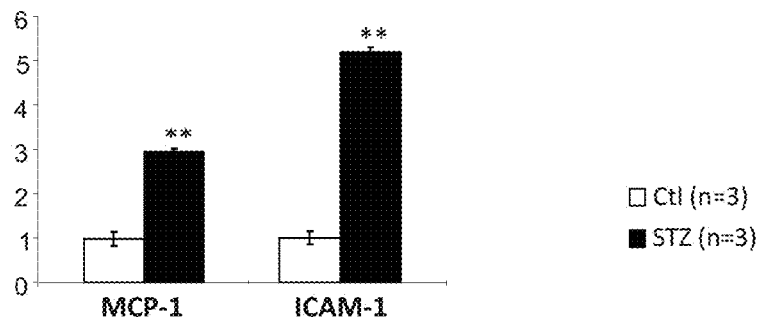
FIG. 5 shows qRT-PCR analysis of NF-κB downstream genes, MCP-1 and ICAM-1 in the retina of STZ-induced diabetic rats and normal controls. **: $p<0.01$.
Figure 6:
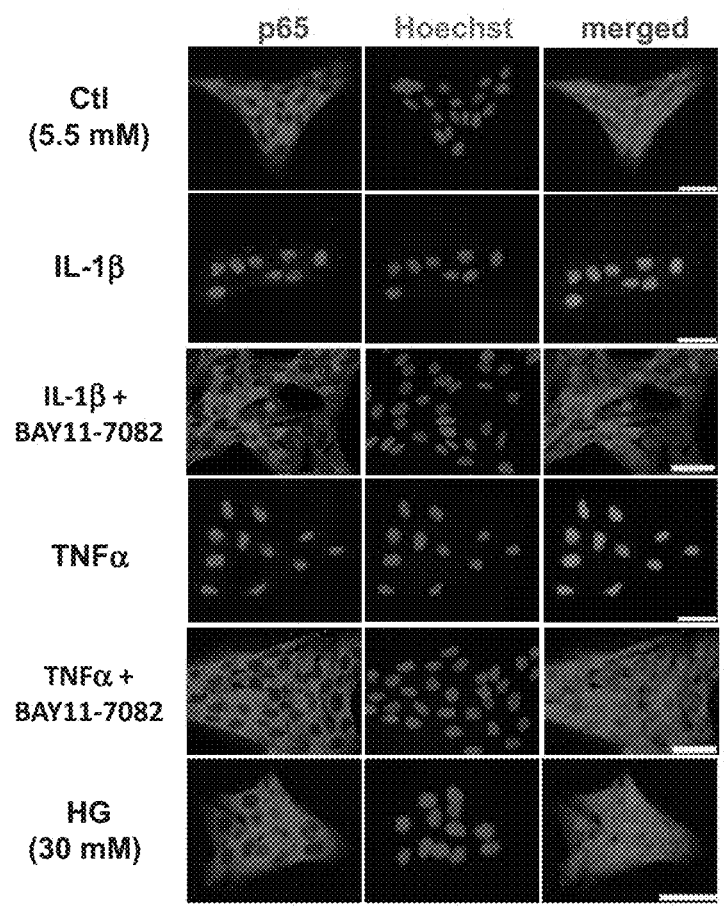
FIG. 6 shows NF-κB p65 immunofluorescence on rat RECs treated with IL-1β (10 ng/ml) and TNFα (10 ng/ml) with or without simultaneous treatment of NF-κB inhibitor, Bay11-70832 (3 μM/ml), 30 minutes after the treatment. IL-1β and TNFα activated NF-κb manifested by nuclear translocation of p65. When simultaneously treated with Bay11-7082, IL-1β and TNFα failed to activate NF-κB, and p65 remained in the cytosol, similar to the non-treated controls (ctl). Scale bars=50 μm. High glucose (30 mM. HG) did not result in the NF-κB activation either.
Figure 7A:
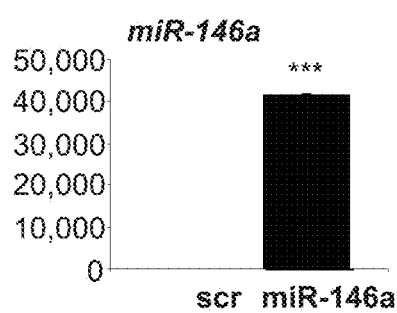
FIGS. 7A-E show qRT-PCR analysis showed that miR-146a is upregulated (7A); IRAK1 (7B) and TRAF6 (7C) are downregulated in RECs 48 hours after the transfection of miR-146a mimics (miR-146a) when compared to the ones transfected with negative control miRNA mimics with scrambled sequences (scr). (7E): Western blot analysis on IRAK1 in RECs transfected with miR-146a mimics or negative control miRNA mimics with scrambled sequences (scr) (7D). *: $p<0.05$; ***: $p<0.001$.
Figure 7B:
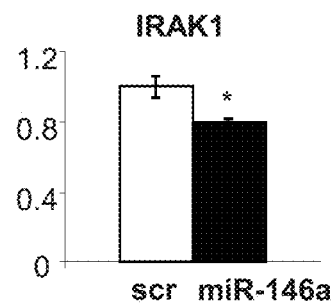
Figure 7C:
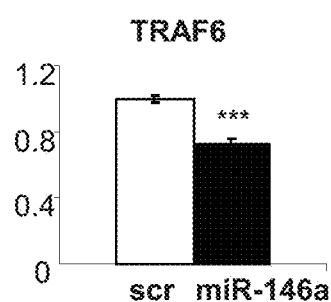
Figure 7E:
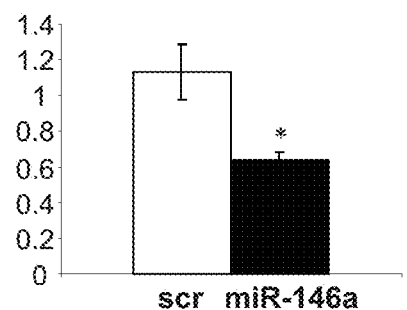
Figure 7D:
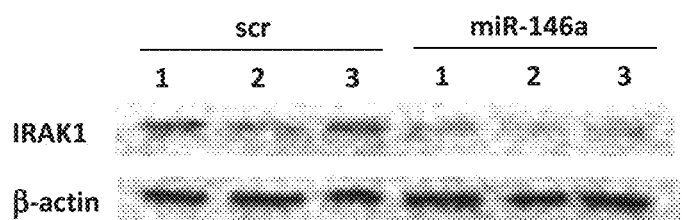
Figure 8:
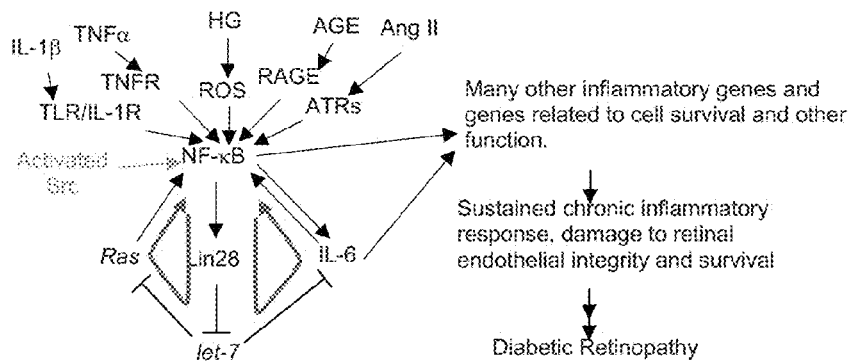
FIG. 8 shows let-7-involved NF-κB-activation positive feedback loops in breast cells and their potential involvement in DR. In diabetic retina, hyperglycemia-induced ROS, many other inflammatory factors, e.g. IL-1β, TNFα, angiotensin II (AngII) and advanced glycation end-products (AGE) activate NF-κB. Then, NF-κB activates Lin28, which downregulates let-7 to release let-7's suppression on IL-6 and Ras, which further activate NF-κB, completing the positive feedback loops. After NF-κB and the positive feedback loops are activated, the positive feedback loops maintain NF-κB activation, contributing to the development of DR and metabolic memory of diabetes in DR.
Figure 9A:
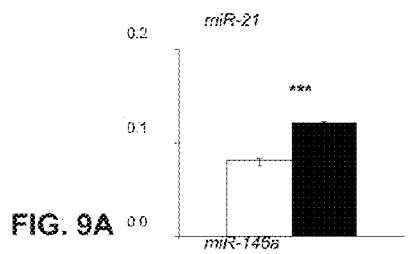
FIGS. 9A-E show relative expression levels of NF-κB-responsive miRNAs, miR-21 (SEQ ID NO: 66) (9A), miR-132 (SEQ ID NO: 67) (9B), miR-146a (SEQ ID NO: 68) (9C), miR-146b (SEQ ID NO: 69) (9D) and miR-155 (SEQ ID NO: 70) (9E) in RECs of normal control (n=3) (open bars) and diabetic rats (n=3) (filled bars). Mammalian snRNA U6 was used for normalization control. *: $p<0.05$; : $p<0.01$; *: $p<0.001$.
Figure 9B:
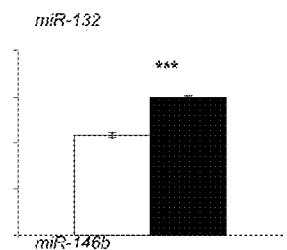
Figure 9C:
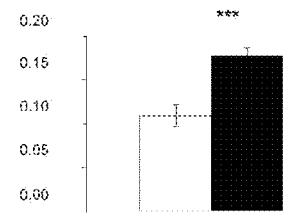
Figure 9D:
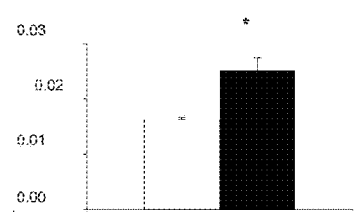
Figure 9E:
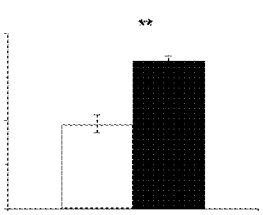

A. miR-146 inhibit IL-1R/Toll-like receptor (TLR)-mediated NF-κB activation pathway in Recs: miR-146a is not only transactivated by NF-κB, but also inhibits NF-κB activation by targeting two key adaptor proteins, IL-1 receptor-associated kinase (IRAK1) and TNF receptor-associated factor 6 (TRAF6), of the MyD88-dependent IL-1R/Toll-like receptor (TLR)-mediated NF-κB activation pathway in several different cell types, forming a negative feedback regulatory loop. The negative feedback regulation of miR-146 on NF-κB activation may have important implication in DR, as inhibition of NF-κB activation in diabetic rats has been shown to inhibit the development of DR. In diabetic retinas, hyperglycemia-induced increased production of ROS and proinflammatory cytokines work in concert to activate NF-κB in RECs. Both IL-1β and TNF-α are shown to activate NF-κB in RECs. Upregulation of miR-146a is a result of NF-κB activation. Rat RECs (the TR-iBRB2 cells) were treated with IL-1β (10 ng/ml) and TNF-α (10 ng/ml). NF-κB was activated, and miR-146a was significantly upregulated in RECs, four hours and 24 hours after both treatments (FIG. 4C). The extent of upregulation of miR-146a was further increased from 4-hour to 24-hour treatments. However, when cells were simultaneously treated with NF-κB inhibitor, Bay11-7082, which irreversibly inhibits IκBα phosphorylation, IL-1β-induced upregulation of miR-146a was significantly decreased by ~81%, and TNF-α-induced upregulation was completely blocked, strongly supporting that increased expression of miR-146a in RECs of diabetic rats is mostly a result of NF-κB activation (FIG. 4D). It is noteworthy that there is a moderate, but significant increased expression of miR-146a by IL-1β in the presence of Bay11-7082, compared to non-treated negative controls.

To determine whether high glucose culture could directly induce the expression of miR-146a rat RECs were cultivated in a medium with 30 mM glucose for 24 hours and 7 days. qRT-PCR results showed no upregulation of miR-146a at both time points in high glucose culture, consistent with a previous report that RECs respond to cytokines, e.g. IL-1β and TNFα, rather than high glucose; and exposure of RECs to high glucose does not stimulate endogenous ROS production and activation of NF-κB, suggesting that diabetes-induced upregulation of miR-146a may depend on the paracrine effects of hyperglycemia-induced increased production of cytokines, e.g. IL-1β and TNFα, by other cell types in the retina, e.g. Müller glia, retinal pigmented epithelial (RPE) cells, and other retinal neurons.

RECs were transfected with miR-146a mimics. Forty-eight hours after transfection, the expression of both IRAK1 and TRAF6 was significantly reduced at the mRNA level. Although the anti-TRAF6 antibodies failed to detect any signals, Western blot analysis on IRAK1 showed a significant decrease of IRAK1 proteins in RECs transfected with miR-146a mimics (FIG. 7). IRAK1 and TRAF6 are targeted by miR-146 in RECs. To test the effect of miR-146a on NF-κB activation in RECs, 48 hours after transfection, the cells were treated with IL-1β (10 ng/ml) or TNFα (10 ng/ml). Twenty-four hours after the cytokine treatment, RNA was isolated from the treated cells and qRT-PCR assays were performed on NF-κB downstream target genes, including MCP-1 and ICAM1. The results showed that transfection with miR-146a mimics significantly reduced IL-1β-induced expression of NF-κB downstream genes, MCP-1 and ICAM-1, by 73% and 43%, respectively, strongly supporting that miR-146 inhibits the IL-1R/TLR-mediated NF-κB activation pathway in RECs, and that the negative feedback regulation of miR-146 on NF-κB activation may function in RECs, Interestingly, TNFα-induced NF-κB activation was not affected, consistent with that IRAK¹ and TRAF6 are not the main mediators of the TNFα-induced NF-κB activation pathway, suggesting the specificity of the inhibitory effect of miR-146 on the IL-1R/TLR-mediated NF-κB activation pathway. Therefore, miR-146 is an alternative therapeutic target for the treatment of DR through its inhibition on NF-κB activation in RECs.

B. miR-146 inhibits G-protein coupled receptor (GPCR)-mediated NF-κB activation pathway by targeting CARD10.

Figures 21A, 21B:
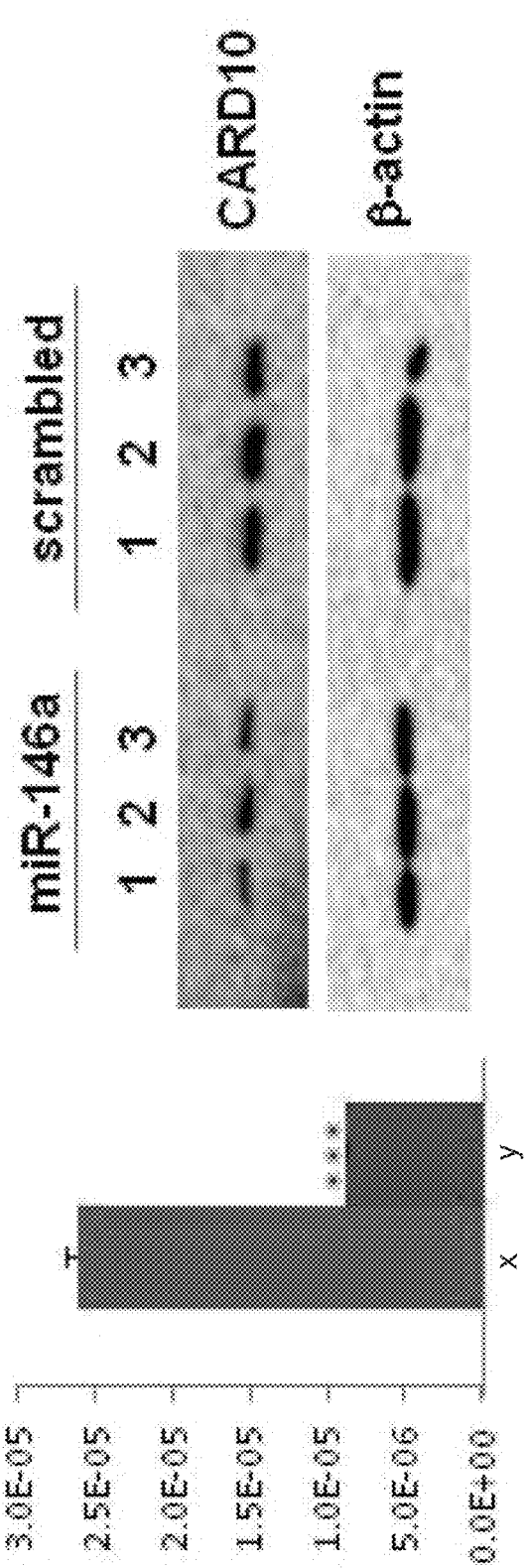
FIGS. 21A-B miR-146 target endogenous CARID10 expression in human retinal endothelial cells (HRECs); miR-146a mimics (12 nM) were transfected into HRECs using RNAiMAx lipofectamin (Invitrogen); 48 hours after transfection, cells were harvested for qRT-PCR assays (A) and (B) Western blot analysis. ***: p<0.001. x: HRECs transfected with scrambled oligonucleotides; y: HRECs transfected with miR-146a mimics.

By target prediction, miR-146 was predicted to target CARD10, which is a key molecule in G-protein coupled receptor (GPCR)-mediated NF-κB activation pathway. Ligands of GPRC include angiotensin II, endothelin-1, lysophosphatidylcholine (LPC), lysophosphatidic acid (LPA), platelet-activating factor (PAF) and thrombin, and the like. GPCR mediated NF-κB activation plays important roles in inflammation, diabetic retinopathy, diabetic nephropathy, atherosclerosis, inflammatory bowel disease, and so forth. miR-146a targets CARD10 as shown by luciferase reporter assay (FIG. 20). miR-146a directly inhibits the expression of endogenous CARD10 in human retinal endothelial cells (FIG. 21).

2. let-7-involved NF-κB-activation positive feedback loops may be activated in retinal endothelial cells of diabetic retina, and contribute to sustained inflammation and metabolic memory in diabetic retina; furthermore, inactivation of these positive feedback loops may decrease inflammatory response and "erase" or attenuate metabolic memory in DR, and therefore, is a new therapeutic strategy for treatment of DR.

NF-κB-responsive miRNAs were upregulated, suggesting that NF-κB was activated; while let-7 was downregulated in RECs of diabetic rats; and Lin28 was upregulated in RECs in high glucose culture, suggesting that the newly discovered, let-7-involved NF-κB-activation positive feedback loops may exist and be activated in RECs of diabetic rats. NF-κB is activated early in DR, and remains activated in the absence of hyperglycemia after transient exposure to hyperglycemial. IL6 is increased in the retina and vitreous of diabetic patients; high glucose stimulates IL6 expression in endothelial cells. Ras is activated in retinal microvessels in diabetic rats and in RECs in high glucose culture. let-7-involved NF-κB-activation positive feedback loops may be activated in RECs and contribute to sustained inflammation and metabolic memory in diabetic retina; furthermore, inactivation of these positive feedback loops may decrease inflammatory response and "erase" or attenuate metabolic memory in DR, and therefore, is a new therapeutic strategy for treatment of DR.

The newly discovered let-7-involved NF-κB-activation positive feedback loops may be activated in RECs in diabetic retina, and play important roles in the sustained inflammatory response, microvascular damage and metabolic memory in DR. In diabetic retina, NF-κB activation plays a pivotal role in initiating and maintaining inflammatory responses, microvascular damage and metabolic memory in DR. Therefore, let-7-involved positive feedback loops provide a plausible mechanism for chronic inflammatory processes and metabolic memory in RECs of diabetic retina; inactivation of these positive feedback loops may prevent or decrease the inflammatory responses, and "erase" or attenuate metabolic memory of DR.

The let-7-involved NF-κB-activation positive feedback loops may be activated in RECs in high-glucose culture and responsible for sustained inflammatory response and metabolic memory in vitro. To test whether let-7-involved NF-κB-activation positive feedback loops are activated in diabetic RECs and contribute to the dysfunction and metabolic memory of RECs in vitro, RECs were treated with either HG (30 mM) or NG (5 mM) in a "primary" culture (FIG. 12). 24 hours, 1 week and 2 weeks later, RNA and protein of the cells were harvested to test whether let-7-involved NF-κB activation positive feedback loops were activated in RECs treated with HG. First, to confirm NF-κB activation by: 1) qRT-PCR assays on p65 subunit of NF-κB; 2) semi-quantitative Western blot on p65 and phosphorylated p65 (p-65), IKK and phosphorylated IKK (p-IKK), one of the key components of NF-κB-activation pathways; 3) p65-ActivELISA assay (IMGENEX), which quantify nuclear p65; 4) NF-κB-responsive-element binding assays (TranAM-NF-κB-p65 which quantifies activated NF-κB binding to oligonucleotides of NF-κB-responsive element; 5) qRT-PCR and semi-quantitative Western blot analyses on downstream targets of NF-κB, which play important roles in dysfunction of RECs in DR, including VEGF, ICAM-1, VCAM-1, Cox-2, iNOS and MCP-1. 6) qRT-PCR assays on NF-κB-responsive miRNAs, including miR-21, miR-146, miR-132 and miR-155; and then, the expression of all other components of the let-7-involved positive feedback loops, including Lin28, IL-6, H-ras, K-ras and N-ras by qRT-PCR and semi-quantitative Western blot are examined, as well as let-7 by Taqman miRNA qRT-PCR assays on let-7a/b/c/d/e/f/g/I.

Increased proinflammatory factors may lead to functional defects of RECs, e.g. increased permeability. To test the functional consequences of HG culture, two experiments are suitable: 1) in vitro permeability assay, in which leakage of dextran-FITC through REC monolayer is monitored; 2) trans-endothelial electrical resistance measurement.

Figure 12:
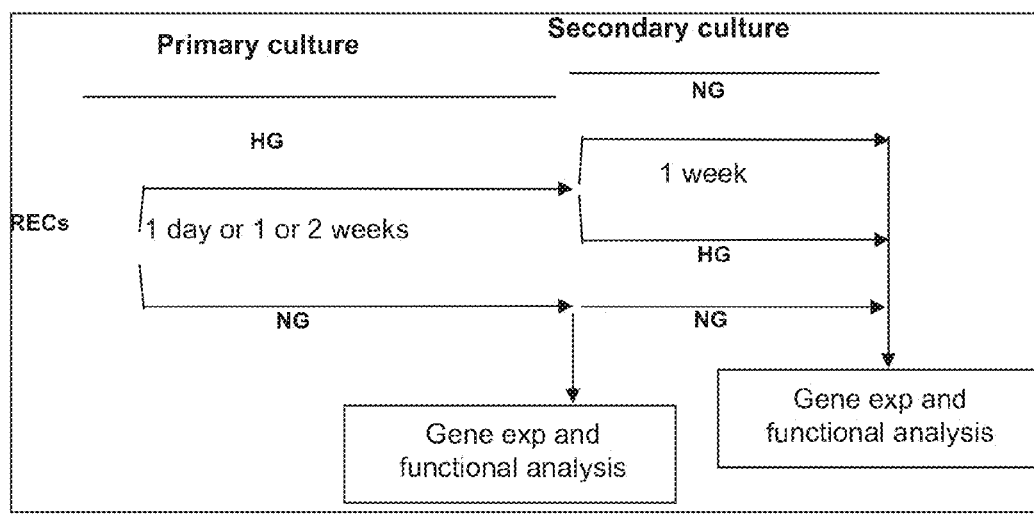
FIG. 12 is a schematic illustration of an overall experimental design described herein for RECs; HG=high glucose culture; NG=normal glucose culture.

To test whether let-7-involved positive feedback loops are involved in metabolic memory in RECs, after the 24-hour, 1-week or two-week primary culture, one set of cells under HG are transferred to NG medium (HG-to-NG) for a secondary culture (FIG. 12, while another set of cells under HG continues to be cultured in HG (HG-to-HG) in the secondary culture. RECs cultured in NG continues in NG for negative control (NG-to-NG). The secondary culture continues for 1 week. Subsequently, the cells are harvested and analyzed NF-κB activation, the levels of expression p65 subunit of NF-κB, Lin28, IL-6, Ras, let-7 and other NF-κB downstream genes, including NF-κB-responsive miRNAs.

After the primary culture, NF-κB is activated in RECs in HG compared to the ones in NG, manifested by increased p-65 and p-IKK by Western blot assays, increased nuclear p65 by ActivELISA assays, increased NF-κB-responsive-element binding activity by TranAM binding assays, and increased expression of NF-κB downstream genes and miR-NAs. NF-κB activation also may be detected as increased levels of mRNA transcripts of p65 by qRT-PCR assays. However, as NF-κB activation may be more of a posttranslational event by phosphorylation of p65 and its translocation to the nuclei, p65 transcript may not be significantly upregulated, even if NF-κB is activated. In regard to the positive feedback loops, Lin28 is upregulated at both mRNA and protein levels, as activated NF-κB may directly trans-activate the expression of Lin28. Downregulation of mature let-7, as Lin28 inhibits maturation of let-7. Furthermore, Ras and IL-6 are upregulated in RECs in HG, because let-7 is decreased, and Ras and IL-6 are direct targets of let-7. In addition, IL-6 can also be induced by Ras and NF-κB. Functionally, increased endothelial permeability with increased dextran-FITC leakage and decreased transendothelial electrical resistance through REC monolayer cultured in HG compared to the ones in NG, because of NFκB activation and subsequent increased expression of pro-inflammatory factors.

After the secondary culture, in RECs with HG-to-NG treatment, NF-κB remains to be activated compared to RECs in NG-to-NG, suggesting metabolic memory in RECs. If let-7-involved positive feedback loops are involved in metabolic memory in RECs, in HG-to-NG RECs, Lin28 may remain upregulated, let-7 downregulated, and Ras and IL-6 upregulated. Functionally, similar to RECs in HG and HG-to-HG culture, endothelial permeability may remain increased in HG-to-NG RECs, compared to RECs in NG and NG-to-NG culture. let-7-involved NF-κB-activation positive feedback loops may be activated in RECs in HG, and contribute to sustained inflammation and metabolic memory of HG in RECs.

3. miR-31 may inhibit leukostasis and vascular permeability, and therefore, prevent or slow down the development of early diabetic retinopathy (DR). miR-31 is significantly upregulated in both RECs and the neuroretina of STZ-induced diabetic rats compared to normal controls, providing the first direct evidence that miR-31 may be involved in the pathogenesis of DR. Recently, miR-31 has been shown to be induced by both vascular endothelial growth factor (VEGF) and tumor necrosis factor (TNF)α in human umbilical vein endothelial cells (HUVECs), and may target E-Selectin, a cell-surface adhesion molecule that recruits leukocytes and mediates leukocyte adhesion and migration on ECs Inactivation of miR-31 in HUVECs increased neutrophil adhesion in vitro, while overexpression of miR-31 downregulated E-selectin expression and reduced neutrophil binding. This finding has important implications to the pathogenesis of DR, as leukostasis is an important component of the inflammatory processes, contributing to microvascular damage. It is one of the earliest events during development of DR, whereby blood-borne leukocytes adhere strongly to endothelial plasma membrane and become entrapped, leading to capillary occlusion, local ischemia and subsequent hypoxia-induced responses; trapped leukocytes generate and release toxic superoxide radicals, contributing to REC damage and increased vascular leakage, which may further lead to retinal edema and chains of downstream pathological reactions. Kostasis is mediated by surface adhesion molecules on leukocytes and vascular ECs, e.g. E-selectin, intercellular adhesion molecule-1 (ICAM-1), vascular adhesion molecule-1 (VCAM-1) and other junctional adhesion molecules. Upon leukocyte adhesion, ECs form actin-rich "docking structures" to reinforce leukocyte adhesion and migration on ECs. The docking structures are concentrated with !CAM-1 and VCAM-I, as well as adaptor- and linker-molecules, including ERM (ezrin, radixin and moesin) proteins. miR-31 was reported to target hypoxia-inducible factor (HIF) hand platelet-derived growth factor (PDGF)-B; and intraocular injection of pre-miR-31 reduced ischemia-induced neovascularization in the retina and laser photocoagulation-induced choroidal neovascularization.

4. Expressions of members of miR-17-92 and miR-106a-363 clusters are significantly changed in RECs during the development of DR, suggesting their potential roles in the pathogenesis of DR. miR-17-1-92, miR-17-2-363 and miR-106b-25 clusters are conserved, paralogous miRNA clusters. Members of these paralogous clusters have been shown to function as oncogenes, modulating cell cycle progression, apoptosis, and angiogenesis, playing important roles in tumorigenesis, as well as normal development of various tissues. Among the confirmed differentially expressed miR-NAs in RECs, miR-19b is a member of the miR-17-1-92 and miR-17-2363 clusters, However, miR-92a, another member of either the miR-17-1'92 cluster or the miR-17-2-363 cluster, and miR-20b, a member of the miR-17-2363 cluster, were both significantly downregulated. To further evaluate the expression of these clusters, qRT-PCR was performed on other members of these miRNA clusters, including miR-17, miR-18a, miR-19a, and miR-20a. Results showed that, similar as miR-19b, all members of the miR-17-1-92a cluster, except miR-92a, were significantly upregulated in RECs of STZ-induced diabetic rats compared to normal controls, supporting that expression of miR-17-1-92a cluster may be upregulated, while miR-17-2-363 cluster may be downregulated in RECs of STZ-induced diabetic rats compared to normal controls. miR-17 and miR-92a can be derived from either the miR-17-1-92a cluster (17-1 and miR-92a-1) or the miR-17-2363 cluster (miR-17-2 and miR-92a-2).

miR-93, a member of the miR-106b-25 cluster, was increased in RECs of STZ-induced diabetic rats by microarray analysis; however, the change in the expression levels of miR-93 failed to be confirmed by qRTPCR assay. Additionally, the other two members of this cluster, miR106b and miR-25 did not show significant changes in microarray analysis. These results suggest that expression of the miR-106b'-25 cluster did not change significantly in RECs during the development of early DR.

In HUVECs, miR-17-5p, miR-18a and miR-20a are reported to be induced by VEGF, a potent angiogenic cytokine playing critical roles in the pathogenesis of DR. In addition, miR-17-5p and miR-17-3p were shown to be induced by TNF in HUVECs. Both VEGF and TNFα are upregulated in the retina early in DR.

miR-18a and miR-19b have been reported to promote angiogenesis, in part, by targeting angiogenic inhibitors, thrombospondin (Tspl) and connective tissue growth factor (CTGF). miR-92a is reported to block angiogenesis in vitro and in vivo by targeting mRNAs corresponding to several pro-angiogenic proteins, including integrin subunit a5 (ITGA5), which plays central roles in vascular development, endothelial cell migration and angiogenesis. Therefore, upregulation of miR-18a and miR-19b, and downregulation of miR-92a in RECs of diabetic rats, may promote angiogenesis, which may represent the response of RECs to increased endothelial cell death in early DR.

Retinal capillary leukostasis is one of the earliest changes in the development of DR, which may lead to capillary occlusion and local tissue ischemia. ICAM-1 on endothelial cells plays important roles in leukostasis. Although expressed at a relatively low level, miR-17-3p was significantly increased in RECs of diabetic rats compared to normal controls, suggesting that RECs may be attempting to decrease cell surface molecules to alleviate increased leukostasis in early DR.

5. The miR-15b-16 cluster is upregulated in RECs of diabetic rats. They may modulate both angiogenesis, through regulating the expression of VEGF, and the inflammatory processes, through regulation on the expression of Cox-2, and also influence the proliferation and survival of RECs, therefore, novel therapeutic targets. miR-15 and miR-16 are considered as tumor suppressor genes, as they are shown to negatively regulate cell cycle progression from G0/G1 to S phase through downregulation of multiple genes promoting cell cycle progression, and/or induce apoptosis by targeting cell-survival genes. Microarray profiling data showed that miR-15b was increased by about 4 fold ($p<0.001$), while miR-16 was decreased by about 2.5 fold ($p<0.001$) in RECs of diabetic rats compared to normal controls. The opposite directions of changes of expression of miR-15b and miR-16 appeared to be contradictory, as they are co-transcribed as a bicistronic miRNA cluster on rat chr2g31 (www.mirbase.org). To verify the findings from microarray profiling, qRT-PCR analysis was performed and showed that miR-15b, as well as miR-16, are moderately but significantly increased in diabetic RECs compared to normal controls, supporting that expression of the miR-15b-16 cluster is upregulated in diabetic RECs. Upregulation of miR-15b and miR-16 may have important implication in the development of DR, as they may modulate both angiogenesis, through regulating the expression of VEGF, and the inflammatory processes, through regulation on the expression of Cox-2, and also influence the proliferation and survival of RECs.

6. miR-21 is significantly upregulated in RECs of diabetic rats and miR-21 may be involved in multiple aspects of the pathogenetic pathways in DR and could have different effects on the functions of RECs at different stages of the disease, therefore is a novel therapeutic target for the treatment of diabetic retinopathy at different stage of the disease. miR-21 is often considered an oncomiR, as it is upregulated in many types of cancers, and may target multiple tumor suppressor genes, e.g. programmed cell death protein 4 (PDCD4) and phosphate and tensin homologue (PTEN), and cytein-rich protein with kazal (RECK), to inhibit apoptosis, promote cell survival, proliferation and invasiveness in cancers. However, it is also shown that miR-21 may have different functions in different cellular context, as miR-21 may negatively regulate cell cycle progression through targeting cell division cycle 25a (Cdc25a), a phosphatase that dephosphorylates and activates cyclindependent kinase and therefore, promote cell cycle progression. In glomerular tissues of db/db diabetic nephropathy mice, miR-21 is reported to be downregulated, compared to normal control mice). miR-21 is significantly increased in RECs of diabetic rats compared to normal controls, suggesting that miR-21 may respond to diabetic signals differently in different tissues and play different roles in the pathogenesis of diabetic complications in different tissues.

7. Members of miR-29 family (miR-29a/b/c) decreased in diabetic retinal endothelial cells, are novel therapeutic targets through their actions on PDGFB. The miR-29 family is predicted to target PDGFB (Targetscan). PDGFB secreted by RECs regulates pericytes proliferation and is critical for the recruitment of pericytes and vascular smooth muscle cells to blood vessel. Defects in PDGFB retention in microvessels results in abnormal development of retinal vasculature and the retina miR-29b/c and miR-29a*/b*/c* were shown to be downregulated in the RECs of STZ-induced diabetic rats; the downregulation of miR-29c was further confirmed by qRT-PCR, suggesting that expression of miR-29 family is decreased significantly in RECs of diabetic rats in response to diabetic stimuli, which may potentially increase the expression of PDGFB and help protect the integrity of retinal microvasculature.

8. miR-130a, a miRNA shown to promote angiogenesis in HUVECs by downregulation on two anti-angiogenic homeobox genes, GAX and HOXAS, is downregulated in RECs of diabetic rats by 2.2 Fold ($p=2.8\times10^{-5}$), suggesting roles of miR-130a in the modulating retinal microvascular function in DR and as a therapeutic target for the treatment of diabetic retinopathy.

9. p53-responsive miRNAs, miR-34albIc are upregulated in both neuroretina and RECs, indicating that p53-dependent apoptosis is a common theme in early DR. Inhibition of the these miRNAs may be used as novel therapy to prevent neuronal and endothelial cell death, therefore, treat diabetic retinopathy. The miR-34 family, including miR-34a/b/c, is a direct transcriptional target of p53, one of the major tumor suppressor genes, and contributes to p53-mediated cell cycle arrest, apoptosis and senescence by directly targeting genes regulating cell cycle progression, and cell survival, DNA repair and angiogenesis. Expression of miR-34 family may reflect the status of p53 activity in the tissue. miRNA profiling result showed that miR-34c, a member of the miR-34 family, and miR-34b-3p, the miRNA derived from the 3' end of the stem-loop of miR-34b, another member of the miR-34 family, are significantly upregulated in the neuroretina of STZ-induced diabetic rats compared to the normal controls, suggesting that p53 is activated in the retina of diabetic rats. To test this hypothesis, qRT-PCR assays were done to test other members of the miR-34 family, and showed that all members of the miR-34 family are significantly upregulated in the neuroretina of STZ-induced diabetic rats compared to normal controls, indicating that p53 is activated in the diabetic retina. To further prove this, qRT-PCR was performed on p53 and p21, a direct target of p53, and showed that p21 was significantly upregulated by approximately 62% in the diabetic retina compared to the normal controls, further supporting that p53 is activated in the retina of STZ-induced diabetic rats. Retinal cell loss has been reported in both diabetic patients and experimental diabetic animal models. In streptozotocin (STZ)-induced diabetic rats, increased apoptosis in the inner nuclear and ganglion cell layers starts only two weeks, and reduction of ganglion cells was observed as early as 4 months after the onset of diabetes. p53 is activated in the retina of diabetic rats, and miR-34 family may mediate its functions as a tumor suppressor and contribute to the neurodegeneration in DR.

Apoptotic-like REC cell death is among the earliest vascular histopathology of DR. To test whether p53 activation-induced upregulation of miR-34 family also occurs in the RECs, qRT-PCR was performed and showed that expression of miR-34a was significantly increased (by 3.1 fold) in RECs of diabetic rats compared to the ones of normal controls. Consistently, p21 also was significantly increased by approximately 33% in RECs of diabetic rats, strongly supporting that p53 also was activated in RECs in early DR and induced the expression of the miR-34 family, which may contribute to REC cell death and acellular capillaries in the eyes of DR. Knockdown of the expression of miR-34 by anti-miRs has been shown to significantly block p53-induced apoptosis. Therefore, members of miR-34 family are new therapeutic targets to prevent or slow down the progression of DR by inhibiting miR-34 mediated apoptosis of RECs and neuroretinal cells.

Figure 3A:
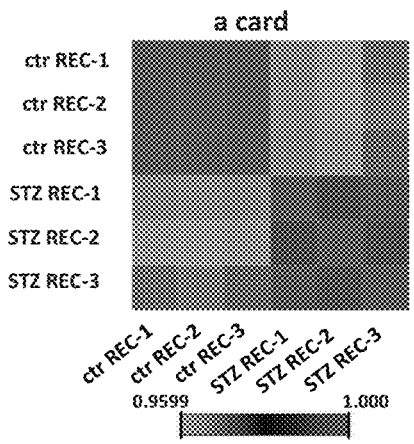
FIGS. 3A-D show correlation of three miRNA profiles of retinal endothelial cells (RECs) of STZ-induced diabetic and normal control rats. (3A and 3C): correlation heatmap of an a-microarray (3A) and a b-microarray (3C) card; (3B): hierarchical clustering for an a-microarray (3B) and a b-microarray (3D) card.
Figure 3C:
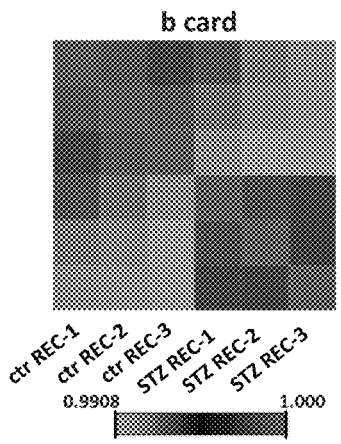
Figure 3B:
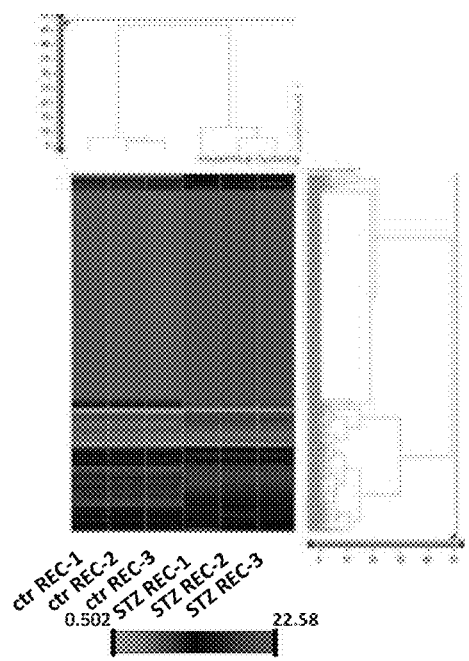
Figure 3D:
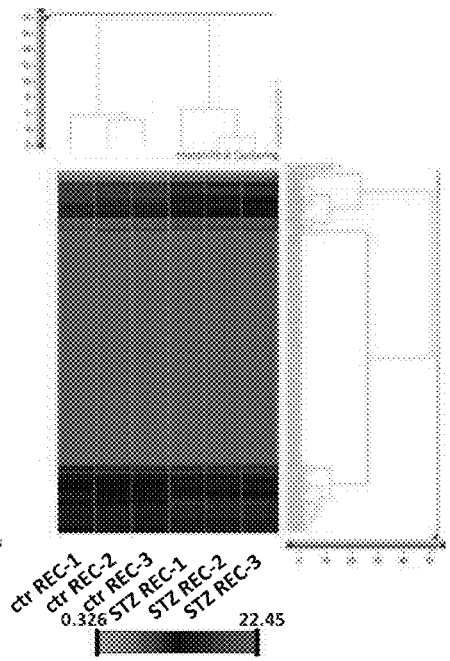

10. NF-kB-responsive miRNAs (miR-146, miR-155, miR-132 and miR-21) are upregulated in RECs of diabetic rats, indicating NF-kB activation in the RECs of diabetic rats, and that miRNAs may be involved in the pathogenesis of DR through modulating inflammatory response in RECs. Appplication of these miRNAs may inhibit NF-κB activation and inflammatory response and diabetic retinopathy. miR-146, miR-155, miR-132 and miR-21 were reported to be downstream of NF-κB and can be induced by multiple inflammatory factors in a NF-κB-dependent manor. In RECs of STZ-induced diabetic rats, miR-146a, miR-155, miR-132 and miR-21 were increased when compared to normal controls. As described herein, the upregulation of miR-21 is further confirmed by qRT-PCR (FIG. 3C). To confirm the result on miR-146a, miR-132 and miR-155, qRT-PCR was performed and showed that all three are significantly upregulated in RECs of diabetic rats by 2.1, 1.4 and 1.7 folds, respectively. There are two miR-146 paralogous genes in human, mouse and rat genomes, miR146a and miR-146b, which share the same seed sequence with only two-nucleotide differences. To examine whether miR-146b also is upregulated, qRT-PCR was performed and confirmed that miR-146b was significantly upregulated by 1.5 folds ($p<0.02$) in RECs of diabetic rats compared to normal control.

NF-κB is a key regulator of inflammatory, immune responses and microvascular functions. Activated NF-κB induces expression of a wide range of downstream target genes, including many proinflammatory mediators, contributes to diabetes-induced apoptosis of RECs and pericytes and the pathogenesis of DR. NF-κB is activated in the retina as early as two months after the onset of diabetes. Therefore, upregulation of miR-146, miR-155, miR-132 and miR-21 in RECs of diabetic rats may be a result of NF-κB activation in the retina, reflecting the ongoing NF-κB activation and subsequent inflammatory responses in the retina and RECs of STZ-induced diabetic.

These NE-KB-responsive miRNAs are not only induced by NF-κB, and in turn, most of them may inhibit NF-κB activation by targeting key components of various NFKB activation pathways, forming feedback regulatory loops. miR-146 inhibits NF-κB activation by directly targeting two key adaptor/scaffold proteins, IL-1 receptor associated kinase (IRAK1) and TNF receptor-associated factor 6 (TRAF6), of the MyD88-dependent IL-I R/Toll-like receptor (TLR)-mediated NF-κB activation pathway, while miR-21 may inhibit NF-κB activation through targeting PDCD4, which promote activation of NF-κB by an unknown mechanism. miR-155 may target and downregulate the expression of angiotensin II type 1 receptor, $AT_1R$, potentially inhibiting Ang II-induced NF-κB activation.

11. miRNAs potentially regulating VEGF and microvascular functions (miR-20a, miR-20b, miR-15b, miR-16, miR-125a and miR-378) are significantly changed in RECs and may be used as novel therapeutic targets for the treatment of diabetic retinopathy through their regulation on VEGF. VEGF is a potent mitogen promoting endothelial survival, proliferation, migration, angiogenesis and endothelial permeability, playing important roles in the development of DR. The 3'UTR of VEGF transcripts have target sites for about 100 different miRNAs, suggesting that miRNAs also modulate VEGF expression. In vitro studies in tumor cell lines implicated that miR-20a, miR-20b, miR-15b, miR-16, miR-125a and miR-378 may target their binding sites in the 3'UTR of VEGF transcript and regulate its expression. Among these, miR-20a, miR-15b and miR-16 are upregulated, while miR-20b and miR-125a are downregulated in RECs of diabetic rats compared to normal controls; however, in the neuroretina, both miR-125a and miR-378 are upregulated in the neuroretina, suggesting potential regulatory roles of different miRNAs on VEGF expression in different cell types. It appears that the miR-17-1-92 cluster may both be induced by VEGF and mediate its angiogenic functions, and in turn, member of miR-17-1-92 cluster may target VEGF, suggesting a negative feedback loop, fine-tuning the expression and function of VEGF.

Increasing evidence has shown that miRNAs play important roles in the regulation of NF-κB activation, as well as mediating its downstream functions. Evidence that miR-146 is induced by thrombin in a NF-κB activation-dependent manner (FIG. 23). In addition, a new target gene of miR-146, CARD10, which is a key scaffold protein in GPCR-mediated NF-κB activation pathway was identified (FIG. 22). Furthermore, miR-146 inhibits thrombin-induced NF-κB activation [FIGS. 24(A) and (B)] and subsequent increased leukocyte adhesion to endothelial cells [FIGS. 24(C) and (D)] through its repression on CARD10 and possibly other molecules involved in the pathway, e.g. TRAF6. These results suggest that, in addition to the negative feedback regulation on IL-1R/TLR-mediated NF-κB activation, miR-146 also imposes negative feedback regulation on GPCR-mediated NF-κB activation (FIG. 25).

GPCRs constitute one of the largest families of cell surface receptor proteins. It is estimated that up to 2% of the human genome encodes GPCRs. GPCRs are expressed in all organ systems throughout the body and accounts for targets of 40-50% of modern drugs. A large varieties of ligands, including thrombin, LPA, Ang II, ET-1, PAF, IL8, and SDF, engage their GPCRs and induces NF-κB activation to regulate pro-inflammatory reactions and many other diverse cellular functions, including cellular survival, proliferation and neural plasticity, as well as tumorigenesis and metastasis. A CARD10-Bcl10-MALT1 signalosome has been proven to be a common pathway of GPCR-mediated NF-κB activation. Therefore, the negative feedback regulation on GPCR-mediated NF-κB through targeting CARD10 that was demonstrated in HRECs may provide a new general mechanism for negative regulation of GPCR-mediated NF-κB activation to maintain tissue homeostasis, which is critical for normal development and physiological functions.

Uncontrolled NF-κB activation promotes tumor growth and invasion in tumorigenesis, and contributes to autoimmunity and inflammation-associated tissue damage and diseases. Restoration of homeostasis of NF-κB pathways may efficiently prevent or alleviate these disease processes. To demonstrate the functional consequences, trans-endothelial electrical resistance (TEER) assays were performed. In this system, endothelial cells are grown as a monolayer on small gold electrodes. Normally they form tight cell-cell junction and exhibit TEER, which reflects endothelial barrier function and permeability. Defects in endothelial junctions result in a decrease of TEER. IL-1β treatment induced NF-κB-dependent significant decrease of TEER, suggesting IL-1β-induced NF-κB activation resulted in endothelial functional defects (FIG. 30). However, when RECs were transfected with miR-146a mimics before IL-1β treatment; overexpression of miR-146a significantly prevented IL-1β-induced decrease of TEER, suggesting that miR-146a inhibited IL-1β-induced damage to the barrier function of RECs.

miR-146 inhibited thrombin-induced NF-κB activation and key NF-κB downstream genes, and more importantly, it inhibited subsequent increased leukocyte adhesion to endothelial cells. Leukostasis is considered as one of the early events in many inflammation-involved vascular diseases, e.g. atherosclerosis and diabetic retinopathy. Results support that miR-146 is a new target for drug development for the treatment and/or prevention of these diseases.

In addition to GPCR-mediated NF-κB activation, recently CARD10 was also shown to be required for epidermal growth factor receptor (EGFR)-induced NF-κB activation in cancer cell lines and mouse embryonic fibroblasts (MEFs), and modulates EGFR-associated proliferation, survival, migration and invasion of cancer cells. EGFR belongs to receptor tyrosine kinase (RTK) superfamily, receptors for growth factors. Other growth factors, e.g. fibroblast growth factor (FGF), platelet-derived growth factor (PDGF), insulin-like growth factor (IGF), have been shown to activate NF-κB through specific RTKs; and CARD10 may also be utilized in the pathways of NF-κB activation by these growth factor. Therefore, miR-146 may also act as a negative feedback regulator of RTK-mediated NF-κB activation. miR-146 likely plays important roles in modulation of NF-κB activity through multiple pathways in a wider range of signaling context and cellular functions.

EXAMPLES

Example 1

Systemic identification of miRNAs involved in early DR. To understand the roles of miRNAs in early DR, the STZ-induced diabetic rat model was used and the neuroretina and RECs (by magnetic cell sorting with anti-PECAM-1 antibody) from STZ-induced diabetic and normal control rats three months after the onset of diabetes. Subsequently, total RNA, was prepared and miRNA expression profiling was performed using Taqman miRNA microarrays. Data showed that 357 and 358 miRNAs are expressed in the neuroretina, while 222 and 217 miRNAs are detected in RECs of normal control and diabetic rats, respectively. By comparing the miRNA transcriptomes of diabetic rats to the ones of normal controls, at least 87 miRNAs were identified that are differentially expressed (81 up- and 6 downregulated, p<0.01) in the neuroretina, and 120 miRNAs that changed significantly (16 up- and 104 downregulated, p<0.01) in RECs of diabetic rats compared to normal controls. Functional annotation analysis revealed that many of the differentially expressed miRNAs are known to play important roles in multiple pathogenetic pathways related to DR, including leukostasis and inflammation, integrity of endothelial cells and angiogenesis, cell cycle and apoptosis. This is, by far, the first direct report on miRNAs in DR, providing one of the first insights in the roles of miRNAs in the pathogenesis of DR.

Example 2

NF-κB-responsive miRNAs are upregulated in RECs of diabetic rats, suggesting activation of NF-κB in diabetic RECs. miR-21, miR-146a/b, miR-132 and miR-155 have been shown to be downstream of NF-κB and upregulated in various cell types in a NF-κB-dependent manor Among the differentially expressed miRNAs in RECs, all of these known NF-κB-responsive miRNAs are confirmed by quantitative (q)RT-PCR assays to be significantly upregulated in RECs of diabetic rats compared to normal controls (FIG. 9), suggesting that NF-κB is upregulated in RECs of diabetic rats, which is consistent with several previous reports that NF-κB is activated as early as two months after the onset of diabetes.

Example 3

Figures 10A, 10B, 10C, 10D:
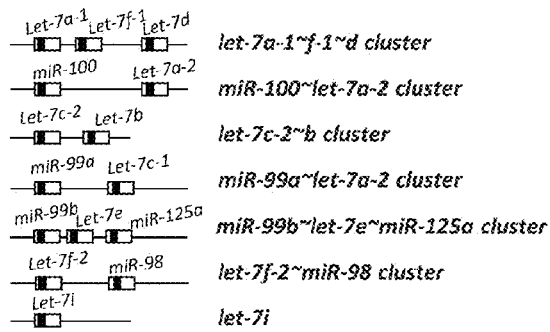
FIGS. 10A-D show expression of members of the let-7 family are significantly changed in RECs of STZ-induced diabetic rats compared to normal controls. (10A) Sequence alignments of the mature miRNA sequences (SEQ ID NOS 71-78, respectively, in order of appearance) of the members of the let-7 family. The rectangular shaded box across all miRNAs marks the seed sequence of each miRNA. (10B) Diagram of seven (cluster) genes encoding members of the let-7 family in rat genome; (10C) Relative expression (ΔCt) of members of the let-7 family in RECs (snRNA U6 was used as control. ΔCt=CtmiR-CtU6); (10D) Members of the let-7 family are differentially expressed in the RECs of STZ-induced diabetic rats, compared to the ones of normal control rats.

Members of the let-7 family are downregulated in RECs of diabetic rats: Among miRNAs which are downregulated in RECs of diabetic rats, multiple members of the let-7 family were significantly decreased in RECs of diabetic rats by 1.6-4.9 folds, including let-7b, c, e and g (FIG. 10), suggesting that let-7 family may be involved in the pathogenesis of early DR.

In the let-7-involved NF-κB-activation feedback loops (FIG. 9), let-7 is downregulated by NF-κB through Lin28, which inhibits maturation of let-7. Data indicated that, in RECs of diabetic rats, let-7 is downregulated, while NF-κB is activated, supporting that downregulation of let-7 may be a result of NF-κB activation, and that let-7-involved positive feedback loops activating NF-κB may be activated in RECs of diabetic rats.

Example 4

Figure 11:
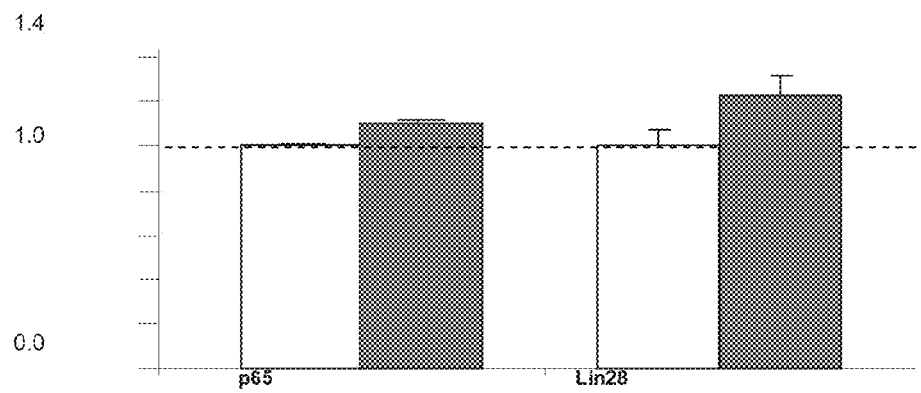
FIG. 11 shows relative expression level of p65 and Lin28 in RECs under 5 mM (■) (NG) and 30 mM glucose (□) (HG). The levels of expression were normalized to the ones of NG. n=3. *: $p<0.05$; **: $p<0.01$.

Lin28 may be upregulated in RECs in high glucose culture, while NF-κB is activated. TR-iBRB REC cells were treated with either 5 mM (NG) or 30 mM glucose (HG) for 24 hours. qRT-PCR assays showed that, the p65 of NF-κB subunit was significantly upregulated, suggesting NF-κB upregulation and activation (FIG. 11); and Lin28 also was upregulated, supporting that activated NF-κB may transactivate Lin28, and that let-7-involved NF-κB-activation positive feedback loops may be activated in RECs in HG.

Example 5

Inactivation of NF-κB by antioxidant diet may inactivate the feedback loop in diabetic RECs. Hyperglycemia-induced increased ROS play important roles in NF-κB activation, endothelial damage and diabetic complications; administration of antioxidants may inhibit NF-κB activation in the retina of diabetic rats. Therefore, antioxidant diets are used to inactivate NF-κB in diabetic retina and examine its effect on the let-7-involved positive feedback loops. Young adult male Sprague-Dawley rats (~300g) are randomly assigned to five experimental groups with at least 6 rats in each group: Group I (GC) as described herein; Group II (PC) as described herein. Group III (PC+diet): PC rats on diet supplemented with multiple antioxidants (ascorbic acid, 1 g/kg; Trolox 500 mg/kg; dl a-tocopherol acetate, 250 mg/kg; N-acetyl cysteine, 200 mg/kg, β-carotene, 45 mg/kg, and selenium, 0.1 mg/kg of diet) for twelve months. Group IV (PC-GC): rats with 6-month PC followed by 6-month GC, as described herein. Group V (PC-GC+diet): rats with 6-month PC followed by GC and antioxidant diet for 6 months. Subsequently, the expression and activity of NF-κB and other components of the positive feedback loops in RECs are examined. Diabetes-induced microvascular defects, including breakdown of BRB, capillary degeneration are among the earliest vascular histopathology of DR. And NF-κB activation contributes to apoptosis of RECs and pericytes and increased microvascular permeability in diabetic rats. To evaluate the effect of inactivation of NF-κB-activation feedback loops on the development of DR, the following two assays are performed: 1) Evaluation of BRB breakdown by Evans blue assays, in which Evans Blue dye leaked from the blood into the retina is measured to reflect BRB breakdown; 2) Evaluation of apoptosis of RECs and endothelial degeneration by quantification of acellular capillaries and pericyte ghosts.

In Group II (PC) rats, NF-κB is activated because of uncontrolled hyperglycemia; NF-κB downstream genes, including NF-κB-responsive miRNAs are upregulated; let-7-involved positive feedback loops are activated with increased expression of Lin28, downregulation of let-7 and increased expression of IL-6 and Ras compared to Group I (GC) rats. Functionally, there is increased Evans blue retention in the retina and increased acellular capillaries and pericyte ghosts in PC rats. In RECs of Group III (PC+diet) rats, antioxidant diet may inhibit the activation of NF-κB, compared to Group II (PC) rats. Consequently, let-7-involved positive feedback loops may be inactivated, therefore, decreased expression of Lin28, upregulation of let-7 and decreased expression of IL-6 and Ras, compared to Group II (PC) rats; and the levels of NF-κB, Lin28, Let-7, IL-6 and Ras may be comparable to Group I (GC) rats. Functionally, there are decreased levels of Evans blue retention, and decreased acellular capillaries and pericyte ghosts in Group III (PC+diet) rats, compared to Group II (PC) rats. Activation of let-7-involved positive feedback loops is dependent on hyperglycemia-induced NF-κB activation, and it contributes to diabetes-induced REC damage; inactivation of NF-κB in vivo may inactivate the self-perpetuating feedback loops and prevent diabetes-induced vascular damage.

In RECs of Group IV (PC-GC) rats, hyperglycemia-induced NF-κB and let-7-involved NF-κB-activation positive feedback loops remain activated. In RECs of Group V (PC-GC+diet) rats, as antioxidant diet inhibits NF-κB activation, NF-κB is inactivated; expression of NF-κB and/or its downstream genes, including NF-κB-responsive miRNAs are downregulated; let-7-involved NF-κB-activation positive feedback loops may be inactivated with Lin28 downregulated, let-7 upregulated and IL-6 and Ras downregulated, compared to Group IV (PC-GC) rats. Functionally, the levels of Evans blue retention, acellular capillaries and pericytes ghosts in the retina are decreased, compared to Group IV (PC-GC) and Group II (PC) rats. These results support that let-7-involved NF-κB-activation positive feedback loops play important roles in metabolic memory in RECs of DR. Inactivation of NF-κB activation by antioxidant diet may interrupt the positive feedback loops and "erase" metabolic memory in vivo.

Example 6

Inactivation of endogenous let-7 by systemic administration of anti-miR-let7. Locked nucleic acid (LNA)-modified anti-miRs can efficiently knock down specific miRNAs in vivo for as long as 7 weeks after injection. Therefore, LNA-modified LNA-anti-let-7 are employed to inactivate endogenous let-7 in RECs in vivo by tail-vein injections. Young adult male Sprague-Dawley rats (~300g) are divided into 8 groups with at least 6 rats in each group. Group I and II (GC): STZ-induced diabetic rats with GC for 6 (Group I) and 12 months (Group II); Group III and IV (PC+LNA-anti-let-7b) and Group V and VI (PC+neg ctl anti-miR): diabetic rats with PC and injected with LNA-anti-let-7 (Group III and IV) or LNA-negative control anti-miR (Group V and VI) for 6 (Group III and V) and 12 months (Groups IV and VI), respectively. Group VII (PC-GC+LNA-anti-let7b) and Group VIII (PC-GC neg ctl anti-miR): diabetic rats with 6-month PC, followed by 6-month GC with injection of LNA-anti-let-7b or negative control anti-miR for 6 months. Subsequently, the expression and activity of NF-κB and other components of the positive feedback loops are examined, and BRB breakdown and capillary degeneration are evaluated by Evans blue assays, and counting of acellular capillaries and pericyte ghosts. As discussed herein, anti-let-7b is used because let-7b is highly expressed and changed the most in its expression level among all members of the let-7 family in RECs of STZ-induced diabetic rats compared to controls (FIG. 3), therefore, may represent the major functions of let-7 family in RECs.

In RECs of Group V and VI (PC+neg ctl anti-miR) rats, negative control anti-let-7 has no effect on the positive feedback loops, hyperglycemia-induced NF-κB activation and let-7-involved NF-κB-activation positive feedback loops, compared to Group I and II (GC) rats. In RECs of Group III and IV (PC+LNA-anti-let-7) rats, further decreased expression of let-7 because of the inhibition by LNA-anti-let-7, and further increased upregulation of IL-6 and Ras, NF-κB activation, compared to Group V and VI (PC+neg ctl anti-miR) rats at each time point. Evans blue retention in the retina, numbers of acellular capillaries and pericytes ghosts also may be increased and appear earlier or accelerated compared to Group V and VI rats, suggesting that inhibition of endogenous let-7 by LNA-anti-1et7 may enhance the positive feedback loops and NF-κB-activation, exacerbating the progression of DR.

In Group VII (PC-GC+LNA-anti-let7) rats, LNA-anti-1et7 may inhibit endogenous let-7 during the secondary GC period, therefore further enhancing the NF-κB-activation feedback loops through upregulation of IL-6 and Ras, therefore, increasing levels of NF-κB activation, IL-6, Ras and Lin28, compared to Group VIII (PC-GC+neg_ctl anti-miR) rats. Evans blue retention in the retina, numbers of acellular capillaries and pericytes ghosts also may be increased, suggesting that inhibition of endogenous let-7 by LNA-anti-1et7 enhances the NF-κB-activation positive feedback loops, therefore, enhances metabolic memory of PC in RECs.

Example 7

Overexpression of let-7 by intraocular injection of let-7-expressing lentivirus. To overexpress let-7 in the retina and RECs, intraocular injection of let-7b expressing lentivirus is employed (System Biosciences Inc. SBI), as lentivirus can efficiently infect both dividing and non-dividing cells in wide range of mammalian cells. In this experiment, 5 groups of rats are used: Group I (GC) as described above; Group II (PC+lentivirus expressing let-7b) and Group III (PC+neg ctl lentivirus): STZ-induced diabetic rats with 12-month PC and intraocular injection of lentivirus expressing let-7 and negative control lentivirus, respectively. Group IV (PC-GC+lentivirus expressing let-7b) and Group V (PC-GC+neg ctl lentivirus): STZ-induced diabetic rats with 6-month PC, followed by 6-month GC with intraocular injection of lentivirus expressing let-7 and negative control lentivirus at the start of secondary GC condition, respectively.

In RECs of Group III (PC+neg ctl lentivirus) rats, negative control lentivirus may have no effect on let-7 expression, therefore, NF-κB and let-7-involved NF-κB-activation positive feedback loops are expected to be activated because of hyperglycemia, compared to Group I(GC) rats. However, in RECs of Group II (PC+lentivirus expressing let-7b) rats, overexpression of let-7 by infection with let-7b-expressing lentivirus may result in downregulation of IL-6 and Ras, inactivating NF-κB or decreasing NF-κB activation, therefore, decreased levels of NF-κB activation, IL-6, Ras and Lin28, compared to Group III (PC+neg ctl lentivirus) rats. Evans blue retention in the retina, numbers of acellular capillaries and pericytes ghosts may be significantly decreased, compared to Group III rats, suggesting that overexpression of let-7 may inactivate the positive feedback loops, and prevent the progression of DR.

In Group IV (PC-GC+lentivirus expressing let-7b) rats, overexpression of let-7 during the secondary GC period may inactivate the NF-κB-activation positive feedback loops through downregulation of IL-6 and Ras, therefore, decreased levels of NF-κB activation, IL-6, Ras and Lin28 in RECs of Group IV (PC-GC+lentivirus expressing let-7b) rats, compared to Group V (PC-GC+neg ctl lentivirus) rats. Evans blue retention in the retina, numbers of acellular capillaries and pericytes ghosts also may be decreased in Group IV rats, compared to Group V rats, suggesting that introduction of extra let-7 may inactivate the NF-κB-activation positive feedback loops during GC period and erase or decrease metabolic memory, therefore, may be used as therapeutic target for the treatment of DR.

Example 8 miR-146a/b inhibits NF-κB. miR-146a/b inhibits the expression of key molecules of NF-κB activation pathways, including IRAK1, TRAF6 and CARD10, in retinal endothelial cells. Therefore, miR-146a/b is useful to inhibit the NF-κB activity for the treatment of diabetic retinopathy.

In human retinal endothelial cells, miR-146a also inhibits IL-1β-induced NF-kB activation by repressing IRAK1 and TRAF6 (FIG. 18).

Figure 19A:
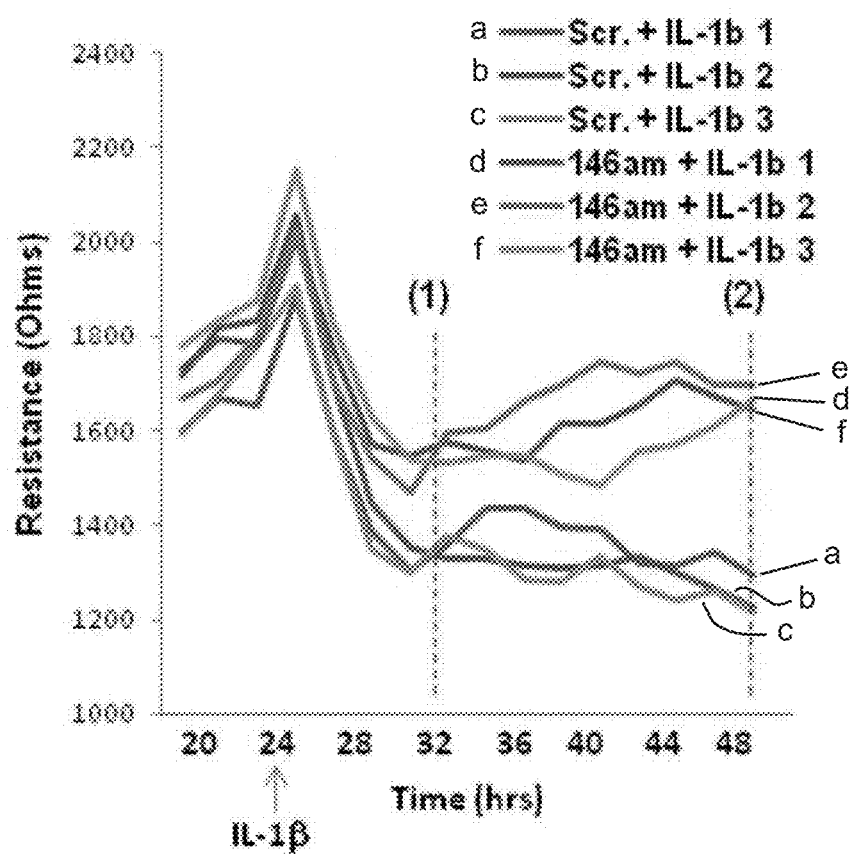
FIGS. 19A-C show treatment of human retinal endothelial cells (HRECs) results in decrease of trans-endothelial electric resistance (TEER); and overexpression of miR-146a prevents IL-1b-induced TEER decrease; HRECs are transfected with miR-146a mimics or scrambled (scr) oligonucleotides (10 nM) as negative control; 20 hours after transfection, TEER recording started; (19A) at 24 hours, the cells were treated with IL-1β (10 ng/ml); (19B-C) normalized TEERs show that overexpression of miR-146a prevented IL-1b induced decrease of TEER. : p<0.01; *: p<0.001, where y: no treatment; z: IL-1b+scrambled oligos; x: IL-1B+miR-146a mimics.
Figures 19B, 19C:
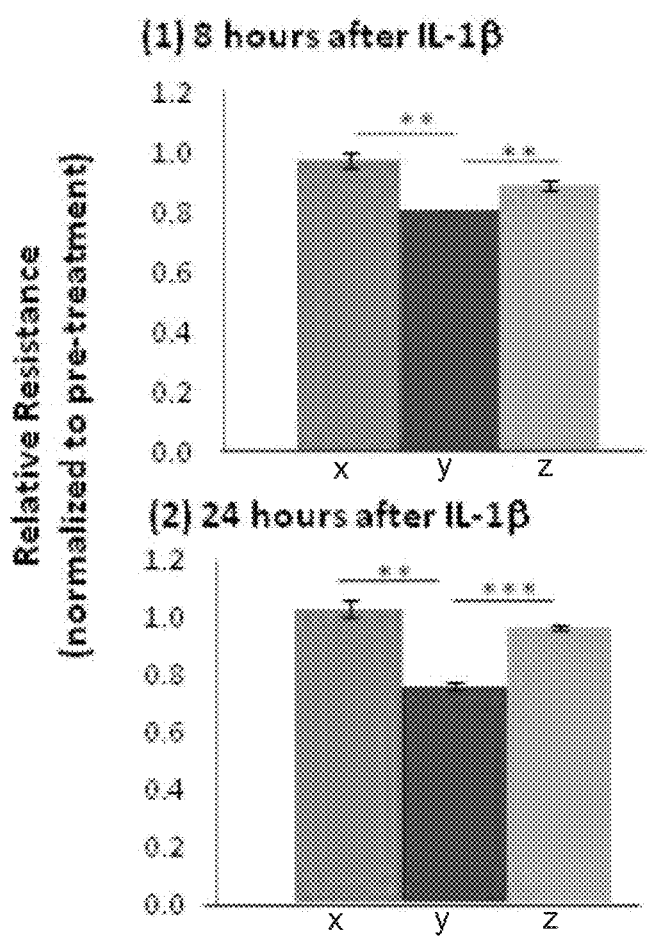

More importantly, miR-146a inhibits IL-1β-induced decrease of transendothelial electrical resistance (TEER) in human endothelial cells, which indicates the breakdown of the integrity of endothelial junctions and dysfunction of endothelial cells (FIG. 19). This result substantiates that miR-146 is useful as therapy for treatment of diabetic retinopathy. This function may also be used for inhibition of NF-κB activation to suppress inflammatory responses caused by NF-κB activation in the treatment of other diseases, e.g. age-related macular degeneration, diabetic nephropathy, infection, atherosclerosis, and so forth.

Previously, by target prediction, miR-146 was predicted to target CARD10, which is a key molecule in G-protein coupled receptor (GPCR)-mediated NF-κB activation pathway. Ligands of GPRC include angiotensin II, endothelin-1, lysophosphatidylcholine (LPC), lysophosphatidic acid (LPA), platelet-activating factor (PAF) and thrombin, and the like. GPCR mediated NF-κB activation plays important roles in inflammation, diabetic retinopathy, diabetic nephropathy, atherosclerosis, inflammatory bowel disease, and so forth. miR-146a targets CARD10 as shown by luciferase reporter assay (FIG. 20). miR-146a directly inhibits the expression of endogenous CARD10 in human retinal endothelial cells (FIG. 21).

Example 9

Figure 22A:
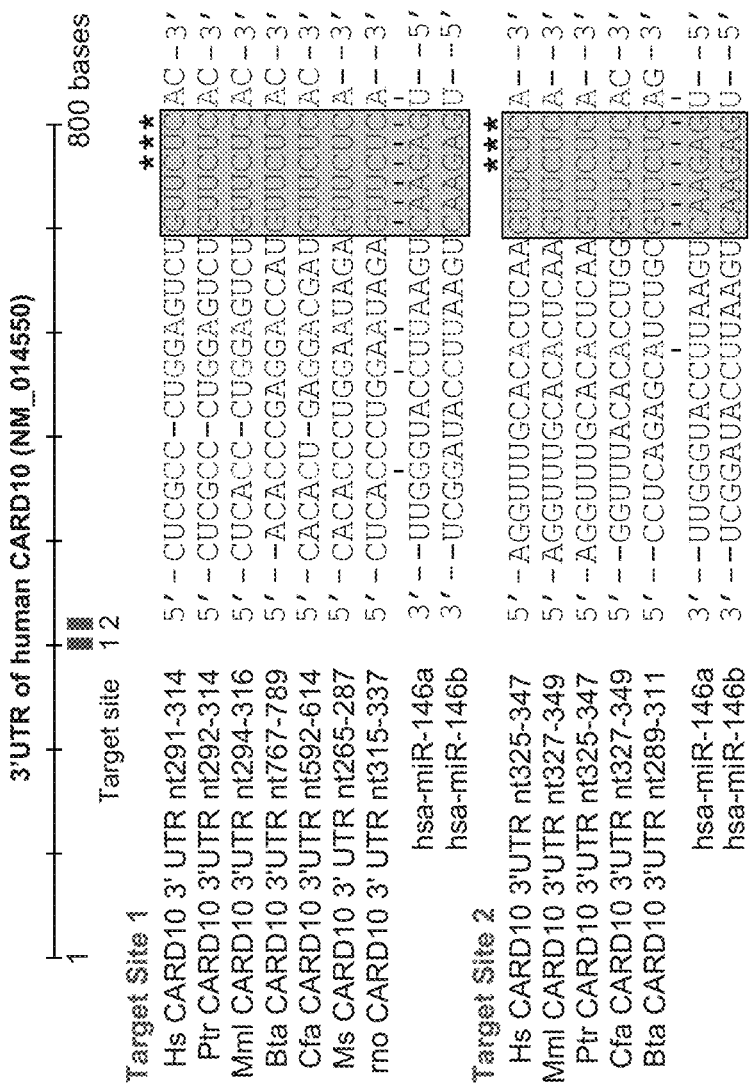
FIGS. 22A-D presents the 3'UTR of human CARD10 (NM_014550)

Negative feedback regulation of G-protein coupled receptor-mediated NF-κB activation pathway by miR-146. miRNAs are involved in diabetic retinopathy. miR-146 was upregulated in RECs of diabetic rats compared to wild type controls, as a result of NF-κB activation in diabetic retina. In search of predicted target sites for miR-146 (TargetScan.org), CARD10, also known as CARD-containing membrane-associated guanylate kinase (Maguk) protein 3 (CARMA3) is a predicted target of miR-146 (FIG. 22). There are at least two predicted target sites for miR-146 in the 3' untranslated region (UTR) of the transcripts of human CARD10 [NM_014550. FIG. 22(A)]. CARD10 is a novel scaffold protein and indispensable adaptor molecule mediating GPCR-mediated NF-κB activation. This observation suggests that, in addition to IL-1R/TLR mediated NF-κB activation pathway, miR-146 may also regulate GPCR-mediated NF-κB activation through modulating CARD10. The 3'UTR of human CARD10 (796 bp) downstream of the firefly luciferase (FL) cassette of the luciferase reporter vector, CmiT00001-MT01 [Genecopoeia. FIG. 26(A)], was subcloned and a luciferase reporter assay was performed. Results showed that co-transfection of miR-146a mimics in primary human retinal endothelial cells (HRECs) significantly reduced FL activity [FIG. 22(B)], suggesting miR-146 targets human CARD10 3'UTR.

To test the specificity of this targeting event, target site 2 was mutated, which is considered as a conserved predicted target site in TargetScan prediction, by replacing the sequence complementary to the first three residues of the seed sequence of miR-146 (CTC) to AAA (Wt1+Mut2 [FIG. 22(A)] supplemental sequences). Surprisingly, as in the wild type construct, miR-146a mimics significantly repressed the luciferase activity from the construct with mutant target site 2 [FIG. 22(B)], suggesting that miR-146 does not target CARD10 through target site 2; instead, target site 1 may be the functional target site for miR-146 in HRECs. Both predicted target sites were mutated, and luciferase reporter assays were performed using construct with double mutations [Mut2+Mut2, FIG. 22(A)]. When both target sites were mutated, miR-146 completely lost its repression on the luciferase activity, suggesting that miR-146 target CARD10 specifically through target site 1. Consistently, sequence alignment showed that target site 1 appeared to have broader conservation among different species. Luciferase assays in HEK293 cells produced similar results, further supporting that miR-146 targets CARD10, through the first predicted target site [FIG. 26(B)]. Intriguingly, repression of the luciferase activity by miR-146 appeared to be significantly higher in the construct with mutation in target site 2 only (Wt1+Mut2), compared to the wild type construct. This may suggest that mutant site 2 may negatively influence the efficiency of functional targeting through target site 1. Moreover, when both predicted sites were mutated (Mut1+Mut2), the luciferase activity was not only dis-inhibited, but was even slightly higher than the negative control for the wild type construct (Wt1+Wt1/scrambled oligo) (FIG. 22(B); FIG. 27), suggesting that luciferase construct with wild type CARD10 3'UTR may have been targeted by endogenous miR-146 in HRECs (FIG. 29).

Figure 22C:
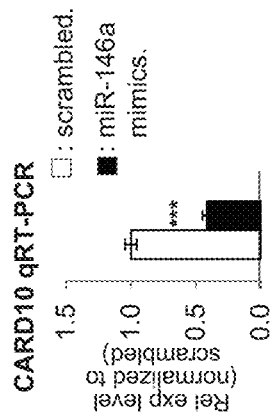
Figure 22D:
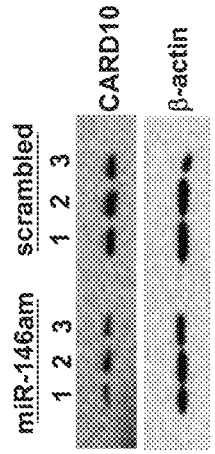
Figure 22B:
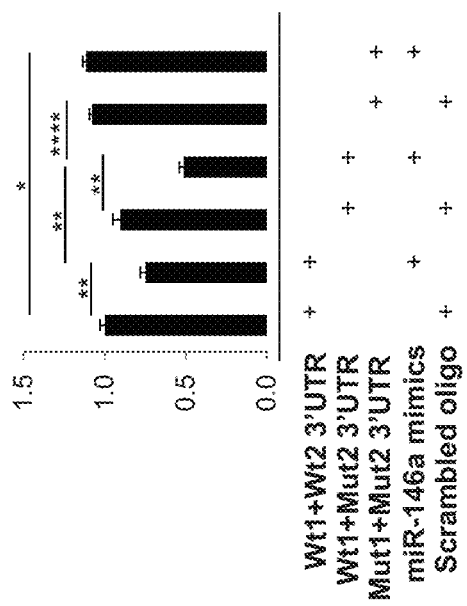
Figures 23A, 23B:
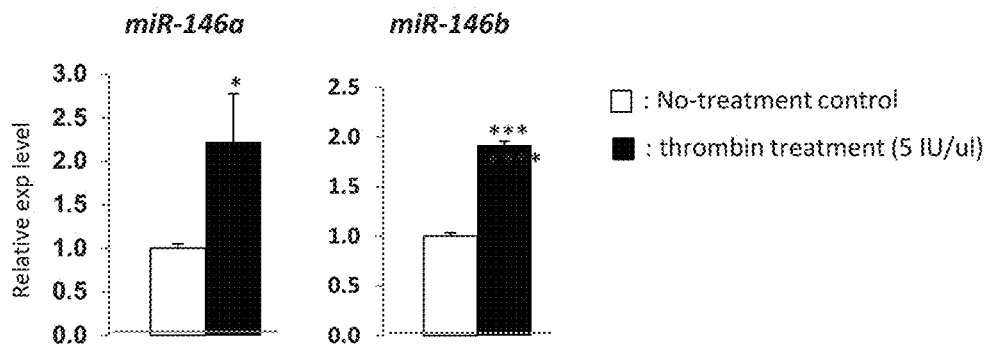
Figures 23C, 23D, 23E:
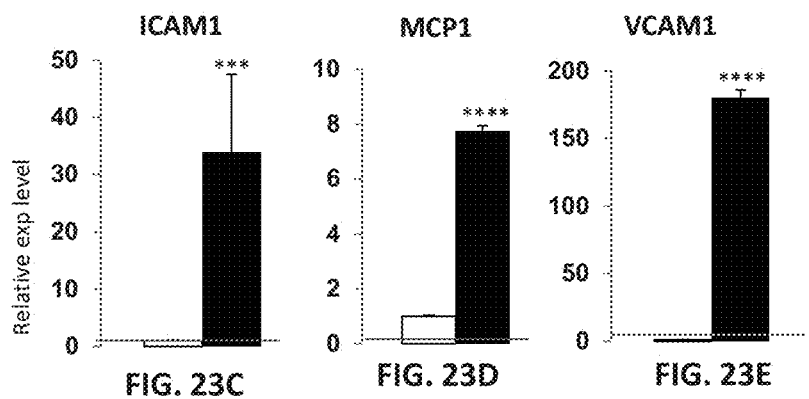
Figure 23F:
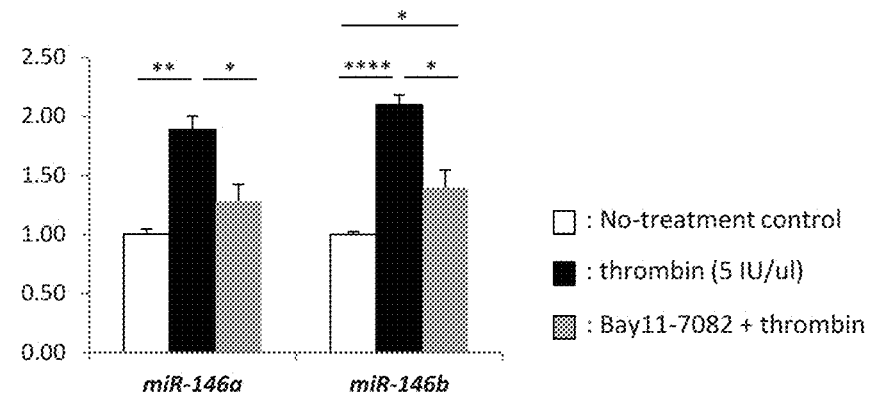
Figure 24A:
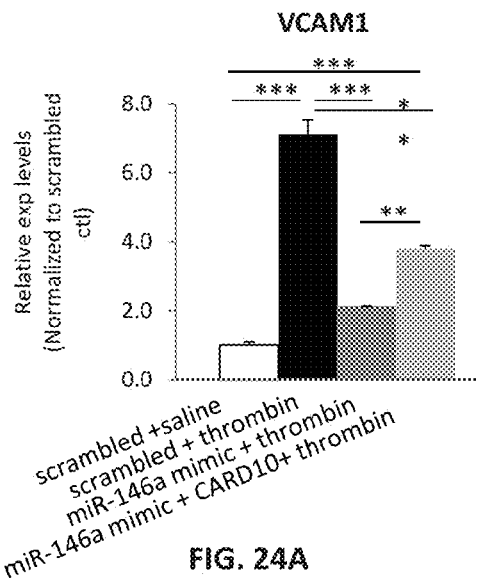
Figure 24B:
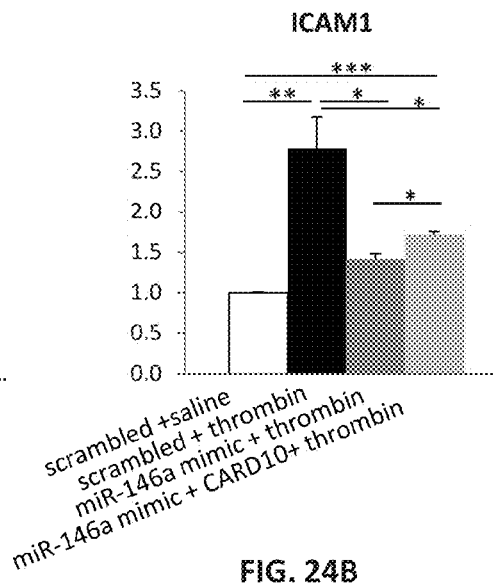
Figure 24C:
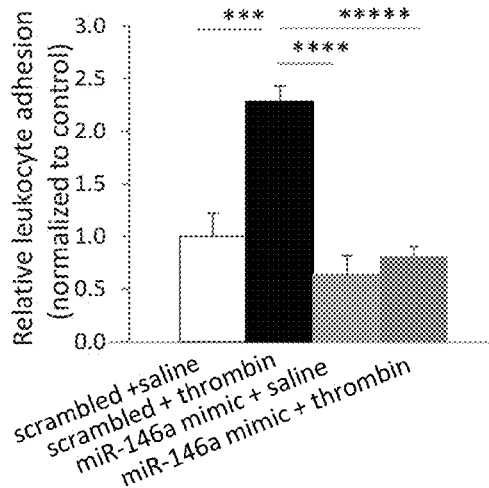
Figure 24D:
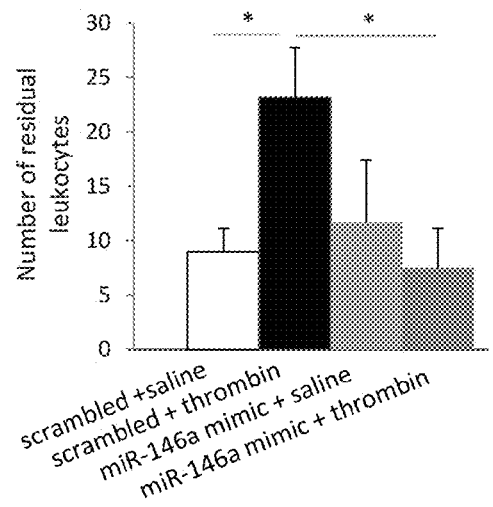

To demonstrate that miR-146 inhibits endogenous CARD10 in HRECs, miR-146a mimic in HRECs was overexpressed, and CARD10 expression was significantly decreased at both mRNA and protein levels [FIGS. 22(C) and and (D)], suggesting that miR-146 targets endogenous CARD10 in HRECs.

miR-146 is a NF-κB-responsive miRNA, and can be induced by IL-1R/TLR mediated NF-κB activation. GPCR-mediated NF-κB activation also induces the expression of miR-146. HRECs were treated with thrombin, which has been shown to activate NF-κB predominantly through a GCPR—the Protease-Activated Receptor (PAR)-1 and Gαq in endothelial cells. Results showed that thrombin treatment significantly upregulated both miR-146a and miR-146b in HRECs by 122% and 92%, respectively [FIGS. 23(A) (B)]. Meanwhile, well-known NF-κB downstream genes in endothelial cells, including ICAM1, MCP1 and VCAM1 were significantly upregulated [FIGS. 23 (C), (D), (E); FIG. 27].

Upregulation of miR-146a/b by thrombin treatment is a result of NF-κB activation. HRECs were pretreated with a NF-κB specific inhibitor, Bay11-7082 (3 μM), which irreversibly inhibits IκBα phosphorylation, for 30 minutes, prior to thrombin treatment. Results showed that inactivation of NF-κB by Bay11-7082 completely blocked thrombin-induced upregulation of miR-146a, and significantly inhibited miR-146b upregulation (by at least 33%) [FIG. 23(C) (E)], suggesting that thrombin-induced upregulation of miR-146 is mostly a result of thrombin-induced NF-κB activation.

Thrombin-dependent NF-κB activation is mediated by the CARD10-Bcl10-MALT1 signalosome. If miR-146 targets CARD10, one of the key components of the signalosome of the GPCR-mediated NF-κB activation pathway, miR-146 should have an inhibitory effect on GPCR-mediated NF-κB activation in HRECs. HRECs were transfected with miR-146a mimic or negative control oligos with scrambled sequences; 24 hour after the transfection, the cells were treated with thrombin. In negative control scrambled oligo-treated cells, thrombin treatment resulted in dramatic induction of NF-κB downstream genes, ICAM-1 (by ~17 fold) and VCAM-1 (by ~95 fold); while overexpression of miR-146a efficiently inhibited thrombin-induced upregulation of ICAM-1 and VACM-1, decreased by ~74% and ~57%, compared to scrambled control treated cells respectively [FIG. 24(A)], suggesting that miR-146 inhibited thrombin-induced NF-κB activation.

To determine whether miR-146's inhibition on thrombin-mediated NF-κB activation is mediated by its repression on CARD10, HRECs were transfected with human CARD10-expressing constructs (Genecopoeia) before miR-146a mimic transfection and thrombin treatment. Overexpression of CARD10 resulted in partial rescue of miR-146's inhibition on NF-κB dependent expression of VCAM1 (by 34%) and ICAM1 (by ~22%), respectively (FIGS. 24(A) and (B) and FIG. 28), supporting that downregulation of CARD10 contributed to miR-146's inhibition on thrombin-induced NF-κB activation. However, overexpression of CARD10 did not rescue the repressive effect of miR-146 on thrombin-mediated NF-κB activation, suggesting that other component(s) of thrombin-mediated NF-κB activation pathway may be also targeted by miR-146. TRAF6 may also be recruited to the CARD10-Bcl10-MALT1 complex, and is required for GPCR-mediated NF-κB activation; TRAF6 is a target of miR-146. qRT-PCR analysis on HRECs transfected with miR-146a mimic showed that TRAF6 is significantly downregulated (FIG. 28), suggesting that continued repression of TRAF6 by miR-146 may contribute to the incomplete rescue effect of overexpression of CARD10 on the inhibition of thrombin-induced NF-κB activation by miR-146. Overall, results suggest that GPCR-mediated NF-κB activation induces expression of miR-146a/b, which in turn can inhibit this pathway by targeting key adaptor molecule(s), including CARD10, suggesting a negative feedback regulatory mechanism on GPCR-mediate NF-κB activation.

Thrombin-induced NF-κb activation results in upregulation of ICAM-1 and VCAM-1, key docking proteins for leukocyte adhesion to endothelial cells, which leads to increased leukocyte/endothelial adhesion. Leukostasis is considered early event in the pathogenesis of diabetic retinopathy, atherosclerosis and other chronic inflammation-related vascular diseases. If miR-146 inhibits thrombin-mediated NF-κB activation, it should also inhibit thrombin-induced leukocyte adhesion to endothelial cells. Leukocyte adhesion analysis was performed by incubating miR-146 mimic-transfected HRECs with Calcein-labeled leukocytes. Results showed that in scrambled control-treated HRECs, thrombin treatment significantly increased leukocyte adhesion [FIGS. 24(C) and (D)]. Overexpression of miR-146 completely suppressed thrombin-induced increase of leukocyte adhesion, suggesting that miR-146 may inhibit GPCR-mediated NF-κB activation-induced inflammatory response of HRECs.

Example 10 miR-146 affects EGF induced NF κB activation. MiR-146 may inactivate EGF induced NF-κB activation in cancer cells, and may be a new therapeutic target for the treatment of cancer in which NF-κB activation plays a major role in tumor survival, proliferation, migration and invasion. In addition to GPCR-mediated NF-κB activation, recently CARD10 is also shown to be required for epidermal growth factor receptor (EGFR)-induced NF-κB activation in cancer cell lines and mouse embryonic fibroblasts (MEFs), and modulates EGFR-associated proliferation, survival, migration and invasion of cancer cells. In estrogen receptor-negative breast cancers, many have elevated level of EGFR; and EGF-induced NF-κB activation plays critical roles in tumor survival, proliferation and migration and invasion. EGFR belongs to receptor tyrosine kinase (RTK) superfamily, receptors for growth factors. Other growth factors, e.g. fibroblast growth factor (FGF), platelet-derived growth factor (PDGF), insulin-like growth factor (GF), have been shown to activate NF-κB through specific RTKs; and CARD10 may also be utilized in the pathways of NF-κB activation by these growth factor. If so, we predict that miR-146 may also act as a negative feedback regulator of RTK-mediated NF-κB activation (FIG. 25); and overexpression of miR-146 can inhibit cancer survival, proliferation, migration, invasion in cancers, e.g., ER-negative breast cancer, in which NF-κB activation plays a major role in tumorgenesis.

MATERIALS AND METHODS

Diabetic rat model. All animal protocols have been reviewed and approved in accordance with the policies of the Institutional Animal Care and Use Committee (IACUC) and National Institutes of Health. Young adult (300g) male Sprague-Dawley rats were injected i.p. with a single dose of 65 mg/kg STZ (Sigma) in 50 mM citrate buffer (pH 4.0). Control animals received an equal amount of citrate buffer injection. Animals were kept in a 12-hour light/dark cycle with free access to water and standard rodent chow. Weight and blood glucose levels of the animals were measured immediately prior to STZ injection and 2 days, 1 week, and 1 and 3 months after injection. Animals with blood glucose levels >250 mg/dL were deemed diabetic. Rats became hyperglycemic 2 days after administration of STZ. Blood glucose levels stayed constantly elevated thereafter and reached 500 (±45) mg/dL. Although diabetic rats lost weight, most of them survived for 3 months (when sacrificed) after STZ-induced diabetes without severe morbid conditions. Rats in GC group are implanted with continuous-release insulin implant (LinShin, Ont, Canada) to keep their blood glucose level below 150 mg/dl. GHb are tested every 2-3 months using Glyco-Tex affinity column method (Helena Lab).

Evans blue assays: Briefly, Evans blue dye (45 mg/ml dissolved in saline) is injected (45 mg/kg) through the jugular vein of the rats. 2 hours after the injection, the rats are perfused with 0.05 M citrate buffer, pH 3.5 (37° C.) to clear the dye from vascular system, and Evans blue is extracted from the retina and measured by SpectraMax M5 microplate reader (Mol. Devices). Relative quantity of Evans blue leaked to and retained in the retina is calculated.

In Vivo knockdown of let-7 by tail-vein injection of LNA-anti-let-7 in rats: LNA-anti-let-7 or negative control anti-miR with 3'-labeled fluorescein (5 mg/kg, Exiqon) is injected through tail vein one week after the onset of STZ-induced diabetes, and every month thereafter for up to 6 and 12 months. Negative control anti-miR has scrambled sequences known not to target any miRNAs.

Intraocular injection of lentivirus expressing let-7: Lentivirus co-expressing let-7d and green fluorescent protein (GFP) (lenti-pmiRHlet7dPA-1) and negative-control lentivirus expressing GFP only (>$10^6$ IFU) are purchased from System Biosciences Inc (SBI. http://www.systembio.com). 1 μl of viral suspension is injected intravitreal one week after the onset of STZ-induced diabetes.

Isolation of retinal endothelial cells. Platelet-endothelial cell-adhesion molecule-1 (PECAM-1), an EC-surface antigen that has been successfully used for the isolation of RECs, was employed as the EC marker to isolate RECs from rat retinas. After anesthetized with 100 mg/kg pentobarbital (i.p.), the rats were perfused with PBS to remove residual blood from the retinas, and the neuroretina from rat eyes was carefully dissected. The retinas was dissociated to single-cell suspension using a Papain Dissociation Kit (Worthington) according manufacturer's protocol and incubated the dissociated cells with FITC-conjugated anti-PECAM-1 antibody (20 μg/ml, Abcam) for 45 min at 4° C., followed by washing with PBS, and incubation with anti-FITC secondary antibody-conjugated microbeads (10 μl for $10^7$ cells, Miltenyi Biotech) for 15 min at 4° C. Then labeled-cells were loaded onto magnetic activated cell sorting (MACS) columns and sorted as PECAM-1 positive and negative portions, according to the manufacturer's protocols (Miltenyi Biotech). The enrichment of ECs was confirmed by flow cytometry and further purified using Fluorescence-Activated Cell Sorting (FACS) (MoFlo high-speed cell sorter, Becton Dickinson).

RNA preparation. Two retinas from each animal and RECs from 5-7 rats were pooled for RNA preparation. Total RNA of the retina and RECs were isolated using the mirVana RNA isolation kit (Ambion) as described previously.

miRNA microarray assays and data analyses. Rodent TaqMan miRNA Microarray, v2.0 (Applied Biosystems), which provides full coverage of all known mouse and rat miRNAs of Sanger miRBase v10 (http://www.mirbase.org), were used for miRNA-expression profiling, according to manufacturer's protocol with minor modifications. Briefly, ~75 ng of total RNA was used for reverse-transcription (RT) reaction. Following reverse-transcription, a 12-cycle pre-amplification was performed, before real-time PCR reactions, using a 7900HT Fast Real-Time PCR System (Applied Biosystems). Three independent sets of miRNA profiling were performed for each experimental condition Amplification data were created by the SDS2.3 program (Applied Biosystems) and further analyzed using RQ Manager software (Applied Biosystems) and StatMiner v. 3.0 (Integromics). The relative expression level for each miRNA is represented as Cycle threshold (Ct). There were three replicate assays for each miRNA on the array. miRNAs with Ct<40 in at least two out of the three replicates were accepted as "detected". Mammalian small nuclear RNA U6 (snRNA U6) was identified as the most stably expressed endogenous control using the GeNorm method (Vandesompele et al., 2002) in the StatMiner software and was used for normalization. Normalized expression level of each miRNA was calculated as DCt or ΔCt=Ct(miRNA)-Ct(snRNA U6). The average DCt from three microarray assays was calculated as the relative expression level of each miRNA. The differential expression of each miRNA from samples of diabetic rats and normal controls was calculated as: DDCt or Δ(ΔCt)=Ave DCt (diabetic)—Ave DCt (control). Fold of change was calculated as $2^{-\Delta(\Delta Ct)}$. The parametric linear model for microarray analysis (LIMMA) was used to compare gene expression profiles between the two groups. The Benjamini-Hochberg method was applied to calculate adjusted p-value to minimize False Discovery Rate (FDR). Adjusted p<0.01 was set as the criteria for significance of differential expression. Correlation heat-map and hierarchical cluster analysis showed that miRNA expression profiles of each tissue type were consistently clustered within the experimental groups (normal control or STZ-induced diabetic tissues).

Quantitative (q)RT-PCR. qRT-PCR analysis of miRNAs was performed using TaqMan microRNA Assays according to the manufacturer's protocol (Applied Biosystems). Approximately 8 ng of total RNA was used for each reaction. snRNA U6 was used for normalization control. qRT-PCR analysis on mRNAs of IRAK1, TRAF6, ICAM-1, and MCP-1 was performed using the QuantiTect Primer Assay with QuantiFast SYBR Green RT-PCR Kit (Qiagen, Valencia, Calif.) ~10 ng total RNA was used in each reaction. 18S rRNA was amplified as normalization control. All data are expressed as mean±SEM. Student's t-test was used to determine significance (p<0.05).

Rat REC culture and treatment with proinflammatory factors. Rat RECs—the Transgenic-inner Blood-Retinal Barrier (Tr-iBRB) cells were kindly provided by Drs. Tetsuya Terasaki, Tohoku University, and Ken-ichi Hosoya, University of Toyama, Japan. The Tr-iBRB cells were derived from RECs of transgenic rats harboring the temperature-sensitive SV40 large T-antigen (tsA58Tg rats). At 33° C., they are immortalized and proliferate because of the expression of large T-antigen. At 37° C., they stop proliferation due to loss of large T-antigen and differentiate into authentic retinal ECs, which have spindle fiber shapes, with typical endothelial and REC-specific markers and endothelial properties and REC-specific functions. iTr-iBRB cells were expanded at 33° C. on collagen-coated (50 µg/ml) plates in complete EC culture medium (DMEM with 70 mg/L benzylpenicillin potassium, 100 mg/L streptomycin sulfate, 10% heat-inactivated FBS and endothelial-cell growth factor (ECGF) (1:100, Sigma). Glucose concentration in the medium was 5.5 mM. Approximately 100,000 cells/60 mm plate were grown in complete medium at 37° C. for 48 hours. Cells were serum starved in DMEM+0.2% FBS for 16 hours before treatment of IL-1β (10 ng/ml, Sigma), TNFα (10 ng/ml, Sigma), or NF-κB inhibitor, Bay11-7082 (3 µM. Calbiochem) for 4 or 24 hours. Subsequently, the cells were harvested for total RNA, protein lysate preparation, or immunofluorescence.

Total RNA preparation and qRT-PCR analysis is performed.

Antibodies and semi-quantitative western blot: Antibodies against p65, p-p65, IKK, p-IKK (Santa Cruz), Lin28 (AbCam), Ras (pan-ras antibody. Santa Cruz), ICAM-1, VCAM-1, Cox-2, iNOS, MCP-1 (AbCam), β-actin (Sigma) are purchased for Western blot analysis, with modification that the result of Enhanced Chemiluminescence (ECL) reaction are scanned using Kodak Image Station 440 (Kodak). β-actin are used as normalization or loading controls. Glyceraldehyde-3-phosphate dehydrogenase (GAPDH) was not used as normalization control, as levels of expression and activity of GAPDH are decreased in diabetic retina and endothelial cells.

Transendothelial electrical resistance assay: ECs are grown as a monolayer on small gold electrodes. The transendothelial electrical resistance, which reflects endothelial barrier function and permeability, is measured using the Electric Cell-Substrate Impedance Sensor (ECIS) system.

Transfection of let-7 mimics and siRNA against Lin28: 50-100 nM of let-7b mimics (Ambion) are transfected into RECs in 5 mM glucose using Oligofectamine (Invitrogen). miRNA negative control (AM17110, Ambion) are transfected in parallel as negative controls. 80 nM siRNA against Lin28 (s191872 or s191873 or s222685. Ambion) or siRNA against H-ras (s234922 or s234921 or s147725. Ambion) are transfected into RECs culture in 5 mM glucose using siPORT NeoFX transfection agent (Ambion). siRNA negative control (AM4611, Ambion) are transfected in parallel for negative controls. siRNAs against Lin28 and H-ras will be picked among the three pre-designed siRNAs from Ambion. The efficiency of the siRNAs is tested by immunostaining on Lin28 and H-ras 48 hours after transfection with the siRNAs. The ones with the highest inhibition on the expression of Lin28 and H-ras, respectively, are used for knockdown experiments.

Statistic analysis: All experiments are preferably performed with at least three duplicates. The significance of difference is evaluated by non-parametric ANOVA tests.

let-7-involved positive feedback loops are activated in RECs of diabetic rats maintained under poor glycemic control; and remain activated in RECs of diabetic rats maintained Under good glycemic control after initial poor glucose control.

STZ-induced diabetic rat model is used to study the following four groups of rats with at least 6 rats in each group. Group I (GC): STZ-induced diabetic rats with good glycemic control (GC. Blood glucose<150 mg/dl, and glycated hemoglobin (GHb)<7%) soon after (<2 weeks) the onset of diabetes, for 12 months; Group II (PC): age- and sex-matched STZ-induced diabetic rats with poor glycemic control (PC. GHb>11%) for 12 months; Group III (PC-GC): age- and sex-matched STZ-induced diabetic rats with 6-month PC, followed by 6-month GC; Group IV (normal control): age- and sex-matched normal control rats without STZ-injection. At the end of the "incubation" time, RECs are isolated from the retina using MACS with anti-PE-CAM-1 antibody, and prepare total RNA and protein lysate of RECs, followed by comprehensive assays: First, NF-κB activation status is examined in RECs; secondly, will examine the status of Lin28, IL-6 and H-ras, K-ras and N-ras by qRT-PCR and semi-quantitative Western blot, and let-7 expression levels are examined by Taqman miRNA qRT-PCR assays on let-7a/b/c/d/e/f/g/I.

Compared to Group I (GC) and normal control rats (Group IV), in RECs of Group II (PC) rats, NF-κB may be activated, Lin28 is upregulated at both mRNA and protein levels, decreased levels of mature let-7, and increased expression of Ras and IL-6, suggesting that the let-7-involved NF-κB activation positive feedback loops may be activated in RECs in diabetic rats.

In RECs of Group III (PC-GC) rats, NF-κB may remain activated compared to GC rats (Group I) and normal control rats (Group IV), suggesting metabolic memory of NF-κB activation in RECs after uncontrolled diabetes. If the let-7-involved NF-κB-activation feedback loops contribute to metabolic memory in RECs, similar as in Group II (PC) rats, Lin28 may be upregulated, while let-7 may be decreased; and Ras and IL-6 may be upregulated. let-7-involved NF-κB-activation positive feedback loops may be activated in RECs of DR rats in vivo, and represent a new molecular mechanism underlying the sustained NF-κB activation and inflammatory responses in the pathogenesis of DR and metabolic memory in RECs in vivo.

Interruption of the let-7-involved positive feedback loops may "erase" or attenuate metabolic memory in RECs of diabetic rats with good glycemic control after initial poor glycemic control. As NF-κB and let-7 are two of the key components of the "axis" of the positive feedback loops, targeting these two molecules with at least the following three experiments:

Transfection with miR-146a mimics. Tr-iBRB cells were seeded in collagen-coated plates in complete medium in the absence of antibiotics. After an overnight incubation, the cells were transfected with miR-146a mimic (10 µM) or negative control oligoduplex with scrambled sequences that does not target any mRNAs (Ambion) using Lipofectamine RNAiMAX (1:100) (Invitrogen) for 7 hours. Subsequently, the transfection medium was replaced with fresh complete medium, and the cells were harvested for RNA and protein preparation 48 hours after the transfection.

Antibodies and Western blot analysis. Antibodies against IRAK1, TRAF6, and β-actin were purchased from Chemicon and Santa Cruz Biotech. To prepare protein lysate, cells were homogenized on ice in lysis buffer containing 150 mM NaCl, 25 mM Tris-HCl, 5 mM EDTA, 1% NP-40, and 1× complete protease inhibitor cocktail (Sigma). 10 ug of protein lysate were separated by 7.5% SDS-PAGE gel, followed by electro-transfer to nitrocellulose membrane. Membranes were blocked in 2.5% fat-free milk and incubated with primary antibody at 4° C. overnight. Blots were washed and incubated with HRP-conjugated secondary antibody Immunoreactive bands were visualized using HyGlo western blotting detection reagent (Denville Scientific) and analyzed with a Kodak Imaging System. β-actin was used as normalization control.

Detection of NF-κB activation by immunofluorescence of p65 subunit. 30 min following cytokine treatment, cells were fixed with 4% paraformaldehyde for 20 min. After blocking with 10% normal donkey serum (NDS) in PBS for 1 hour at room temperature, cells were incubated with anti-p65 antibody (Santa Cruz) at 4° C. overnight. Cells were incubated in Alexa fluor-conjugated secondary antibody (1:400) in 3% NDS. Nuclei of the cells were labeled with Hoechst nuclear dye (1:500). Subsequently, the cells were observed under an Axioplan2 fluorescent microscope (Zeiss).

Inhibition of NF-κB activation by NF-κB inhibitors: NF-κB inhibitors (6 μM SN-50, 5 μM Bay-117082 or 5 μm of JSH-23. Calbiochem) are added to one set of RECs in HG, in parallel to another set of RECs in HG without NF-κB inhibitors. If NF-κB activation is the trigger to initiate the positive feedback loops, inhibition of NF-κB during the primary HG culture may prevent activation of the positive feedback loops and prevent formation of metabolic memory. HG-induced NF-κB activation and subsequent upregulation of Lin28, Ras and IL-6, and downregulation of let-7 may not be observed in RECs in HG with NF-κB inhibitors, compared to RECs in HG without NF-κB inhibitors. Functionally, HG-induced increased permeability may be alleviated.

To test the effect of inhibition of NF-κB activation on metabolic memory in RECs, NF-κB inhibitors are added to the secondary NG culture after primary HG culture. If the let-7-involved positive feedback loops are responsible for metabolic memory in RECs, the persistent NF-κB-activation, upregulation of Lin28, Ras and IL-6, as well as other NF-κB downstream genes, and downregulation of let-7 may be lost or attenuated in RECs of HG-to-NG with NF-κB inhibitors, compared to RECs of HG-to-HG.

Inhibition of Lin28 expression by small interfering RNA (siRNA): Lin28 is a key component of the positive feedback loops (FIG. 9). Inhibition of Lin28 by siRNAs during the primary HG culture also may prevent activation of the positive feedback loops and formation of metabolic memory. siRNA is transfected against Lin28 at the start of the primary HG culture. Negative control siRNA is transfected in parallel. After the primary HG culture, Lin28 is downregulated because of the siRNA, and let-7 is upregulated, Ras and IL-6 are downregulated, and NF-κB activation also may be attenuated compared to RECs in HG culture transfected with negative control siRNA. Functionally, HG-induced increased permeability may be alleviated, suggesting that inhibition of Lin28 may have interrupted the positive feedback loops, and that the NF-κB-activation positive feedback loops play important roles in HG-induced sustained inflammatory response and endothelial damage.

To test the effect of inhibition of Lin28 on metabolic memory, siRNA is transfected against Lin28 at the start of the secondary NG culture. After the secondary culture, Lin28 is downregulated because of the siRNA, let-7 may be upregulated, while Ras and IL-6 are downregulated, and NF-κB activation and upregulation of its downstream genes also may be attenuated, when compared to RECs in HG-to-NG transfected with negative control siRNA, suggesting that inhibition of Lin28 may have interrupted the positive feedback loops during the secondary culture, and that the NF-κB-activation positive feedback loops play important roles in metabolic memory in RECs.

Simultaneous depletion of IL-6 and inactivation of Ras by monoclonal antibody against IL-6 and siRNA against H-ras, respectively: IL-6 and Ras both are important components of the positive feedback loops, activating NF-κB. To test this in RECs, siRNA against H-ras are transfected one day before the start of primary HG culture. Negative control siRNA is transfected in parallel. Upon the start of primary culture, monoclonal antibody against IL-6 (Ab-IL-6) or isotype antibody (Ab-IgG, as negative control) (2 μg/ml. R and D Systems) is added to the medium. After the primary culture, H-Ras is decreased in RECs transfected with H-Ras siRNA; IL-6 and Lin28 are downregulated, and NF-κB activation and upregulation of its downstream genes also are lost or attenuated, while let-7 is upregulated compared to RECs in HG with Ab-IgG and negative control siRNA. Functionally, HG-induced increased permeability may be alleviated, suggesting that simultaneous depletion of IL-6 and inactivation of Ras interrupt the positive feedback loops, and that the let-7-involved positive feedback loops play important roles in HG-induced sustained inflammatory response and endothelial damage.

To test the effect on metabolic memory of RECs, siRNA against H-ras are transfected at the start of the secondary NG culture. Negative control siRNA is transfected to RECs in parallel. Ab-IL-6 or Ab-IgG (2 μg/ml) is added to the secondary culture medium. H-ras is downregulated because of the effect of siRNA, let-7 is upregulated, while IL-6 and Lin28 are downregulated, and NF-κB activation and upregulation of its downstream genes are lost or attenuated at the end of the secondary culture. The increased in vitro permeability may be attenuated in RECs of HG-to-NG with H-ras siRNA and Ab-IL-6, when compared to the RECs in HG-to-NG with negative control siRNA and Ab-IgG, suggesting that simultaneous depletion of IL-6 and inactivation of Ras interrupt the positive feedback loops, and that the let-7-involved positive feedback loops play important roles in metabolic memory in RECs.

Cell culture and treatment. Primary Human Retinal Endothelial Cells (HRECs) (Passage 3-6) and HEK293 cells were purchased from Applied Cell Biology Res Institute (Kirkland, Wash.) and American Type Culture Collection (ATCC), respectively. HRECs were maintained in EGM2-MV media with 5% of FBS (Lonza) in flasks coated with attachment factor (Invitrogen) or plates coated with fibronectin (Sigma). For thrombin treatment, HRECs were serum starved in EGM2-MV media with 1% FBS overnight, and then treated with thrombin (5 U/ml) (Sigma. Cat. T4393) for 5-8 hours, followed by RNA harvesting, leukocyte adhesion and other assays; for IL-1β treatment, after overnight serum starvation, HRECs was incubated with 10 ng/ml IL-1β (Sigma) for 4 hours. When NF-κB specific inhibitor Bay11-7082 was used, HRECs was incubated with Bay11-7082 (3 μM) (Sigma) for 30 minutes prior to treatment with either thrombin or IL-1β.

miR-146a mimic, anti-miR-146a and plasmid transfection. Human miR-146a mimic (Applied Biosystems) was used for over-expression of has-miR-146a, with an oligo duplex with scrambled sequences (Applied Biosystems) as negative control. miRCURY LNA-anti-miR-146a (Exiqon) was used for downregulation of miR-miR-146a in HRECs;

and a LNA-miRNA inhibitor negative control oligo (Exiqon) was used as negative control. After overnight serum starvation, HRECs were transfected with miR-146a mimics and/or anti-miR-146a, or negative control oligoes at a final concentration of 10 nM using Lipofectamine RNAimax (Invitrogen) for 48 hours, before harvesting the cells or other downstream assays. When CARD10 and/or TRAF6 were co-transfected with miR-146a mimics in HRECs, 150 ng of plasmid constructs expressing CARD10 (Genecopoeia) and/or TRAF6 (Genecopoeia) under a CMV promoter, or an empty vector (Genecopoeia) as negative control, was co-transfected with miR-146a mimics (12 nM) using Lipofectamine 2000 (Invitrogen) (Xu et al., 2007).

RNA preparation and quantitative RT-PCR. Total RNA was prepared using miRVana miRNA isolation kit (Ambion) (Kovacs et al., 2011). qRT-PCR of miRNAs was performed using TaqMan microRNA Assays (Applied Biosystems), with snRNA U6 as normalization control. qRT-PCR of mRNAs of was performed using QuantiTect Primer Assays and QuantiFast SYBR Green RT-PCR Kit (Qiagen), with 18s rRNA as normalization control. Two tailed t test was used to determine significance of differences.

Target Luciferase Reporter assays. Luciferase reporter constructs with wild-type or mutant target sites of miR-146 (Genecopoeia. HmiT008522-MT01, HmiT008522-MT01-01 and HmiT008522-MT01-02) (FIG. 26) (160 nM) were co-transfected with miR-146a mimics or negative control oligo duplex with scrambled sequences (12 nM. Applied Biosystems) into HRECs or HEK cells using Lipofectamine 2000 (Invitrogen). 48 hours after transfection, the cells were harvested and luciferase assays were performed using the Luc-Pair miR Luciferase Assay system (Genecopoeia) and a Glomax plate reader (Promega). Relative luciferase activity was calculated as firefly luciferase activity normalized by Renilla luciferase activity. Two tailed t test was used to determine the statistical significance of differences.

Antibodies, Protein harvesting, and Western blot. HRECs were harvested and sonicated in RIPA buffer with protease inhibitors (0.5 mM AEBSF, 0.4 µM Aprotinin, 10 µM Leupeptin, 20 µM Bestatin, 7.5 µM Pepstatin A and 7.0 µM E-64. Sigma). Western blot was performed using antibodies to human CARD10 (Abcam, Cat. Ab64171) and β-actin (Santa Cruz. Cat. sc-47778).

Leukocyte adhesion to HRECs. Leukocyte adhesion assays were performed (Huang et al., 2007; O'Donnell, 2011) with minor modifications. Briefly, blood from healthy human volunteers was collected according to a approved IRB protocol to isolate leukocytes. Leukocytes were labeled with 5 µM Calcein/acetomethoxy (AM) (Invitrogen). HRECs were transfected with miR-146a mimics or negative control oligo duplex with scrambled sequences for 48 hours before thrombin treatment (5 U/ml). Eight hours after thrombin treatment, $10^5$ calcein-labeled leukocytes were added onto the HREC monolayer and incubated for 2 hours at 37 C. Subsequently, the cells were gently rinsed with PBS to wash off leukocytes unattached to HRECs; the number of Calcein-AM labeled neutrophils attached to HRECs were counted by fluorescence microscopy. In addition, the fluorescence from the adherent leukocytes on HRECs was measured with a Cytofluor plate reader (PreSeptive Biosystems).

Transendothelial electrical resistance (TEER) assay. HRECs were plated and grew as a monolayer on fibronectin-coated Electric Cell-Substrate Impedance Sensor (ECIS) electrode arrays (Applied Biophysics). 24 hours after transfection with miR-146a mimics, or negative control oligo duplex with scrambled sequences, the cells were treated with IL-1β (10 ng/ml). TEER was recorded for 20 hours before and 24 hours after addition of IL-1β using the ECIS system (Applied Biophysics) (Qiao et al., 2003, 2006; Lum et al., 2003, 2001). When Bay11-7082 was used, HRECs was incubated with Bay11-7082 (100 µM) (Sigma) for 30 minutes prior to IL-1β treatment.

TABLE 1

Numbers of miRNAs detected and changed significantly in their expression levels in the retina and retinal endothelial cells (RECs) in STZ-induced diabetic and normal control rats.

|  | Retina | RECs |
| --- | --- | --- |
| Control | 354 (63.6%) | 221 (39.7%) |
| Diabetic | 355 (63.7%) | 216 (38.8%) |
| Significantly changed | 87 (24.6%) | 120 (54.3%) |
| Upregulated in diabetic rats | 81 | 16 |
| Downregulated in diabetic rats | 6 | 104 |

TABLE 2

Expression profiles of the top 20 highest-expressed miRNAs in retinas of normal control rats and STZ-induced diabetic rats.

| | Control rats | | | Diabetic rats | |
| --- | --- | --- | --- | --- | --- |
| No. | miRNAs | Ave DCt* | No. | miRNAs | Ave DCt* |
| 1 | mmu-miR-30c | 2.5 | 1 | mmu-miR-30c | 2.3 |
| 2 | mmu-miR-204 | 3.2 | 2 | mmu-miR-204 | 2.6 |
| 3 | mmu-miR-30b | 3.2 | 3 | mmu-miR-30b | 3.0 |
| 4 | mmu-miR-211 | 3.4 | 4 | mmu-miR-9 | 3.0 |
| 5 | mmu-miR-9 | 3.4 | 5 | mmu-miR-211 | 3.5 |
| 6 | mmu-miR-182 | 3.8 | 6 | mmu-miR-181a | 3.6 |
| 7 | mmu-miR-181a | 4.2 | 7 | mmu-miR-182 | 3.9 |
| 8 | mmu-miR-26a | 4.3 | 8 | mmu-miR-26a | 4.0 |
| 9 | mmu-miR-690 | 4.7 | 9 | mmu-miR-191 | 4.5 |
| 10 | mmu-miR-191 | 4.8 | 10 | mmu-miR-29a | 4.6 |
| 11 | mmu-miR-19b | 5.0 | 11 | mmu-miR-19b | 5.1 |
| 12 | mmu-miR-29a | 5.0 | 12 | mmu-miR-690 | 5.4 |
| 13 | mmu-miR-29c | 5.9 | 13 | mmu-miR-29c | 5.7 |
| 14 | mmu-miR-16 | 6.0 | 14 | mmu-miR-16 | 5.8 |
| 15 | mmu-miR-30e | 6.1 | 15 | mmu-miR-24 | 5.8 |
| 16 | mmu-miR-138 | 6.2 | 16 | mmu-miR-30e | 5.9 |
| 17 | mmu-miR-26b | 6.2 | 17 | mmu-miR-183 | 6.0 |
| 18 | mmu-miR-384-5p | 6.3 | 18 | mmu-miR-30a | 6.1 |
| 19 | mmu-miR-124 | 6.4 | 19 | mmu-miR-184 | 6.1 |
| 20 | mmu-miR-24 | 6.4 | 20 | mmu-miR-709 | 6.1 |

*Ave DCt: average DCt. snRNA U6 was used as normalization control. DCt = $Ct_{miRNA}$ - $Ct_{snRNAU6}$.

TABLE 3

Expression profiles of the top 20 miRNAs expressed in retinal endothelial cells of normal control and STZ-induced diabetic rats.

| | Control rats | | | Diabetic rats | |
| --- | --- | --- | --- | --- | --- |
| No. | miRNAs | Ave DCt* | No. | miRNAs | Ave DCt* |
| 1 | mmu-miR-204 | 0.6 | 1 | mmu-miR-466d-3p | 1.6 |
| 2 | mmu-miR-466d-3p | 0.8 | 2 | mmu-miR-126-3p | 1.7 |
| 3 | mmu-miR-126-3p | 1.2 | 3 | mmu-miR-709 | 1.8 |
| 4 | mmu-miR-9 | 1.2 | 4 | mmu-miR-145 | 2.1 |
| 5 | mmu-miR-709 | 1.4 | 5 | mmu-miR-9 | 2.3 |
| 6 | mmu-miR-690 | 2.6 | 6 | mmu-miR-204 | 2.6 |
| 7 | mmu-miR-150 | 2.7 | 7 | mmu-miR-150 | 2.9 |
| 8 | mmu-miR-145 | 3.0 | 8 | mmu-miR-30c | 3.6 |

TABLE 3-continued

Expression profiles of the top 20 miRNAs expressed in retinal endothelial cells of normal control and STZ-induced diabetic rats.

| Control rats | | | Diabetic rats | | |
|---|---|---|---|---|---|
| No. | miRNAs | Ave DCt* | No. | miRNAs | Ave DCt* |
| 9 | mmu-miR-211 | 3.2 | 9 | mmu-miR-19b | 3.6 |
| 10 | mmu-miR-30c | 3.4 | 10 | mmu-miR-29a | 4.3 |
| 11 | mmu-miR-9* | 4.0 | 11 | mmu-miR-690 | 4.4 |
| 12 | mmu-miR-26a | 4.1 | 12 | mmu-miR-24 | 4.5 |
| 13 | mmu-miR-29a | 4.2 | 13 | mmu-miR-30b | 4.9 |
| 14 | mmu-miR-126-5p | 4.2 | 14 | mmu-miR-720 | 4.9 |
| 15 | mmu-miR-720 | 4.2 | 15 | mmu-miR-211 | 5.2 |
| 16 | mmu-miR-24 | 4.3 | 16 | mmu-miR-146a | 5.2 |
| 17 | mmu-miR-30b | 4.7 | 17 | mmu-miR-143 | 5.3 |
| 18 | mmu-miR-467a* | 4.7 | 18 | mmu-miR-191 | 5.4 |
| 19 | mmu-miR-19b | 4.9 | 19 | mmu-miR-30a | 5.6 |
| 20 | mmu-miR-191 | 4.9 | 20 | mmu-miR-106a | 5.7 |

*Ave DCt: average DCt. snRNA U6 was used as normalization control. DCt = $Ct_{miRNA} - Ct_{snRNAU6}$.

TABLE 4

Differentially expressed miRNAs in the retina of STZ-induced diabetic rats compared to normal control rats, and confirmed by qRT-PCR.

| miRNAs | Fold of change (STZ/ctl) (array) | p value (array) | Fold of change (STZ/Ctl) (qRT-PCR) | p value (qRT-PCR) | Chromosomal Localization[b] (rat) | Chromosomal Localization (human) | SEQ ID NOS 1-19, respectively, in order of appearance |
|---|---|---|---|---|---|---|---|
| mmu-miR-223 | 6.1 | 7.1E-05 | 4.5 | 1.5E-05 | Xq31 | Xq12 | UGUCAGUUUGUCAAAUACCCCA |
| mmu-miR-184 | 3.1 | 2.8E-04 | 2.9 | 1.3E-03 | 8q31 | 15q24.3 | UGGACGGAGAACUGAUAAGGGU |
| mmu-miR-378* | 2.8 | 3.1E-03 | 2.8 | 7.7E-04 | 18q12.1 | 5q32 | CUCCUGACUCCAGGUCCUGUGU |
| mmu-miR-31* | 2.7 | 3.1E-03 | 2.6 | 2.6E-05 | 5q32 | 9p21.3 | UGCUAUGCCAACAUAUUGCCAUC |
| mmu-miR-335-3p | 2.2 | 2.1E-03 | 2.5 | 1.4E-04 | NA[c] | 7q32.2 | UUUUUCAUUAUUGCUCCUGACC |
| mmu-miR-31 | 2.4 | 9.0E-04 | 2.5 | 2.5E-03 | 5q32 | 9p21.3 | AGGCAAGAUGCUGGCAUAGCUG |
| mmu-miR-378 | 1.6 | 3.1E-03 | 2.4 | 5.8E-06 | 18q12.1 | 5q32 | ACUGGACUUGGAGUCAGAAGG |
| mmu-miR-574-3p | 3.2 | 2.2E-03 | 2.4 | 7.2E-05 | NA** | 4p14 | CACGCUCAUGCACACACCCACA |
| mmu-miR-205 | 2.5 | 3.5E-03 | 2.3 | 3.1E-05 | 13q27 | 1q32.2 | UCCUUCAUUCCACCGGAGUCUG |
| mmu-miR-199a-3p | 2.9 | 3.5E-03 | 1.9 | 9.9E-04 | 13q22 | 19p13.2 & 1q24.2 | ACAGUAGUCUGCACAUUGGUUA |
| mmu-miR-34b-3p | 2.2 | 6.0E-03 | 1.9 | 6.2E-04 | 8q24 | 11q23.1 | AAUCACUAACUCCACUGCCAUC |
| mmu-miR-200b | 2.6 | 1.9E-03 | 1.8 | 1.1E-02 | 5q36 | 1p36.33 | UAAUACUGCCUGGUAAUGAUGA |
| mmu-miR-335-5p | 1.8 | 2.3E-02 | 1.7 | 1.1E-04 | NA | 7q32.2 | UCAAGAGCAAUAACGAAAAAUGU |
| mmu-miR-34c | 2.2 | 2.5E-03 | 1.5 | 1.1E-02 | 8q24 | 11q23.1 | AGGCAGUGUAGUUAGCUGAUUGC |
| mmu-miR-200a | 2.3 | 3.8E-03 | 1.4 | 5.3E-03 | 5q36 | 1p36.33 | UAACACUGUCUGGUAACGAUGU |
| mmu-miR-488 | 2.3 | 3.5E-03 | 1.3 | 2.5E-02 | 13q22 | 1q25.1 | UUGAAAGGCUGUUUCUUGGUC |
| rno-miR-20b-5p | -1.4[a] | 3.4E-03 | -1.5 | 8.5E-05 | Xq36 | Xq26.2 | CAAAGUGCUCAUAGUGCAGGUAG |
| mmu-miR-499 | -1.9[a] | 3.5E-D3 | -1.3 | 1.0E-03 | 3q42 | 20q11.22 | UUAAGACUUGCAGUGAUGUUU |
| mmu-miR-690 | -1.6[a] | 3.1E-03 | -1.2 | 3.6E-03 | NA | NA | AAAGGCUAGGCUCACAACCAAA |

[a]Negative numbers denote the folds of decrease in STZ-induced diabetic rats compared to normal controls;
[b]Chromosomal localization was compiled using Ensembl genome browser (uswest.ensembl.org);
[c]NA: chromosomal localization is not available according to Ensembl genome browser (uswest.ensembl.org).

TABLE 5

Differentially expressed miRNAs in RECs of STZ-induced diabetic rats, compared to the ones of normal control rats, and confirmed by qRT-PCR.

| miRNAs | Fold of change (STZ/Ctl) (array) | p value (array) | Fold of change (STZ/Ctl) (qRT-PCR) | p value (qRT-PCR) | Chromosomal localization[b] (rat) | Chromosomal localization[b] (human) | SEQ ID NOS 20-36, respectively, in order of appearance |
|---|---|---|---|---|---|---|---|
| mmu-miR-15b | 4.0 | 5.8E-07 | 1.4 | 4.2E-02 | 2q31 | 3q26.1 | UAGCAGCACAUCAUGGUUUACA |
| mmu-miR-19b | 2.4 | 1.4E-05 | 1.5 | 3.8E-03 | 15q24 & Xq36 | 13q31.3 & Xq26.2 | UGUGCAAAUCCAUGCAAAACUGA |
| mmu-miR-21 | 3.7 | 2.3E-06 | 1.5 | 4.2E-04 | 10q26 | 17q22 | UAGCUUAUCAGACUGAUGUUGA |
| mmu-miR-31 | 1.7 | 8.2E-04 | 1.9 | 4.9E-04 | 5q32 | 9p21.3 | AGGCAAGAUGCUGGCAUAGCUG |
| mmu-miR-132 | 2.0 | 4.2E-05 | 1.4 | 1.6E-04 | 10q24 | 17p13.3 | UAACAGUCUACAGCCAUGGUCG |
| mmu-miR-142-3p | 1.8 | 2.5E-04 | 2.5 | 2.2E-07 | 10q26 | 17q22 | UGUAGUGUUUCCUACUUUAUGGA |
| mmu-miR-146a | 2.8 | 5.5E-05 | 2.1 | 5.8E-04 | 10q21 | 5q34 | UGAGAACUGAAUUCCAUGGGUU |
| mmu-miR-155 | 1.8 | 2.0E-03 | 1.7 | 3.6E-03 | NA[c] | 21q21.2 | UUAAUGCUAAUUGUGAUAGGGGU |
| mmu-miR-339-5p | 2.9 | 2.1E-03 | 1.9 | 2.0E-03 | 12q11 | 7p22.3 | UCCCUGUCCUCCAGGAGCUCACG |
| mmu-miR-342-3p | 2.6 | 1.1E-03 | 1.5 | 7.5E-03 | 6q32 | 14q32.2 | UCUCACACAGAAAUCGCACCCGU |
| rno-miR-450a | 1.9 | 5.0E-04 | 1.4 | 1.4E-03 | Xq36 | Xq26.2 | UUUUGCGAUGUGUUCCUAAUGU |
| mmu-miR-29c | -7.2[a] | 5.8E-07 | -1.7[a] | 9.8E-03 | 13q27 | 1q32.1 | UAGCACCAUUUGAAAUCGGUUA |
| mmu-miR-92a | -1.7 | 5.5E-04 | -1.4 | 8.0E-03 | 15q24 & Xq36 | 13q31.3 & Xq26.2 | UAUUGCACUUGUCCCGGCCUG |
| mmu-miR-181c | -9.3 | 3.4E-04 | -1.4 | 1.6E-02 | 19q11 | 19p13.2 | AACAUUCAACCUGUCGGUGAGU |
| mmu-miR-376c | -46.6 | 5.8E-07 | -2.0 | 1.3E-02 | 6q32 | 14q32.2 | AACAUAGAGGAAAUUUCACGU |
| rno-miR-136* | -19.6 | 3.6E-05 | -2.0 | 2.6E-02 | 6q32 | 14q32.2 | CAUCAUCGUCUCAAAUGAGUCU |
| rno-miR-20b-5p | -6.6 | 3.4E-07 | -2.1 | 3.7E-06 | Xq36 | Xq26.2 | CAAAGUGCUCAUAGUGCAGGUAG |

[a]Negative numbers mark the folds of decrease in STZ-induced diabetic rats, compared to normal controls;
[b]Chromosomal localization was compiled using the Ensembl genome browser (uswest.ensembl.org);
[c]NA: chromosomal localization is not available according to the Ensembl genome browser (uswest.ensembl.org).

TABLE 6

Normal rat's VITREOUS TRANSCRIPTOME

| | miRNA | AVE DCt (ctr) |
|---|---|---|
| 1 | mmu-miR-720 | -1.15 |
| 2 | mmu-miR-709 | -0.07 |
| 3 | mmu-miR-204 | 0.02 |
| 4 | mmu-miR-466d-3p | 0.50 |
| 5 | mmu-miR-184 | 0.90 |
| 6 | mmu-miR-106a | 1.77 |
| 7 | mmu-miR-17 | 2.00 |
| 8 | mmu-miR-211 | 2.56 |
| 9 | mmu-miR-690 | 2.84 |
| 10 | mmu-miR-30b | 3.82 |
| 11 | mmu-miR-30c | 3.85 |
| 12 | mmu-miR-191 | 3.87 |
| 13 | mmu-miR-24 | 3.95 |
| 14 | mmu-miR-467a* | 4.06 |
| 15 | rno-miR-664 | 4.55 |
| 16 | mmu-miR-678 | 4.78 |
| 17 | mmu-miR-141* | 4.78 |
| 18 | mmu-miR-26a | 4.83 |
| 19 | mmu-miR-146a | 4.84 |
| 20 | mmu-miR-149 | 4.85 |
| 21 | mmu-let-7c | 4.98 |
| 22 | rno-miR-204* | 4.98 |
| 23 | mmu-let-7b | 4.99 |
| 24 | mmu-miR-19b | 5.05 |
| 25 | mmu-miR-16 | 5.06 |
| 26 | mmu-miR-9 | 5.10 |
| 27 | mmu-miR-764-5p | 5.12 |
| 28 | mmu-miR-30e* | 5.14 |
| 29 | mmu-miR-9* | 5.19 |
| 30 | mmu-miR-30a* | 5.30 |
| 31 | mmu-miR-125b-5p | 5.30 |
| 32 | mmu-miR-29b* | 5.46 |
| 33 | mmu-miR-699 | 5.49 |
| 34 | mmu-miR-31 | 5.53 |
| 35 | mmu-miR-328 | 5.63 |
| 36 | mmu-let-7e-4395517 | 5.73 |
| 37 | mmu-miR-31*-4395625 | 5.74 |
| 38 | mmu-miR-342-3p-4395371 | 6.02 |
| 39 | mmu-miR-145-4395389 | 6.04 |
| 40 | mmu-miR-99a-4373008 | 6.12 |
| 41 | mmu-miR-99b-4373007 | 6.28 |
| 42 | mmu-miR-139-5p-4395400 | 6.29 |
| 43 | mmu-miR-183*-4395381 | 6.30 |
| 44 | mmu-miR-760-4395439 | 6.30 |

TABLE 6-continued

Normal rat's VITREOUS TRANSCRIPTOME

| | miRNA | AVE DCt (ctr) |
|---|---|---|
| 45 | mmu-miR-384-5p-4395732 | 6.31 |
| 46 | mmu-miR-182-4395729 | 6.48 |
| 47 | mmu-miR-126-3p-4395339 | 6.57 |
| 48 | mmu-miR-20b-4373263 | 6.65 |
| 49 | mmu-miR-20a-4373286 | 6.67 |
| 50 | mmu-miR-223-4395406 | 6.75 |
| 51 | mmu-miR-100-4373160 | 6.75 |
| 52 | mmu-miR-92a-4373013 | 6.77 |
| 53 | mmu-miR-138-4395395 | 6.81 |
| 54 | mmu-let-7d-4395394 | 6.83 |
| 55 | mmu-miR-26b-4395167 | 6.91 |
| 56 | mmu-miR-133a-4395357 | 6.91 |
| 57 | mmu-miR-150-4373127 | 6.92 |
| 58 | mmu-miR-181a-4373117 | 6.92 |
| 59 | mmu-miR-7a*-4381118 | 7.06 |
| 60 | mmu-miR-218-4373081 | 7.07 |
| 61 | mmu-miR-485*-4386764 | 7.09 |
| 62 | rno-miR-20b-5p-4381106 | 7.10 |
| 63 | mmu-miR-135a*-4395343 | 7.12 |
| 64 | mmu-miR-29a-4395223 | 7.22 |
| 65 | mmu-miR-320-4395388 | 7.23 |
| 66 | mmu-miR-222-4395387 | 7.31 |
| 67 | mmu-miR-434-3p-4395734 | 7.32 |
| 68 | mmu-miR-183-4395380 | 7.38 |
| 69 | mmu-miR-30a-4373061 | 7.45 |
| 70 | mmu-miR-132-4373143 | 7.60 |
| 71 | mmu-miR-30e-4395334 | 7.63 |
| 72 | mmu-miR-203-4373095 | 7.69 |
| 73 | mmu-let-7i-4395332 | 7.70 |
| 74 | mmu-miR-125a-5p-4395309 | 7.76 |
| 75 | mmu-miR-127-4373147 | 7.79 |
| 76 | mmu-miR-193b-4395597 | 7.92 |
| 77 | rno-miR-489-4381127 | 8.00 |
| 78 | mmu-miR-574-3p-4395460 | 8.02 |
| 79 | rno-miR-463-4395751 | 8.02 |
| 80 | mmu-miR-129-3p-4373297 | 8.13 |
| 81 | mmu-miR-375-4373027 | 8.18 |
| 82 | mmu-miR-467b*-4381092 | 8.18 |
| 83 | mmu-let-7g-4395393 | 8.28 |
| 84 | mmu-miR-23b-4373073 | 8.34 |
| 85 | rno-miR-1-4395765 | 8.34 |
| 86 | mmu-miR-331-3p-4373046 | 8.35 |
| 87 | mmu-miR-200c-4395411 | 8.35 |
| 88 | mmu-miR-29a*-4395558 | 8.41 |
| 89 | mmu-miR-181a-1*-4373086 | 8.50 |
| 90 | mmu-miR-134-4373299 | 8.51 |
| 91 | mmu-miR-206-4373092 | 8.54 |
| 92 | mmu-miR-484-4381032 | 8.58 |
| 93 | mmu-miR-99b*-4395307 | 8.66 |
| 94 | mmu-miR-186-4395396 | 8.66 |
| 95 | mmu-miR-93-4373302 | 8.69 |
| 96 | mmu-miR-140-4373374 | 8.69 |
| 97 | mmu-miR-135a-4373140 | 8.71 |
| 98 | mmu-let-7a*-4395608 | 8.74 |
| 99 | mmu-miR-22-4373079 | 8.82 |
| 100 | mmu-miR-706-4381061 | 8.86 |
| 101 | mmu-miR-195-4373105 | 8.88 |
| 102 | mmu-miR-146b-4373178 | 8.94 |
| 103 | mmu-miR-378-4395354 | 8.96 |
| 104 | mmu-miR-365-4373194 | 9.01 |
| 105 | mmu-miR-30d-4373059 | 9.02 |
| 106 | mmu-miR-877-4395402 | 9.02 |
| 107 | mmu-miR-34c*-4395714 | 9.06 |
| 108 | mmu-miR-532-3p-4395466 | 9.12 |
| 109 | mmu-miR-205-4373093 | 9.12 |
| 110 | mmu-miR-152-4395170 | 9.12 |
| 111 | mmu-miR-135b-4395372 | 9.18 |
| 112 | mmu-miR-301a-4373064 | 9.18 |
| 113 | mmu-miR-130a-4373145 | 9.20 |
| 114 | mmu-miR-124-4373295 | 9.20 |
| 115 | mmu-miR-101b-4395661 | 9.21 |
| 116 | mmu-miR-667-4386769 | 9.28 |
| 117 | mmu-miR-673-5p-4386772 | 9.29 |
| 118 | mmu-miR-1-4395333 | 9.35 |
| 119 | mmu-miR-335-5p-4373045 | 9.45 |
| 120 | mmu-miR-103-4373158 | 9.46 |
| 121 | mmu-miR-93*-4395250 | 9.46 |
| 122 | mmu-miR-210-4373089 | 9.47 |
| 123 | mmu-miR-151-3p-4373304 | 9.49 |
| 124 | mmu-miR-495-4381078 | 9.57 |
| 125 | mmu-miR-872*-4395672 | 9.63 |
| 126 | mmu-miR-379-4373349 | 9.63 |
| 127 | mmu-miR-106b-4373155 | 9.67 |
| 128 | mmu-miR-19a-4373099 | 9.67 |
| 129 | mmu-miR-301b-4395730 | 9.71 |
| 130 | mmu-miR-125b*-4395638 | 9.74 |
| 131 | mmu-miR-335-3p-4395296 | 9.81 |
| 132 | mmu-miR-878-3p-4395671 | 9.86 |
| 133 | mmu-miR-27a*-4395556 | 9.87 |
| 134 | rno-miR-125b*-4395775 | 9.87 |
| 135 | mmu-miR-592-4395560 | 9.90 |
| 136 | mmu-miR-126-5p-4373269 | 9.94 |
| 137 | mmu-miR-33*-4395247 | 9.95 |
| 138 | mmu-miR-188-5p-4395431 | 10.01 |
| 139 | mmu-miR-142-3p-4373136 | 10.05 |
| 140 | mmu-miR-376b*-4395581 | 10.14 |
| 141 | mmu-miR-148a-4373130 | 10.16 |
| 142 | mmu-miR-325*-4373334 | 10.26 |
| 143 | mmu-miR-22*-4395412 | 10.28 |
| 144 | mmu-miR-455*-4378098 | 10.41 |
| 145 | mmu-miR-28-4373067 | 10.41 |
| 146 | mmu-miR-27b-4373068 | 10.44 |
| 147 | mmu-miR-138*-4395684 | 10.48 |
| 148 | mmu-miR-708-4395452 | 10.51 |
| 149 | mmu-miR-744-4395435 | 10.54 |
| 150 | rno-miR-190b-4395749 | 10.74 |
| 151 | mmu-miR-101a-4395364 | 10.75 |
| 152 | mmu-miR-704-4386745 | 10.76 |
| 153 | mmu-miR-804-4395576 | 10.83 |
| 154 | mmu-miR-27a-4373287 | 10.92 |
| 155 | mmu-miR-21-4373090 | 10.96 |
| 156 | mmu-miR-15b-4373122 | 10.96 |
| 157 | mmu-miR-143-4395360 | 10.97 |
| 158 | mmu-miR-193*-4395707 | 10.97 |
| 159 | mmu-miR-192-4373108 | 11.07 |
| 160 | mmu-miR-411-4381013 | 11.09 |
| 161 | mmu-miR-543-4395487 | 11.11 |
| 162 | mmu-miR-181c-4373115 | 11.12 |
| 163 | mmu-miR-24-2*-4395624 | 11.19 |
| 164 | mmu-miR-29c-4395171 | 11.21 |
| 165 | mmu-miR-331-5p-4395344 | 11.22 |
| 166 | mmu-miR-674*-4386773 | 11.24 |
| 167 | mmu-miR-96-4373372 | 11.28 |
| 168 | mmu-miR-326-4373335 | 11.37 |
| 169 | mmu-miR-433-4373205 | 11.40 |
| 170 | mmu-miR-29c*-4381131 | 11.49 |
| 171 | mmu-let-7c-1*-4395609 | 11.52 |
| 172 | mmu-miR-15a-4373123 | 11.55 |
| 173 | mmu-miR-194-4373106 | 11.58 |
| 174 | mmu-miR-133b-4395358 | 11.88 |
| 175 | mmu-miR-324-5p-4373052 | 11.97 |
| 176 | mmu-miR-128a-4395327 | 11.97 |
| 177 | mmu-miR-875-5p-4395314 | 12.08 |
| 178 | mmu-miR-497-4381046 | 12.21 |
| 179 | mmu-miR-409-3p-4395443 | 12.21 |
| 180 | mmu-miR-136-4395641 | 12.21 |
| 181 | mmu-miR-384-3p-4395733 | 12.27 |
| 182 | rno-miR-29b-2*-4395277 | 12.44 |
| 183 | mmu-miR-340-5p-4395369 | 12.49 |
| 184 | mmu-miR-7a-4378130 | 12.51 |
| 185 | mmu-miR-296-5p-4373066 | 12.51 |
| 186 | mmu-miR-155-4395701 | 12.53 |
| 187 | mmu-miR-410-4378093 | 12.54 |
| 188 | mmu-miR-26b*-4395555 | 12.61 |
| 189 | mmu-miR-376c-4395580 | 12.61 |
| 190 | mmu-miR-130b-4373144 | 12.69 |
| 191 | mmu-miR-671-3p-4395433 | 12.72 |
| 192 | mmu-miR-872-4395375 | 12.72 |
| 193 | mmu-miR-879*-4395603 | 12.83 |
| 194 | mmu-miR-34b-3p-4395748 | 12.85 |
| 195 | mmu-miR-323-3p-4395338 | 12.86 |
| 196 | mmu-miR-125b-3p-4395489 | 12.96 |

TABLE 6-continued

Normal rat's VITREOUS TRANSCRIPTOME

| | miRNA | AVE DCt (ctr) |
|---|---|---|
| 197 | rno-miR-30d*-4395416 | 13.01 |
| 198 | mmu-miR-199a-3p-4395415 | 13.02 |
| 199 | mmu-miR-224-4395683 | 13.02 |
| 200 | mmu-miR-383-4381093 | 13.03 |
| 201 | mmu-miR-25-4373071 | 13.07 |
| 202 | mmu-miR-18a-4395533 | 13.09 |
| 203 | mmu-miR-652-4395463 | 13.12 |
| 204 | rno-miR-450a-4381124 | 13.24 |
| 205 | mmu-miR-197-4373102 | 13.27 |
| 206 | rno-miR-345-3p-4395762 | 13.29 |
| 207 | mmu-miR-361-4373035 | 13.34 |
| 208 | rno-miR-532-5p-4395752 | 13.34 |
| 209 | mmu-miR-494-4395476 | 13.36 |
| 210 | mmu-miR-190-4373110 | 13.39 |
| 211 | mmu-miR-7b-4395685 | 13.51 |
| 212 | mmu-miR-598-4395606 | 13.73 |
| 213 | mmu-miR-17*-4395673 | 13.74 |
| 214 | mmu-miR-378*-4373024 | 13.77 |
| 215 | mmu-miR-340-3p-4395370 | 14.00 |
| 216 | mmu-miR-125a-3p-4395310 | 14.13 |
| 217 | mmu-miR-337-5p-4395645 | 14.17 |
| 218 | rno-miR-743a-4395757 | 14.19 |
| 219 | mmu-miR-142-5p-4395359 | 14.24 |
| 220 | mmu-miR-805-4395577 | 14.25 |
| 221 | mmu-miR-376a-4373347 | 14.27 |
| 222 | mmu-miR-218-1*-4395682 | 14.30 |
| 223 | mmu-miR-338-3p-4395363 | 14.33 |
| 224 | mmu-miR-698-4381055 | 14.39 |
| 225 | rno-miR-219-1-3p-4395778 | 14.43 |
| 226 | mmu-miR-130b*-4395590 | 14.45 |
| 227 | mmu-miR-451-4373360 | 14.51 |
| 228 | mmu-miR-434-5p-4395711 | 14.60 |
| 229 | mmu-miR-329-4373336 | 14.63 |
| 230 | mmu-miR-27b*-4395285 | 14.93 |
| 231 | rno-miR-17-3p-4395779 | 14.95 |
| 232 | mmu-miR-694-4381090 | 14.96 |
| 233 | mmu-miR-29b-4373288 | 15.25 |
| 234 | mmu-miR-369-5p-4373195 | 15.36 |
| 235 | mmu-miR-137-4373301 | 15.36 |
| 236 | mmu-miR-190b-4395374 | 15.37 |

TABLE 7

Diabetic rat's VITREOUS TRANSCRIPTOME

| | miRNA | AVE DCt (STZ) |
|---|---|---|
| 1 | mmu-miR-204 | −1.05 |
| 2 | mmu-miR-720 | 0.32 |
| 3 | mmu-miR-709 | 0.84 |
| 4 | mmu-miR-211 | 1.06 |
| 5 | mmu-miR-466d-3p | 1.43 |
| 6 | mmu-miR-106a | 2.03 |
| 7 | mmu-miR-17 | 2.09 |
| 8 | mmu-miR-30c | 2.37 |
| 9 | mmu-miR-30b-4373290 | 2.49 |
| 10 | mmu-miR-184-4373113 | 2.81 |
| 11 | mmu-miR-24-4373072 | 3.13 |
| 12 | mmu-miR-26a-4395166 | 3.29 |
| 13 | mmu-miR-9-4373285 | 3.34 |
| 14 | mmu-miR-690-4381086 | 3.43 |
| 15 | mmu-miR-191-4395410 | 3.44 |
| 16 | mmu-miR-145-4395389 | 3.63 |
| 17 | mmu-let-7b-4373168 | 3.93 |
| 18 | mmu-let-7c-4373167 | 4.03 |
| 19 | mmu-miR-125b-5p-4373148 | 4.10 |
| 20 | mmu-miR-16-4373121 | 4.20 |
| 21 | mmu-miR-19b-4373098 | 4.39 |
| 22 | mmu-let-7e-4395517 | 4.49 |
| 23 | mmu-miR-328-4373049 | 4.49 |
| 24 | mmu-miR-210-4373089 | 4.58 |
| 25 | mmu-miR-99a-4373008 | 4.65 |
| 26 | mmu-miR-126-3p-4395339 | 4.70 |

TABLE 7-continued

Diabetic rat's VITREOUS TRANSCRIPTOME

| | miRNA | AVE DCt (STZ) |
|---|---|---|
| 27 | mmu-miR-182-4395729 | 4.70 |
| 28 | rno-miR-664-4381103 | 4.75 |
| 29 | mmu-miR-132-4373143 | 4.85 |
| 30 | mmu-miR-9*-4395342 | 4.91 |
| 31 | mmu-miR-467a*-4386757 | 4.93 |
| 32 | mmu-miR-30e*-4373057 | 5.00 |
| 33 | mmu-miR-99b-4373007 | 5.09 |
| 34 | mmu-miR-139-5p-4395400 | 5.14 |
| 35 | mmu-miR-146a-4373132 | 5.14 |
| 36 | rno-miR-204*-4395777 | 5.14 |
| 37 | rno-miR-100-4373160 | 5.16 |
| 38 | mmu-miR-384-5p-4395732 | 5.22 |
| 39 | mmu-miR-149-4395366 | 5.23 |
| 40 | mmu-miR-138-4395395 | 5.23 |
| 41 | mmu-miR-30a*-4373062 | 5.26 |
| 42 | mmu-miR-183-4395380 | 5.38 |
| 43 | mmu-let-7i-4395332 | 5.44 |
| 44 | mmu-miR-26b-4395167 | 5.50 |
| 45 | mmu-miR-181a-4373117 | 5.53 |
| 46 | mmu-miR-183*-4395381 | 5.55 |
| 47 | mmu-let-7d-4395394 | 5.66 |
| 48 | mmu-miR-150-4373127 | 5.70 |
| 49 | mmu-miR-342-3p-4395371 | 5.76 |
| 50 | mmu-miR-223-4395406 | 5.80 |
| 51 | mmu-miR-699-4381056 | 5.83 |
| 52 | rno-miR-7a*-4395763 | 5.84 |
| 53 | mmu-miR-877*-4395678 | 5.99 |
| 54 | mmu-miR-20a-4373286 | 6.00 |
| 55 | mmu-miR-29a-4395223 | 6.05 |
| 56 | mmu-miR-218-4373081 | 6.13 |
| 57 | mmu-miR-30a-4373061 | 6.16 |
| 58 | mmu-miR-434-3p-4395734 | 6.20 |
| 59 | mmu-miR-20b-4373263 | 6.24 |
| 60 | mmu-miR-320-4395388 | 6.26 |
| 61 | mmu-miR-127-4373147 | 6.33 |
| 62 | mmu-miR-678-4381076 | 6.35 |
| 63 | mmu-miR-141*-4395643 | 6.39 |
| 64 | mmu-miR-92a-4373013 | 6.41 |
| 65 | mmu-miR-375-4373027 | 6.47 |
| 66 | mmu-miR-7a*-4381118 | 6.47 |
| 67 | mmu-miR-30e-4395334 | 6.51 |
| 68 | mmu-let-7g-4395393 | 6.51 |
| 69 | mmu-miR-129-3p-4373297 | 6.69 |
| 70 | rno-miR-20b-5p-4381106 | 6.75 |
| 71 | mmu-miR-764-5p-4395568 | 6.79 |
| 72 | mmu-miR-140-4373374 | 6.84 |
| 73 | mmu-miR-222-4395387 | 6.86 |
| 74 | mmu-miR-124-4373295 | 6.92 |
| 75 | mmu-miR-29b*-4395627 | 6.94 |
| 76 | mmu-miR-331-3p-4373046 | 7.07 |
| 77 | mmu-miR-135b-4395372 | 7.16 |
| 78 | mmu-miR-125a-5p-4395309 | 7.27 |
| 79 | mmu-miR-485*-4386764 | 7.30 |
| 80 | mmu-miR-29a*-4395558 | 7.31 |
| 81 | mmu-miR-21-4373090 | 7.33 |
| 82 | mmu-miR-135a-4373140 | 7.34 |
| 83 | mmu-miR-760-4395439 | 7.36 |
| 84 | mmu-miR-103-4373158 | 7.37 |
| 85 | mmu-miR-195-4373105 | 7.39 |
| 86 | mmu-miR-30d-4373059 | 7.47 |
| 87 | mmu-miR-143-4395360 | 7.51 |
| 88 | mmu-miR-379-4373349 | 7.52 |
| 89 | mmu-miR-93-4373302 | 7.58 |
| 90 | mmu-miR-126-5p-4373269 | 7.61 |
| 91 | mmu-miR-203-4373095 | 7.66 |
| 92 | mmu-miR-484-4381032 | 7.82 |
| 93 | mmu-miR-23b-4373073 | 7.89 |
| 94 | mmu-miR-24-2*-4395624 | 7.92 |
| 95 | mmu-miR-99b*-4395307 | 7.98 |
| 96 | mmu-let-7a*-4395608 | 7.99 |
| 97 | mmu-miR-135a*-4395343 | 7.99 |
| 98 | mmu-miR-31-4373331 | 8.00 |
| 99 | mmu-miR-133a-4395357 | 8.02 |
| 100 | mmu-miR-301a-4373064 | 8.04 |
| 101 | mmu-miR-495-4381078 | 8.10 |
| 102 | mmu-miR-134-4373299 | 8.14 |

TABLE 7-continued

Diabetic rat's VITREOUS TRANSCRIPTOME

| | miRNA | AVE DCt (STZ) |
|---|---|---|
| 103 | mmu-miR-186-4395396 | 8.17 |
| 104 | mmu-miR-152-4395170 | 8.18 |
| 105 | mmu-miR-532-3p-4395466 | 8.19 |
| 106 | mmu-miR-146b-4373178 | 8.24 |
| 107 | mmu-miR-365-4373194 | 8.24 |
| 108 | mmu-miR-130a-4373145 | 8.24 |
| 109 | mmu-miR-335-3p-4395296 | 8.30 |
| 110 | mmu-miR-193b-4395597 | 8.32 |
| 111 | mmu-miR-335-5p-4373045 | 8.35 |
| 112 | mmu-miR-301b-4395730 | 8.35 |
| 113 | mmu-miR-142-3p-4373136 | 8.38 |
| 114 | mmu-miR-200c-4395411 | 8.40 |
| 115 | mmu-miR-574-3p-4395460 | 8.52 |
| 116 | mmu-miR-151-3p-4373304 | 8.54 |
| 117 | mmu-miR-181a-1*-4373086 | 8.57 |
| 118 | mmu-miR-31*-4395625 | 8.59 |
| 119 | mmu-miR-378-4395354 | 8.64 |
| 120 | mmu-miR-708-4395452 | 8.65 |
| 121 | mmu-miR-22-4373079 | 8.76 |
| 122 | mmu-miR-129-5p-4373171 | 8.78 |
| 123 | mmu-miR-543-4395487 | 8.80 |
| 124 | mmu-miR-27a-4373287 | 8.83 |
| 125 | mmu-miR-28-4373067 | 8.84 |
| 126 | rno-miR-190b-4395749 | 8.85 |
| 127 | mmu-miR-15a-4373123 | 8.87 |
| 128 | mmu-miR-101b-4395661 | 8.93 |
| 129 | mmu-miR-22*-4395412 | 9.01 |
| 130 | mmu-miR-101a-4395364 | 9.08 |
| 131 | mmu-miR-106b-4373155 | 9.09 |
| 132 | mmu-miR-148a-4373130 | 9.14 |
| 133 | mmu-miR-29c-4395171 | 9.19 |
| 134 | mmu-miR-667-4386769 | 9.21 |
| 135 | mmu-miR-27b-4373068 | 9.22 |
| 136 | mmu-miR-411-4381013 | 9.26 |
| 137 | mmu-miR-205-4373093 | 9.27 |
| 138 | mmu-miR-96-4373372 | 9.32 |
| 139 | rno-miR-30d*-4395416 | 9.37 |
| 140 | mmu-miR-497-4381046 | 9.37 |
| 141 | mmu-miR-19a-4373099 | 9.39 |
| 142 | mmu-miR-224-4395683 | 9.40 |
| 143 | mmu-miR-467b*-4381092 | 9.40 |
| 144 | mmu-miR-125b*-4395638 | 9.46 |
| 145 | mmu-miR-136-4395641 | 9.47 |
| 146 | mmu-miR-206-4373092 | 9.47 |
| 147 | rno-miR-463-4395751 | 9.53 |
| 148 | mmu-miR-376b*-4395581 | 9.58 |
| 149 | mmu-miR-592-4395560 | 9.59 |
| 150 | mmu-miR-744-4395435 | 9.60 |
| 151 | mmu-miR-324-5p-4373052 | 9.64 |
| 152 | mmu-miR-706-4381061 | 9.64 |
| 153 | rno-miR-125b*-4395775 | 9.66 |
| 154 | rno-miR-1-4395765 | 9.71 |
| 155 | mmu-miR-872*-4395672 | 9.73 |
| 156 | mmu-miR-15b-4373122 | 9.76 |
| 157 | rno-miR-532-5p-4395752 | 9.76 |
| 158 | mmu-miR-409-3p-4395443 | 9.85 |
| 159 | mmu-miR-194-4373106 | 9.86 |
| 160 | mmu-miR-181c-4373115 | 9.98 |
| 161 | mmu-miR-455-4395585 | 9.99 |
| 162 | mmu-miR-190-4373110 | 10.04 |
| 163 | mmu-miR-188-5p-4395431 | 10.08 |
| 164 | mmu-miR-323-3p-4395338 | 10.09 |
| 165 | mmu-miR-1-4395333 | 10.16 |
| 166 | mmu-miR-877-4395402 | 10.18 |
| 167 | mmu-miR-128a-4395327 | 10.21 |
| 168 | mmu-miR-192-4373108 | 10.22 |
| 169 | mmu-miR-455*-4378098 | 10.25 |
| 170 | mmu-miR-27a*-4395556 | 10.26 |
| 171 | mmu-miR-93*-4395250 | 10.27 |
| 172 | mmu-miR-29c*-4381131 | 10.30 |
| 173 | mmu-miR-199a-3p-4395415 | 10.35 |
| 174 | mmu-miR-25-4373071 | 10.39 |
| 175 | mmu-miR-423-5p-4395451 | 10.44 |
| 176 | mmu-miR-384-3p-4395733 | 10.48 |
| 177 | mmu-miR-33*-4395247 | 10.52 |
| 178 | mmu-miR-325-4395640 | 10.53 |
| 179 | mmu-miR-652-4395463 | 10.56 |
| 180 | mmu-miR-674*-4386773 | 10.57 |
| 181 | mmu-miR-7a-4378130 | 10.58 |
| 182 | mmu-miR-598-4395606 | 10.66 |
| 183 | mmu-miR-673-5p-4386772 | 10.70 |
| 184 | mmu-miR-410-4378093 | 10.79 |
| 185 | mmu-miR-34c*-4395714 | 10.80 |
| 186 | mmu-miR-872-4395375 | 10.81 |
| 187 | mmu-miR-671-3p-4395433 | 10.84 |
| 188 | rno-miR-450a-4381124 | 10.85 |
| 189 | rno-miR-381-4381102 | 10.88 |
| 190 | mmu-miR-361-4373035 | 10.88 |
| 191 | mmu-miR-340-5p-4395369 | 10.90 |
| 192 | mmu-miR-29b-4373288 | 10.97 |
| 193 | rno-miR-224-4373187 | 10.99 |
| 194 | mmu-miR-138*-4395684 | 11.05 |
| 195 | mmu-miR-704-4386745 | 11.13 |
| 196 | mmu-miR-148b-4373129 | 11.14 |
| 197 | rno-miR-17-3p-4395779 | 11.15 |
| 198 | mmu-miR-26b*-4395555 | 11.17 |
| 199 | mmu-miR-221-4373077 | 11.17 |
| 200 | mmu-miR-193*-4395707 | 11.21 |
| 201 | mmu-miR-296-5p-4373066 | 11.31 |
| 202 | mmu-miR-494-4395476 | 11.31 |
| 203 | mmu-miR-130b-4373144 | 11.32 |
| 204 | mmu-miR-672-4395438 | 11.44 |
| 205 | mmu-miR-376c-4395580 | 11.44 |
| 206 | mmu-miR-322-4378107 | 11.47 |
| 207 | mmu-miR-155-4395701 | 11.49 |
| 208 | mmu-miR-337-5p-4395645 | 11.55 |
| 209 | mmu-miR-340-3p-4395370 | 11.61 |
| 210 | rno-miR-505-4381097 | 11.61 |
| 211 | mmu-miR-28*-4395675 | 11.68 |
| 212 | mmu-miR-330*-4373337 | 11.73 |
| 213 | mmu-miR-433-4373205 | 11.74 |
| 214 | mmu-miR-7b-4395685 | 11.78 |
| 215 | mmu-miR-200b-4395362 | 11.85 |
| 216 | mmu-miR-125a-3p-4395310 | 11.90 |
| 217 | mmu-let-7c-1*-4395609 | 11.96 |
| 218 | mmu-miR-380-5p-4395731 | 12.01 |
| 219 | mmu-miR-879*-4395603 | 12.10 |
| 220 | mmu-miR-383-4381093 | 12.31 |
| 221 | mmu-miR-107-4373154 | 12.33 |
| 222 | mmu-miR-376a-4373347 | 12.36 |
| 223 | mmu-miR-685-4386748 | 12.36 |
| 224 | mmu-miR-338-3p-4395363 | 12.43 |
| 225 | rno-miR-207-4381096 | 12.47 |
| 226 | rno-miR-489-4381127 | 12.53 |
| 227 | rno-miR-29b-2*-4395277 | 12.63 |
| 228 | mmu-miR-875-5p-4395314 | 12.63 |
| 229 | mmu-miR-137-4373301 | 12.66 |
| 230 | mmu-miR-324-3p-4395639 | 12.67 |
| 231 | mmu-miR-378*-4373024 | 12.69 |
| 232 | rno-miR-136*-4395211 | 12.88 |
| 233 | rno-miR-333-4381109 | 12.94 |
| 234 | mmu-miR-185-4395382 | 12.95 |
| 235 | mmu-miR-197-4373102 | 13.11 |
| 236 | mmu-miR-878-3p-4395671 | 13.23 |
| 237 | mmu-miR-27b*-4395285 | 13.31 |
| 238 | mmu-miR-434-5p-4395711 | 13.40 |
| 239 | rno-miR-345-3p-4395762 | 13.41 |
| 240 | mmu-miR-325*-4373334 | 13.45 |
| 241 | mmu-miR-326-4373335 | 13.57 |
| 242 | mmu-miR-34b-3p-4395748 | 13.60 |
| 243 | mmu-miR-376a*-4395612 | 13.61 |
| 244 | mmu-miR-214*-4395404 | 13.65 |
| 245 | rno-miR-148b-5p-4395759 | 13.70 |
| 246 | mmu-miR-694-4381090 | 13.80 |
| 247 | rno-miR-351-4395764 | 13.91 |
| 248 | rno-miR-352-4381119 | 13.96 |
| 249 | rno-miR-99a*-4395774 | 13.96 |
| 250 | rno-let-7e*-4395518 | 13.98 |
| 251 | mmu-miR-805-4395577 | 14.15 |
| 252 | mmu-miR-191*-4395706 | 14.25 |
| 253 | mmu-miR-668-4386767 | 14.33 |
| 254 | mmu-miR-18a-4395533 | 14.38 |

TABLE 7-continued

Diabetic rat's VITREOUS TRANSCRIPTOME

| | miRNA | AVE DCt (STZ) |
|---|---|---|
| 255 | mmu-miR-544-4395680 | 14.63 |
| 256 | mmu-miR-337-3p-4395662 | 14.88 |
| 257 | mmu-miR-130b*-4395590 | 15.25 |
| 258 | mmu-miR-804-4395576 | 15.28 |
| 259 | mmu-miR-369-5p-4373195 | 15.36 |
| 260 | mmu-miR-190b-4395374 | 15.39 |
| 261 | mmu-miR-350-4395660 | 15.57 |
| 262 | mmu-miR-362-3p-4395746 | 15.93 |
| 263 | mmu-miR-369-3p-4373032 | 15.93 |
| 264 | mmu-miR-215-4373316 | 15.95 |
| 265 | mmu-miR-363-4378090 | 15.95 |
| 266 | mmu-miR-329-4373336 | 16.01 |
| 267 | mmu-let-7g*-4395622 | 16.05 |
| 268 | mmu-miR-470*-4395719 | 16.15 |
| 269 | mmu-miR-451-4373360 | 16.15 |
| 270 | mmu-miR-744*-4395436 | 16.26 |
| 271 | mmu-miR-698-4381055 | 16.35 |
| 272 | mmu-miR-125b-3p-4395489 | 16.46 |
| 273 | mmu-miR-142-5p-4395359 | 16.47 |
| 274 | mmu-miR-322*-4395636 | 16.52 |
| 275 | mmu-miR-17*-4395673 | 16.91 |
| 276 | rno-miR-743a-4395757 | 17.20 |
| 277 | mmu-miR-218-1*-4395682 | 17.34 |
| 278 | mmu-miR-200a*-4373273 | 17.45 |
| 279 | mmu-miR-146b*-4395583 | 17.52 |

TABLE 8

Differentially expressed miRNAs in the vitreous (STZ/CTR)

| | miRNA | Fold change (STZ/ctr) | new p value | Sequence (SEQ ID NOS 37-65, respectively, in order of appearance) |
|---|---|---|---|---|
| 1 | rno-miR-7a* | 3265.19 | 0.0001 | ACAACAAAUCACAGUCUGCCAU |
| 2 | mmu-miR-877* | 3046.09 | 0.0002 | UGUCCUCUUCUCCCUCCUCCCA |
| 3 | mmu-miR-129-5p | 855.82 | 0.0002 | CUUUUUGCGGUCUGGGCUUGC |
| 4 | mmu-miR-322 | 45.11 | 0.0125 | CAGCAGCAAUUCAUGUUUUGGA |
| 5 | mmu-miR-214* | 18.60 | 0.0409 | UGCCUGUCUACACUUGCUGUGC |
| 6 | mmu-miR-143 | 15.63 | 0.0468 | UGAGAUGAAGCACUGUAGCUC |
| 7 | mmu-miR-544 | 15.44 | 0.0070 | AUUCUGCAUUUUUAGCAAGCUC |
| 8 | rno-miR-532-5p | 12.19 | 0.0222 | CAUGCCUUGAGUGUAGGACUGU |
| 9 | mmu-miR-191* | 8.79 | 0.0041 | GCUGCACUUGGAUUUCGUUCCC |
| 10 | mmu-miR-15a | 6.14 | 0.0181 | UAGCAGCACAUAAUGGUUUGUG |
| 11 | mmu-miR-126-5p | 4.78 | 0.0157 | CAUUAUUACUUUUGGUACGCG |
| 12 | mmu-miR-126-3p | 3.70 | 0.0046 | UCGUACCGUGAGUAAUAAUGCG |
| 13 | mmu-miR-140 | 3.66 | 0.0477 | CAGUGGUUUUACCCUAUGGUAG |
| 14 | mmu-miR-96 | 3.55 | 0.0492 | UUUGGCACUAGCACAUUUUUGCU |
| 15 | mmu-miR-375 | 3.50 | 0.0341 | UUUGUUCGUUCGGCUCGCGUGA |
| 16 | mmu-miR-182 | 3.23 | 0.0395 | UUUGGCAAUGGUAGAACUCACACCG |
| 17 | mmu-miR-100 | 3.17 | 0.0378 | AACCCGUAGAUCCGAACUUGUG |
| 18 | mmu-miR-26a | 2.91 | 0.0488 | UUCAAGUAAUCCAGGAUAGGCU |
| 19 | mmu-miR-30c | 2.86 | 0.0438 | UGUAAACAUCCUACACUCUCAGC |
| 20 | mmu-miR-129-3p | 2.70 | 0.0305 | AAGCCCUUACCCCAAAAAGUAU |
| 21 | mmu-miR-99a | 2.66 | 0.0279 | AACCCGUAGAUCCGAUCUUGUG |
| 22 | mmu-miR-467a* | 0.54 | 0.0156 | CAUAUACAUACACACACCUACA |
| 23 | mmu-miR-467b* | 0.42 | 0.0395 | AUAUACAUACACACACCAACAC |
| 24 | mmu-miR-673-5p | 0.36 | 0.0225 | CUCACAGCUCUGGUCCUUGGAG |
| 25 | rno-miR-463 | 0.36 | 0.0134 | UGAUAGACGCCAAUUUGGGUAG |
| 26 | mmu-miR-678 | 0.33 | 0.0211 | GUCUCGGUGCAAGGACUGGAGG |
| 27 | mmu-miR-141* | 0.32 | 0.0219 | UAACACUGUCUGGUAAAGAUGG |
| 28 | mmu-miR-764-5p | 0.31 | 0.0119 | GGUGCUCACAUGUCCUCCU |
| 29 | mmu-miR-804 | 0.03 | 0.0298 | UGUGAGUUGUUCCUCACCUGGA |

PUBLICATIONS

These publications are incorporated by reference to the extent they relate materials and methods disclosed herein.

1. Huang, F., Mehta, D., Predescu, S., Kim, K. S., Lum, H., *Endothelium* 14, 25 (January-February, 2007).
2. Kovacs, B., Lumayag, S., Cowan, C., Xu, S., *Invest Ophthalmol Vis Sci* 52, 4402 (June, 2011).
3. Lum, H. et al., *Am J Physiol Lung Cell Mol Physiol* 281, L546 (September, 2001).
4. Lum, H. et al., *Am J Physiol Heart Circ Physiol* 285, H1786 (October, 2003).

5. Mendell, J. T., *Cell* 133:217-222 (2008).
6. O'Donnell, J. J., 3rd et al., *Microvasc Res* 82, 105 (September, 2011).
7. Qiao, J. et al., *Am J Physiol Lung Cell Mol Physiol* 291, L91 (July, 2006).
8. Qiao, J., Huang, F., Lum, H., *Am J Physiol Lung Cell Mol Physiol* 284, L972 (June, 2003).
9. Vandesompele, J., et al., *Genome Biol* 3:RESEARCH0034 (2002).
10. Xu, S. et al, *J Biol Chem* 282, 25053 (Aug. 24, 2007).

The invention claimed is:

1. A method to inhibit diabetes-induced retinal vascular damage and diabetic retinopathy in a diabetic mammal, the method comprising:
   a) selecting microRNAs from the group consisting of miR-34a/b/c, miR-155 (SEQ ID NO: 70), let-7 (SEQ ID NOS: 71, 73-78), and combinations thereof; and
   b) administering the selected microRNAs to the retina and retinal vasculature of the diabetic mammal.

2. The method of claim 1 wherein the microRNAs selected inhibit NF-κB activation.

3. The method of claim 1 wherein the mammal is a human.

4. A method to inhibit diabetes-induced retinal vascular damage and diabetic retinopathy in a diabetic mammal, the method comprising:
   a) selecting let-7 (SEQ ID NOs: 71, 73-78); and
   b) administering the selected microRNA to the retina and retinal vasculature of the diabetic mammal.

* * * * *

SEQUENCE LISTING

```
<160> NUMBER OF SEQ ID NOS: 126

<210> SEQ ID NO 1
<211> LENGTH: 22
<212> TYPE: RNA
<213> ORGANISM: Rattus sp.

<400> SEQUENCE: 1
ugucaguuug ucaaauaccc ca                                              22

<210> SEQ ID NO 2
<211> LENGTH: 22
<212> TYPE: RNA
<213> ORGANISM: Rattus sp.

<400> SEQUENCE: 2
uggacggaga acugauaagg gu                                              22

<210> SEQ ID NO 3
<211> LENGTH: 22
<212> TYPE: RNA
<213> ORGANISM: Rattus sp.

<400> SEQUENCE: 3
cuccugacuc cagguccugu gu                                              22

<210> SEQ ID NO 4
<211> LENGTH: 23
<212> TYPE: RNA
<213> ORGANISM: Rattus sp.

<400> SEQUENCE: 4
ugcuaugcca acauauugcc auc                                             23

<210> SEQ ID NO 5
<211> LENGTH: 22
<212> TYPE: RNA
<213> ORGANISM: Rattus sp.

<400> SEQUENCE: 5
uuuuucauua uugcuccuga cc                                              22

<210> SEQ ID NO 6
<211> LENGTH: 22
<212> TYPE: RNA
<213> ORGANISM: Rattus sp.

<400> SEQUENCE: 6
aggcaagaug cuggcauagc ug                                              22

<210> SEQ ID NO 7
<211> LENGTH: 21
<212> TYPE: RNA
<213> ORGANISM: Rattus sp.

<400> SEQUENCE: 7
acuggacuug gagucagaag g                                               21
```

<210> SEQ ID NO 8
<211> LENGTH: 22
<212> TYPE: RNA
<213> ORGANISM: Rattus sp.

<400> SEQUENCE: 8
cacgcucaug cacacaccca ca                                              22

<210> SEQ ID NO 9
<211> LENGTH: 22
<212> TYPE: RNA
<213> ORGANISM: Rattus sp.

<400> SEQUENCE: 9
uccuucauuc caccggaguc ug                                              22

<210> SEQ ID NO 10
<211> LENGTH: 22
<212> TYPE: RNA
<213> ORGANISM: Rattus sp.

<400> SEQUENCE: 10
acaguagucu gcacauuggu ua                                              22

<210> SEQ ID NO 11
<211> LENGTH: 22
<212> TYPE: RNA
<213> ORGANISM: Rattus sp.

<400> SEQUENCE: 11
aaucacuaac uccacugcca uc                                              22

<210> SEQ ID NO 12
<211> LENGTH: 22
<212> TYPE: RNA
<213> ORGANISM: Rattus sp.

<400> SEQUENCE: 12
uaauacugcc ugguaaugau ga                                              22

<210> SEQ ID NO 13
<211> LENGTH: 23
<212> TYPE: RNA
<213> ORGANISM: Rattus sp.

<400> SEQUENCE: 13
ucaagagcaa uaacgaaaaa ugu                                             23

<210> SEQ ID NO 14
<211> LENGTH: 23
<212> TYPE: RNA
<213> ORGANISM: Rattus sp.

<400> SEQUENCE: 14
aggcagugua guuagcugau ugc                                             23

<210> SEQ ID NO 15
<211> LENGTH: 22
<212> TYPE: RNA
<213> ORGANISM: Rattus sp.

<400> SEQUENCE: 15
uaacacuguc ugguaacgau gu                                              22

<210> SEQ ID NO 16
<211> LENGTH: 21
<212> TYPE: RNA
<213> ORGANISM: Rattus sp.

<400> SEQUENCE: 16
uugaaaggcu guuucuuggu c                                              21

<210> SEQ ID NO 17
<211> LENGTH: 23
<212> TYPE: RNA
<213> ORGANISM: Rattus sp.

<400> SEQUENCE: 17
caaagugcuc auagugcagg uag                                            23

<210> SEQ ID NO 18
<211> LENGTH: 21
<212> TYPE: RNA
<213> ORGANISM: Rattus sp.

<400> SEQUENCE: 18
uuaagacuug cagugauguu u                                              21

<210> SEQ ID NO 19
<211> LENGTH: 22
<212> TYPE: RNA
<213> ORGANISM: Rattus sp.

<400> SEQUENCE: 19
aaaggcuagg cucacaacca aa                                             22

<210> SEQ ID NO 20
<211> LENGTH: 22
<212> TYPE: RNA
<213> ORGANISM: Rattus sp.

<400> SEQUENCE: 20
uagcagcaca ucaugguuua ca                                             22

<210> SEQ ID NO 21
<211> LENGTH: 23
<212> TYPE: RNA
<213> ORGANISM: Rattus sp.

<400> SEQUENCE: 21
ugugcaaauc caugcaaaac uga                                            23

<210> SEQ ID NO 22
<211> LENGTH: 22
<212> TYPE: RNA
<213> ORGANISM: Rattus sp.

<400> SEQUENCE: 22
uagcuuauca gacugauguu ga                                             22

<210> SEQ ID NO 23
<211> LENGTH: 22
<212> TYPE: RNA
<213> ORGANISM: Rattus sp.

<400> SEQUENCE: 23

| | |
|---|---|
| aggcaagaug cuggcauagc ug | 22 |

```
<210> SEQ ID NO 24
<211> LENGTH: 22
<212> TYPE: RNA
<213> ORGANISM: Rattus sp.

<400> SEQUENCE: 24
```

| | |
|---|---|
| uaacagucua cagccauggu cg | 22 |

```
<210> SEQ ID NO 25
<211> LENGTH: 23
<212> TYPE: RNA
<213> ORGANISM: Rattus sp.

<400> SEQUENCE: 25
```

| | |
|---|---|
| uguaguguuu ccuacuuuau gga | 23 |

```
<210> SEQ ID NO 26
<211> LENGTH: 22
<212> TYPE: RNA
<213> ORGANISM: Rattus sp.

<400> SEQUENCE: 26
```

| | |
|---|---|
| ugagaacuga auuccauggg uu | 22 |

```
<210> SEQ ID NO 27
<211> LENGTH: 23
<212> TYPE: RNA
<213> ORGANISM: Rattus sp.

<400> SEQUENCE: 27
```

| | |
|---|---|
| uuaaugcuaa uugugauagg ggu | 23 |

```
<210> SEQ ID NO 28
<211> LENGTH: 23
<212> TYPE: RNA
<213> ORGANISM: Rattus sp.

<400> SEQUENCE: 28
```

| | |
|---|---|
| ucccuguccu ccaggagcuc acg | 23 |

```
<210> SEQ ID NO 29
<211> LENGTH: 23
<212> TYPE: RNA
<213> ORGANISM: Rattus sp.

<400> SEQUENCE: 29
```

| | |
|---|---|
| ucucacacag aaaucgcacc cgu | 23 |

```
<210> SEQ ID NO 30
<211> LENGTH: 22
<212> TYPE: RNA
<213> ORGANISM: Rattus sp.

<400> SEQUENCE: 30
```

| | |
|---|---|
| uuuugcgaug uguuccuaau gu | 22 |

```
<210> SEQ ID NO 31
<211> LENGTH: 22
<212> TYPE: RNA
<213> ORGANISM: Rattus sp.

<400> SEQUENCE: 31
```
uagcaccauu ugaaaucggu ua                                                    22

<210> SEQ ID NO 32
<211> LENGTH: 21
<212> TYPE: RNA
<213> ORGANISM: Rattus sp.

<400> SEQUENCE: 32
uauugcacuu gucccggccu g                                                     21

<210> SEQ ID NO 33
<211> LENGTH: 22
<212> TYPE: RNA
<213> ORGANISM: Rattus sp.

<400> SEQUENCE: 33
aacauucaac cugucgguga gu                                                    22

<210> SEQ ID NO 34
<211> LENGTH: 21
<212> TYPE: RNA
<213> ORGANISM: Rattus sp.

<400> SEQUENCE: 34
aacauagagg aaauuucacg u                                                     21

<210> SEQ ID NO 35
<211> LENGTH: 22
<212> TYPE: RNA
<213> ORGANISM: Rattus sp.

<400> SEQUENCE: 35
caucaucguc ucaaaugagu cu                                                    22

<210> SEQ ID NO 36
<211> LENGTH: 23
<212> TYPE: RNA
<213> ORGANISM: Rattus sp.

<400> SEQUENCE: 36
caaagugcuc auagugcagg uag                                                   23

<210> SEQ ID NO 37
<211> LENGTH: 22
<212> TYPE: RNA
<213> ORGANISM: Rattus sp.

<400> SEQUENCE: 37
acaacaaauc acagucugcc au                                                    22

<210> SEQ ID NO 38
<211> LENGTH: 22
<212> TYPE: RNA
<213> ORGANISM: Rattus sp.

<400> SEQUENCE: 38
uguccucuuc ucccuccucc ca                                                    22

<210> SEQ ID NO 39
<211> LENGTH: 21
<212> TYPE: RNA
<213> ORGANISM: Rattus sp.

```
<400> SEQUENCE: 39
cuuuuugcgg ucugggcuug c                                              21

<210> SEQ ID NO 40
<211> LENGTH: 22
<212> TYPE: RNA
<213> ORGANISM: Rattus sp.

<400> SEQUENCE: 40
cagcagcaau ucauguuuug ga                                             22

<210> SEQ ID NO 41
<211> LENGTH: 22
<212> TYPE: RNA
<213> ORGANISM: Rattus sp.

<400> SEQUENCE: 41
ugccugucua cacuugcugu gc                                             22

<210> SEQ ID NO 42
<211> LENGTH: 21
<212> TYPE: RNA
<213> ORGANISM: Rattus sp.

<400> SEQUENCE: 42
ugagaugaag cacuguagcu c                                              21

<210> SEQ ID NO 43
<211> LENGTH: 22
<212> TYPE: RNA
<213> ORGANISM: Rattus sp.

<400> SEQUENCE: 43
auucugcauu uuuagcaagc uc                                             22

<210> SEQ ID NO 44
<211> LENGTH: 22
<212> TYPE: RNA
<213> ORGANISM: Rattus sp.

<400> SEQUENCE: 44
caugccuuga guguaggacu gu                                             22

<210> SEQ ID NO 45
<211> LENGTH: 22
<212> TYPE: RNA
<213> ORGANISM: Rattus sp.

<400> SEQUENCE: 45
gcugcacuug gauuucguuc cc                                             22

<210> SEQ ID NO 46
<211> LENGTH: 22
<212> TYPE: RNA
<213> ORGANISM: Rattus sp.

<400> SEQUENCE: 46
uagcagcaca uaaugguuug ug                                             22

<210> SEQ ID NO 47
<211> LENGTH: 21
<212> TYPE: RNA
<213> ORGANISM: Rattus sp.
```

```
<400> SEQUENCE: 47
cauuauuacu uuugguacgc g                                              21

<210> SEQ ID NO 48
<211> LENGTH: 22
<212> TYPE: RNA
<213> ORGANISM: Rattus sp.

<400> SEQUENCE: 48
ucguaccgug aguaauaaug cg                                             22

<210> SEQ ID NO 49
<211> LENGTH: 22
<212> TYPE: RNA
<213> ORGANISM: Rattus sp.

<400> SEQUENCE: 49
cagugguuuu acccuauggu ag                                             22

<210> SEQ ID NO 50
<211> LENGTH: 23
<212> TYPE: RNA
<213> ORGANISM: Rattus sp.

<400> SEQUENCE: 50
uuuggcacua gcacauuuuu gcu                                            23

<210> SEQ ID NO 51
<211> LENGTH: 22
<212> TYPE: RNA
<213> ORGANISM: Rattus sp.

<400> SEQUENCE: 51
uuuguucguu cggcucgcgu ga                                             22

<210> SEQ ID NO 52
<211> LENGTH: 25
<212> TYPE: RNA
<213> ORGANISM: Rattus sp.

<400> SEQUENCE: 52
uuuggcaaug guagaacuca caccg                                          25

<210> SEQ ID NO 53
<211> LENGTH: 22
<212> TYPE: RNA
<213> ORGANISM: Rattus sp.

<400> SEQUENCE: 53
aacccguaga uccgaacuug ug                                             22

<210> SEQ ID NO 54
<211> LENGTH: 22
<212> TYPE: RNA
<213> ORGANISM: Rattus sp.

<400> SEQUENCE: 54
uucaaguaau ccaggauagg cu                                             22

<210> SEQ ID NO 55
<211> LENGTH: 23
<212> TYPE: RNA
```

```
<213> ORGANISM: Rattus sp.

<400> SEQUENCE: 55
uguaaacauc cuacacucuc agc                                             23

<210> SEQ ID NO 56
<211> LENGTH: 22
<212> TYPE: RNA
<213> ORGANISM: Rattus sp.

<400> SEQUENCE: 56
aagcccuuac cccaaaaagu au                                              22

<210> SEQ ID NO 57
<211> LENGTH: 22
<212> TYPE: RNA
<213> ORGANISM: Rattus sp.

<400> SEQUENCE: 57
aacccguaga uccgaucuug ug                                              22

<210> SEQ ID NO 58
<211> LENGTH: 22
<212> TYPE: RNA
<213> ORGANISM: Rattus sp.

<400> SEQUENCE: 58
cauauacaua cacacaccua ca                                              22

<210> SEQ ID NO 59
<211> LENGTH: 22
<212> TYPE: RNA
<213> ORGANISM: Rattus sp.

<400> SEQUENCE: 59
auauacauac acacaccaac ac                                              22

<210> SEQ ID NO 60
<211> LENGTH: 22
<212> TYPE: RNA
<213> ORGANISM: Rattus sp.

<400> SEQUENCE: 60
cucacagcuc ugguccuugg ag                                              22

<210> SEQ ID NO 61
<211> LENGTH: 22
<212> TYPE: RNA
<213> ORGANISM: Rattus sp.

<400> SEQUENCE: 61
ugauagacgc caauuugggu ag                                              22

<210> SEQ ID NO 62
<211> LENGTH: 22
<212> TYPE: RNA
<213> ORGANISM: Rattus sp.

<400> SEQUENCE: 62
gucucggugc aaggacugga gg                                              22

<210> SEQ ID NO 63
<211> LENGTH: 22
```

<212> TYPE: RNA
<213> ORGANISM: Rattus sp.

<400> SEQUENCE: 63
uaacacuguc ugguaaagau gg                                22

<210> SEQ ID NO 64
<211> LENGTH: 19
<212> TYPE: RNA
<213> ORGANISM: Rattus sp.

<400> SEQUENCE: 64
ggugcucaca uguccuccu                                    19

<210> SEQ ID NO 65
<211> LENGTH: 22
<212> TYPE: RNA
<213> ORGANISM: Rattus sp.

<400> SEQUENCE: 65
ugugaguugu uccucaccug ga                                22

<210> SEQ ID NO 66
<211> LENGTH: 22
<212> TYPE: RNA
<213> ORGANISM: Rattus sp.

<400> SEQUENCE: 66
uagcuuauca gacugauguu ga                                22

<210> SEQ ID NO 67
<211> LENGTH: 22
<212> TYPE: RNA
<213> ORGANISM: Rattus sp.

<400> SEQUENCE: 67
uaacagucua cagccauggu cg                                22

<210> SEQ ID NO 68
<211> LENGTH: 22
<212> TYPE: RNA
<213> ORGANISM: Rattus sp.

<400> SEQUENCE: 68
ugagaacuga auuccauggg uu                                22

<210> SEQ ID NO 69
<211> LENGTH: 24
<212> TYPE: RNA
<213> ORGANISM: Rattus sp.

<400> SEQUENCE: 69
ugagaacuga auuccauagg cugu                              24

<210> SEQ ID NO 70
<211> LENGTH: 23
<212> TYPE: RNA
<213> ORGANISM: Rattus sp.

<400> SEQUENCE: 70
uuaaugcuaa uugugauagg ggu                               23

<210> SEQ ID NO 71

```
<211> LENGTH: 22
<212> TYPE: RNA
<213> ORGANISM: Rattus sp.

<400> SEQUENCE: 71
ugagguagua gguuguauag uu                                              22

<210> SEQ ID NO 72
<211> LENGTH: 22
<212> TYPE: RNA
<213> ORGANISM: Rattus sp.

<400> SEQUENCE: 72
ugagguagua gguugugugg uu                                              22

<210> SEQ ID NO 73
<211> LENGTH: 22
<212> TYPE: RNA
<213> ORGANISM: Rattus sp.

<400> SEQUENCE: 73
ugagguagua gguuguaugg uu                                              22

<210> SEQ ID NO 74
<211> LENGTH: 22
<212> TYPE: RNA
<213> ORGANISM: Rattus sp.

<400> SEQUENCE: 74
agagguagua gguugcauag uu                                              22

<210> SEQ ID NO 75
<211> LENGTH: 22
<212> TYPE: RNA
<213> ORGANISM: Rattus sp.

<400> SEQUENCE: 75
ugagguagga gguuguauag uu                                              22

<210> SEQ ID NO 76
<211> LENGTH: 22
<212> TYPE: RNA
<213> ORGANISM: Rattus sp.

<400> SEQUENCE: 76
ugagguagua gauuguauag uu                                              22

<210> SEQ ID NO 77
<211> LENGTH: 22
<212> TYPE: RNA
<213> ORGANISM: Rattus sp.

<400> SEQUENCE: 77
ugagguagua guuugugcug uu                                              22

<210> SEQ ID NO 78
<211> LENGTH: 22
<212> TYPE: RNA
<213> ORGANISM: Rattus sp.

<400> SEQUENCE: 78
ugagguagua guuuguacag uu                                              22
```

```
<210> SEQ ID NO 79
<211> LENGTH: 23
<212> TYPE: RNA
<213> ORGANISM: Rattus sp.

<400> SEQUENCE: 79
caaagugcuu acagugcagg uag                                           23

<210> SEQ ID NO 80
<211> LENGTH: 21
<212> TYPE: RNA
<213> ORGANISM: Rattus sp.

<400> SEQUENCE: 80
caaagugcuc auagugcagg u                                             21

<210> SEQ ID NO 81
<211> LENGTH: 23
<212> TYPE: RNA
<213> ORGANISM: Rattus sp.

<400> SEQUENCE: 81
caaagugcug uucgugcagg uag                                           23

<210> SEQ ID NO 82
<211> LENGTH: 23
<212> TYPE: RNA
<213> ORGANISM: Rattus sp.

<400> SEQUENCE: 82
uaaagugcuu auagugcagg uag                                           23

<210> SEQ ID NO 83
<211> LENGTH: 21
<212> TYPE: RNA
<213> ORGANISM: Rattus sp.

<400> SEQUENCE: 83
uaaagugcug acagugcaga u                                             21

<210> SEQ ID NO 84
<211> LENGTH: 23
<212> TYPE: RNA
<213> ORGANISM: Rattus sp.

<400> SEQUENCE: 84
uaaggugcau cuagugcaga uag                                           23

<210> SEQ ID NO 85
<211> LENGTH: 23
<212> TYPE: RNA
<213> ORGANISM: Rattus sp.

<400> SEQUENCE: 85
ugugcaaauc uaugcaaaac uga                                           23

<210> SEQ ID NO 86
<211> LENGTH: 23
<212> TYPE: RNA
<213> ORGANISM: Rattus sp.

<400> SEQUENCE: 86
ugugcaaauc caugcaaaac uga                                           23
```

```
<210> SEQ ID NO 87
<211> LENGTH: 22
<212> TYPE: RNA
<213> ORGANISM: Rattus sp.

<400> SEQUENCE: 87
cauugcacuu gucucggucu ga                                              22

<210> SEQ ID NO 88
<211> LENGTH: 22
<212> TYPE: RNA
<213> ORGANISM: Rattus sp.

<400> SEQUENCE: 88
aauugcacgg uauccaucug ua                                              22

<210> SEQ ID NO 89
<211> LENGTH: 21
<212> TYPE: RNA
<213> ORGANISM: Rattus sp.

<400> SEQUENCE: 89
uauugcacuu gucccggccu g                                               21

<210> SEQ ID NO 90
<211> LENGTH: 22
<212> TYPE: RNA
<213> ORGANISM: Rattus sp.

<400> SEQUENCE: 90
uagcagcaca ucaugguuua ca                                              22

<210> SEQ ID NO 91
<211> LENGTH: 22
<212> TYPE: RNA
<213> ORGANISM: Rattus sp.

<400> SEQUENCE: 91
uagcagcacg uaaauauugg cg                                              22

<210> SEQ ID NO 92
<211> LENGTH: 22
<212> TYPE: RNA
<213> ORGANISM: Rattus sp.

<400> SEQUENCE: 92
uagcuuauca gacugauguu ga                                              22

<210> SEQ ID NO 93
<211> LENGTH: 22
<212> TYPE: RNA
<213> ORGANISM: Rattus sp.

<400> SEQUENCE: 93
aggcaagaug cuggcauagc ug                                              22

<210> SEQ ID NO 94
<211> LENGTH: 22
<212> TYPE: RNA
<213> ORGANISM: Rattus sp.

<400> SEQUENCE: 94
uggacggaga acugauaagg gu                                              22
```

<210> SEQ ID NO 95
<211> LENGTH: 21
<212> TYPE: RNA
<213> ORGANISM: Rattus sp.

<400> SEQUENCE: 95
acuggacuug gagucagaag g					21

<210> SEQ ID NO 96
<211> LENGTH: 22
<212> TYPE: RNA
<213> ORGANISM: Homo sapiens

<400> SEQUENCE: 96
ugagaacuga auuccauggg uu					22

<210> SEQ ID NO 97
<211> LENGTH: 22
<212> TYPE: RNA
<213> ORGANISM: Mus sp.

<400> SEQUENCE: 97
ugagaacuga auuccauggg uu					22

<210> SEQ ID NO 98
<211> LENGTH: 22
<212> TYPE: RNA
<213> ORGANISM: Rattus sp.

<400> SEQUENCE: 98
ugagaacuga auuccauggg uu					22

<210> SEQ ID NO 99
<211> LENGTH: 22
<212> TYPE: RNA
<213> ORGANISM: Homo sapiens

<400> SEQUENCE: 99
ugagaacuga auuccauagg cu					22

<210> SEQ ID NO 100
<211> LENGTH: 22
<212> TYPE: RNA
<213> ORGANISM: Mus sp.

<400> SEQUENCE: 100
ugagaacuga auuccauagg cu					22

<210> SEQ ID NO 101
<211> LENGTH: 24
<212> TYPE: RNA
<213> ORGANISM: Rattus sp.

<400> SEQUENCE: 101
ugagaacuga auuccauagg cugu					24

<210> SEQ ID NO 102
<211> LENGTH: 22
<212> TYPE: RNA
<213> ORGANISM: Rattus sp.

<400> SEQUENCE: 102
uggcaguguc uuagcugguu gu    22

<210> SEQ ID NO 103
<211> LENGTH: 23
<212> TYPE: RNA
<213> ORGANISM: Rattus sp.

<400> SEQUENCE: 103
aggcagugua auuagcugau ugu    23

<210> SEQ ID NO 104
<211> LENGTH: 23
<212> TYPE: RNA
<213> ORGANISM: Rattus sp.

<400> SEQUENCE: 104
aggcagugua guuagcugau ugc    23

<210> SEQ ID NO 105
<211> LENGTH: 22
<212> TYPE: RNA
<213> ORGANISM: Rattus sp.

<400> SEQUENCE: 105
aaucacuaac uccacugcca uc    22

<210> SEQ ID NO 106
<211> LENGTH: 23
<212> TYPE: RNA
<213> ORGANISM: Homo sapiens

<400> SEQUENCE: 106
cucgcccugg agucuguucu cac    23

<210> SEQ ID NO 107
<211> LENGTH: 23
<212> TYPE: RNA
<213> ORGANISM: Mus sp.

<400> SEQUENCE: 107
cacacccugg aauagaguuc uca    23

<210> SEQ ID NO 108
<211> LENGTH: 23
<212> TYPE: RNA
<213> ORGANISM: Rattus sp.

<400> SEQUENCE: 108
cucacccugg aauagaguuc uca    23

<210> SEQ ID NO 109
<211> LENGTH: 22
<212> TYPE: RNA
<213> ORGANISM: Homo sapiens

<400> SEQUENCE: 109
ugagaacuga auuccauggg uu    22

<210> SEQ ID NO 110
<211> LENGTH: 22
<212> TYPE: RNA
<213> ORGANISM: Homo sapiens

<400> SEQUENCE: 110

```
ugagaacuga auuccauagg cu                                              22

<210> SEQ ID NO 111
<211> LENGTH: 23
<212> TYPE: RNA
<213> ORGANISM: Homo sapiens

<400> SEQUENCE: 111
cucgcccugg agucuguucu cac                                             23

<210> SEQ ID NO 112
<211> LENGTH: 23
<212> TYPE: RNA
<213> ORGANISM: Pan troglodytes

<400> SEQUENCE: 112
cucgcccugg agucuguucu cac                                             23

<210> SEQ ID NO 113
<211> LENGTH: 23
<212> TYPE: RNA
<213> ORGANISM: Macaca mulatta

<400> SEQUENCE: 113
cucacccugg agucuguucu cac                                             23

<210> SEQ ID NO 114
<211> LENGTH: 23
<212> TYPE: RNA
<213> ORGANISM: Bos taurus

<400> SEQUENCE: 114
acacccgagg accauguucu cac                                             23

<210> SEQ ID NO 115
<211> LENGTH: 23
<212> TYPE: RNA
<213> ORGANISM: Canis familiaris

<400> SEQUENCE: 115
cacacugagg acgauguucu cac                                             23

<210> SEQ ID NO 116
<211> LENGTH: 23
<212> TYPE: RNA
<213> ORGANISM: Mus sp.

<400> SEQUENCE: 116
cacacccugg aauagaguuc uca                                             23

<210> SEQ ID NO 117
<211> LENGTH: 23
<212> TYPE: RNA
<213> ORGANISM: Rattus norvegicus

<400> SEQUENCE: 117
cucacccugg aauagaguuc uca                                             23

<210> SEQ ID NO 118
<211> LENGTH: 22
<212> TYPE: RNA
<213> ORGANISM: Homo sapiens
```

```
<400> SEQUENCE: 118
ugagaacuga auccauggg uu                                          22

<210> SEQ ID NO 119
<211> LENGTH: 22
<212> TYPE: RNA
<213> ORGANISM: Homo sapiens

<400> SEQUENCE: 119
ugagaacuga auccauagg cu                                          22

<210> SEQ ID NO 120
<211> LENGTH: 23
<212> TYPE: RNA
<213> ORGANISM: Homo sapiens

<400> SEQUENCE: 120
agguuugcac acucaaguuc uca                                        23

<210> SEQ ID NO 121
<211> LENGTH: 23
<212> TYPE: RNA
<213> ORGANISM: Macaca mulatta

<400> SEQUENCE: 121
agguuugcac acucaaguuc uca                                        23

<210> SEQ ID NO 122
<211> LENGTH: 23
<212> TYPE: RNA
<213> ORGANISM: Pan troglodytes

<400> SEQUENCE: 122
agguuugcac acucaaguuc uca                                        23

<210> SEQ ID NO 123
<211> LENGTH: 23
<212> TYPE: RNA
<213> ORGANISM: Canis familiaris

<400> SEQUENCE: 123
gguuuacaca ccugguucu cac                                         23

<210> SEQ ID NO 124
<211> LENGTH: 23
<212> TYPE: RNA
<213> ORGANISM: Bos taurus

<400> SEQUENCE: 124
ccucagagca ucugcguucu cag                                        23

<210> SEQ ID NO 125
<211> LENGTH: 22
<212> TYPE: RNA
<213> ORGANISM: Homo sapiens

<400> SEQUENCE: 125
ugagaacuga auccauggg uu                                          22

<210> SEQ ID NO 126
<211> LENGTH: 22
<212> TYPE: RNA
<213> ORGANISM: Homo sapiens
```

-continued

```
<400> SEQUENCE: 126
ugagaacuga auuccauagg cu                                              22
```